(12) United States Patent
Dasgupta et al.

(10) Patent No.: US 9,714,281 B2
(45) Date of Patent: *Jul. 25, 2017

(54) FIBRONECTIN BASED SCAFFOLD DOMAIN PROTEINS THAT BIND IL-23

(71) Applicant: BRISTOL-MYERS SQUIBB COMPANY, Princeton, NJ (US)

(72) Inventors: Ruchira Dasgupta, Auburndale, MA (US); Alex Bush, Brighton, MA (US); Lumelle Schneeweis, Monroe, NJ (US); Linda Engle, Framingham, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 239 days.

This patent is subject to a terminal disclaimer.

(21) Appl. No.: 14/553,379

(22) Filed: Nov. 25, 2014

(65) Prior Publication Data

US 2015/0274806 A1 Oct. 1, 2015

Related U.S. Application Data

(63) Continuation of application No. 13/579,204, filed as application No. PCT/US2011/024959 on Feb. 16, 2011, now Pat. No. 8,927,693.

(60) Provisional application No. 61/305,566, filed on Feb. 18, 2010, provisional application No. 61/330,706, filed on May 3, 2010.

(51) Int. Cl.
| | |
|---|---|
| *C07K 14/78* | (2006.01) |
| *C12N 15/10* | (2006.01) |
| *A61K 38/39* | (2006.01) |
| *A61K 47/48* | (2006.01) |
| *A61K 38/00* | (2006.01) |

(52) U.S. Cl.
CPC .............. *C07K 14/78* (2013.01); *A61K 38/39* (2013.01); *A61K 47/48215* (2013.01); *C12N 15/1044* (2013.01); *A61K 38/00* (2013.01); *C07K 2318/20* (2013.01); *C07K 2319/70* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,631,144 A | 5/1997 | Lemoine et al. |
| 5,672,502 A | 9/1997 | Birch et al. |
| 6,048,728 A | 4/2000 | Inlow et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,518,018 B1 | 2/2003 | Szostak et al. |
| 6,559,126 B2 | 5/2003 | Tournaire et al. |
| 6,818,418 B1 | 11/2004 | Lipovsek et al. |
| 7,115,396 B2 | 10/2006 | Lipovsek et al. |
| 2005/0038229 A1 | 2/2005 | Lipovsek et al. |
| 2005/0287153 A1 | 12/2005 | Dennis |
| 2007/0003549 A1 | 1/2007 | Ignatovich et al. |
| 2007/0148126 A1 | 6/2007 | Chen et al. |
| 2007/0178082 A1 | 8/2007 | Silence et al. |
| 2007/0269422 A1 | 11/2007 | Beirnaert et al. |
| 2013/0287775 A1 | 10/2013 | Bowman et al. |

FOREIGN PATENT DOCUMENTS

| | | |
|---|---|---|
| WO | WO9411026 | 5/1994 |
| WO | WO0204523 A2 | 1/2002 |
| WO | WO2008006675 A1 | 1/2008 |
| WO | WO2009133208 A1 | 5/2009 |
| WO | WO2009068649 A2 | 6/2009 |
| WO | WO2009102421 A1 | 8/2009 |
| WO | WO 2010/060095 A1 | 5/2010 |
| WO | WO2010112458 A1 | 10/2010 |

OTHER PUBLICATIONS

Ramamurthy, Vidhyashankar, et al., "Structures of Adnectin/Protein Complexes Reveal an Expanded Binding Footprint", Structure, vol. 20, Feb. 8, 2012, pp. 259-269.
Aggarwal, et al, "Interleukin-23 Promotes a District CD4 T Cell Activation State Characterized by the Production of Interleukin-17", J. Biol. Chem., vol. 278, No. 3, pp. 1910-1914 (2003).
Barnes, et al., "Methods for Growth of Cultured Cells in Serum-Free Medium", Analytical Biochem., vol. 102, pp. 255-270 (1980).
Batori, et al., "Exploring the potential of the monobody scaffold: effects of loop elongation on the stability of a fibronectin type III domain", Protein Engin., vol. 15, No. 12, pp. 1015-1020 (2002).
Connell, Nancy D., "Expression systems for use in actinomycetes and related organisms", Curr. Opinion in Biotech., vol. 12, pp. 446-449 (2001).
Ham, et al., "Media and Growth Requirements", Methods Enzymology, vol. LVIII (58), pp. 44-93 (1979).
Koide, et al., "Stabilization of a Fibronectin Type III Domain by the Removal of Unfavorable Electrostatic Interactions on the Protein Surface", Biochem, vol. 40, pp. 10326-10333 (2001).
Luckow, et al., "Trends in the Development of Baculovirus Expression Vectors", Biotech., vol. 6, pp. 47-55 (1988).
Makrides, Savvas C., Strategies for Achieving High-Level Expression of Genes in *Escherichia coil*, Microbiological Reviews, vol. 60, No. 3, pp. 512-538 (1996).

(Continued)

*Primary Examiner* — Brad Duffy
(74) *Attorney, Agent, or Firm* — Nickki L. Parlet

(57) ABSTRACT

The present invention relates to fibronectin based scaffold domain protein that bind interleukin 23 (IL-23), specifically the p19 subunit of IL-23. The invention also relates to the use of the innovative proteins in therapeutic applications to treat autoimmune diseases. The invention further relates to cells comprising such proteins, polynucleotide encoding such proteins or fragments thereof, and to vectors comprising the polynucleotides encoding the innovative proteins.

13 Claims, 33 Drawing Sheets

(56) References Cited

OTHER PUBLICATIONS

Mayfield, et al., "Expression and assembly of a fully active antibody in algae", PNAS, vol. 100, No. 2, pp. 438-442 (2003).

Parham, et al., "A Receptor for the Heterodimeric Cytokine IL-23 is Composed of IL-12Rβ1 and a Novel Cytokine Receptor Subunit, IL23R", J. Immunol., vol. 168, pp. 5699-5708 (2002).

Roberts, et al., "RNA-peptide fusions for the in vitro selection of peptides and proteins", PNAS, vol. 94, pp. 12297-12302 (1997).

Sharp, et al., "Synonymous Codon Usage in *Sacoharomycos cerevisiae*", Yeast, vol. 7, pp. 657-678 (1991).

Sinclair, et al., "Synonymous codon usage bias and the expression of human glucocerebrosidase in the methylotrophic yeast, *Pichia pastoris*", Protein Expression Purific., vol. 26, pp. 96-105 (2002).

Xu, et al., "Directed Evolution of High-Affinity Antibody Mimics Using mRNA Display", Chem. Biol., vol. 9, pp. 933-942 (2002).

Yaniv, Moshe, "Enhancing elements for activation of eukaryotic promoters", Nature, vol. 297, pp. 17-18 (1982).

Zheng, et al., "Interleukin-22, a $T_H17$ cytokine, mediates IL-23-induced dermal inflammation and acanthosis", vol. 445, pp. 648-651 (2007).

Aliahmadi, et al., "TLR2-activated human langerhans cells promote Th17 polarization via IL-1β, TGF-β and IL-23", Eur. J. Immunol, vol. 39, pp. 1221-1230 (2009).

Koide, et al. "Antibody Mimics Based on the Scaffold of the Fibronectin Type III Domain", Methods Molec. Biol., vol. 352, pp. 95-109 (2007).

Tan, et al., "Interleukin-23: Immunological roles and clinical implications", Inter. J. Biochem. Cell Biol., vol. 41, pp. 733-735 (2009).

FIG. 1

1434A08 (SEQ ID NO:216)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTCATCGTACTCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1437G04 (SEQ ID NO:217)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTTACTACCATTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1437A09 (SEQ ID NO:218)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTTCTAAACAGCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1438E05 (SEQ ID NO:219)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTTCTAACGTTCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1438D01 (SEQ ID NO:220)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTAACCGTGCTCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1438B02 (SEQ ID NO:221)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTCGTAAACTTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1438A09 (SEQ ID NO:222)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTTCTAAACAGCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

FIG. 1 (continued)

1486G03(SEQ ID NO:223)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTTCTCGTTACTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1486C04(SEQ ID NO:224)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTCCGCATCGTTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1486D04(SEQ ID NO:225)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTCGTTCTACTCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1486B05(SEQ ID NO:226)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTTCTCGTATCTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1486D05(SEQ ID NO:227)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTCATCAGCGTTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1487C03(SEQ ID NO:228)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTAAACAGGTTTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1487G03(SEQ ID NO:229)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTGCTCATCGTTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

FIG. 1 (continued)

1487D09(SEQ ID NO:230)
ATGGGAGTTTCTGATGTGCCGCGCGACCTGGAAGTGGTTGCTGCCACCCCCACCAGCCTGCTGATCAG
CTGGGGTCATTACCCGATGCATATTCGATATTACCGCATCACTTACGGCGAAACAGGAGGCAATAGCC
CTGTCCAGGAGTTCACTGTGCCTCGTTCTCGTCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1487H04(SEQ ID NO:231)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTGCTCGTCAGTACACAGCTACCATCAGCGGCCTTAAACCTGGCGTT
GATTATACCATCACTGTGTATGCTGTCACTTACTACCAGGAATACGAATACCGTTACATACCAATTTC
CATTAATTACCGCACAGAAATTGACAAACCATCCCAGCACCATCACCACCACCACTGA

1490E02(SEQ ID NO:232)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTCGTACTCAGTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1490G02(SEQ ID NO:233)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTCCGCGTTACCATACAGCTACCATCAGCGGCCTTAAACCTGGCGTT
GATTATACCATCACTGTGTATGCTGTCACTTACTACATGGAAGAAAATACGCTGTTATCCCAATTTC
CATTAATTACCGCACAGAAATTGACAAACCATCCCAGCACCATCACCACCACCACTGA

1490H05(SEQ ID NO:234)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTATGCGTCAGCATACAGCTACCATCAGCGGCCTTAAACCTGGCGTT
GATTATACCATCACTGTGTATGCTGTCACTTACTACGCTCAGGAAAACTACAAAGAAATCCCAATTTC
CATTAATTACCGCACAGAAATTGACAAACCATCCCAGCACCATCACCACCACCACTGA

1490B03(SEQ ID NO:235)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTTCTCGTAAATACACAGCTACCATCAGCGGCCTTAAACCTGGCGTT
GATTATACCATCACTGTGTATGCTGTCACTTACTACAAAGAAGCTAACTATCGTGAAATCCCAATTTC
CATTAATTACCGCACAGAAATTGACAAACCATCCCAGCACCATCACCACCACCACTGA

1490H06(SEQ ID NO:236)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTCGTCAGAAATACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

FIG. 1 (continued)

1490A07(SEQ ID NO:237)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTCATGCTAAATACACAGCTACCATCAGCGGCCTTAAACCTGGCGTT
GATTATACCATCACTGTGTATGCTGTCACTTACTACGCTCAGGAAAACTACAAAGAAATCCCAATTTC
CATTAATTACCGCACAGAAATTGACAAACCATCCCAGCACCATCACCACCACCACTGA

1490C07(SEQ ID NO:238)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTTCTAACCGTTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1490H08(SEQ ID NO:239)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTAACACTTCTCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACGGAAATTGACAAACCATCCCAGCACCATCACCACCACCACTGA

1491A05(SEQ ID NO:240)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTTCTCAGGTTTACACAGCTACCATCAGCGGCCTTAAACCTGGCGTT
GATTATACCATCACTGTGTATGCTGTCACTTACTACGCTCAGGAAAACTACAAAGAAATCCCAATTTC
CATTAATTACCGCACAGAAATTGACAAACCATCCCAGCACCATCACCACCACCACTGA

1571H03(SEQ ID NO:241)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTAACCGTGTTTACACAGCTACCATCAGCGGCCTTAAACCTGGCGTT
GATTATACCATCACTGTGTATGCTGTCACTTACTACGCTCAGGAAGAATACCATATCATCCCAATTTC
CATTAATTACCGCACAGAAATTGACAAACCATCCCAGCACCATCACCACCACCACTGA

1571G04(SEQ ID NO:242)
ATGGGAGTTTCTGATGTGCCSCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTCCGCGTTCTCACACAGCTACCATCAGCGGCCTTAAACCTGGCGTT
GATTATACCATCACTGTGTATGCTGTCACTTACTACGCTCAGGAAAACTACAAAGAAATCCCAATTTC
CATTAATTACCGCACAGAAATTGACAAACCATCCCAGCACCATCACCACCACCACTGA

1571G06(SEQ ID NO:243)
ATGGGAGTTTCTGATGTGCCGCGCGACCTGGAAGTGGTTGCTGCCACCCCCACCAGCCTGCTGATCAG
CTGGGGTCATTACCCGCTGCACCTGCGATATTACCGCATCACTTACGGCGAAACAGGAGGCAATAGCC
CTGTCCAGGAGTTCACTGTGCCTCGTACTAAATACACAGCTACCATCAGCGGCCTTAAACCTGGCGTT
GATTATACCATCACTGTGTATGCTGTCACTTACTACAAAGAAGCTGACTACTCTCAGATCCCAATTTC
CATTAATTACCGCACAGAAATTGACAAACCATCCCAGCACCATCACCACCACCACTGA

FIG. 1 (continued)

1571F10(SEQ ID NO:244)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTTCTCGTTACCATACAGCTACCATCAGCGGCCTTAAACCTGGCGTT
GATTATACCATCACTGTGTATGCTGTCACTTACTACGAACAGGTTGAATACCGTGAAATCCCAATTTC
CATTAATTACCGCACAGAAATTGACAAACCATCCCAGCACCATCACCACCACCACTGA

1572D04(SEQ ID NO:245)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTCCGCGTCGTTACACAGCTACCATCAGCGGCCTTAAACCTGGCGTT
GATTATACCATCACTGTGTATGCTGTCACTTACTACGAACAGCCGATCTACGCCACTATCCCAATTTC
CATTAATTACCGCACAGAAATTGACAAACCATCCCAGCACCATCACCACCACCACTGA

1572F05(SEQ ID NO:246)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTCGTCAGAAATACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1572G06(SEQ ID NO:247)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTCGTTACAAATACACAGCTACCATCAGCGGCCTTAAACCTGGCGTT
GATTATACCATCACTGTGTATGCTGTCACTTACTACGCTCAGGAAAACTACAAAGAAATCCCAATTTC
CATTAATTACCGCACAGAAATTGACAAACCATCCCAGCACCATCACCACCACCACTGA

1572B10(SEQ ID NO:248)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTGTTCCGCGTCATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1572C09(SEQ ID NO:249)
ATGGGAGTTTCTGATGTGCCGCGCGACCTGGAAGTGGTTGCTGCCACCCCCACCAGCCTGCTGATCAG
CTGGGGTCATTACCCGATGCATATCCGATATTACCGCATCACTTACGGCGAAACAGGAGGCAATAGCC
CTGTCCAGGAGTTCACTGTGCCTACTCCGAAACATACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1572H05(SEQ ID NO:250)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTCGTTCTAAATACACAGCTACCATCAGCGGCCTTAAACCTGGCGTT
GATTATACCATCACTGTGTATGCTGTCACTTACTACGAACAGGTTGAATACCGTGAAATCCCAATTTC
CATTAATTACCGCACAGAAATTGACAAACCATCCCAGCACCATCACCACCACCACTGA

FIG. 1 (continued)

1572H08(SEQ ID NO:251)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTTCTCGTAAATACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1550A07(SEQ ID NO:252)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTGTTCCGCGTTACACAGCTACCATCAGCGGCCTTAAACCTGGCGTT
GATTATACCATCACTGTGTATGCTGTCACTTACTACGCTCAGGAAAACTACAAAGAAATCCCAATTTC
CATTAATTACCGCACAGAAATTGACAAACCATCCCAGCACCATCACCACCACCACTGA

1550C05(SEQ ID NO:253)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTCCGCGTCGTTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

1550E03(SEQ ID NO:254)
ATGGGAGTTTCTGATGTGCCGCGCGACCTGGAAGTGGTTGCTGCCACCCCCACCAGCCTGCTGATCAG
CTGGGGTCATTACCCGCTGCATATCCGATATTACCGCATCACTTACGGCGAAACAGGAGGCAATAGCC
CTGTCCAGGAGTTCACTGTGCCTCGTATGCGTCATACAGCTACCATCAGCGGCCTTAAACCTGGCGTT
GATTATACCATCACTGTGTATGCTGTCACTTACTACTCCGAAGAACTGTACAAATACATCCCAATTTC
CATTAATTACCGCACAGAAATTGACAAACCATCCCAGCACCATCACCACCACCACTGA

1550E06(SEQ ID NO:255)
ATGGGAGTTTCTGATGTGCCGCGCGACCTGGAAGTGGTTGCTGCCACCCCCACCAGCCTGCTGATCAG
CTGGGGTCATTACCCGATGCATGTTCGATATTACCGCATCACTTACGGCGAAACAGGAGGCAATAGCC
CTGTCCAGGAGTTCACTGTGCCTCCGCCGCGTCATACCGCTACCATCAGCGGCCTTAAACCTGGCGTT
GATTATACCATCACTGTGTATGCTGTCACTTACTACGCTCAGGAAAACTACAAAGAAATCCCAATTTC
CATTAATTACCGCACAGAAATTGACAAACCATCCCAGCACCATCACCACCACCACTGA

1550H05(SEQ ID NO:256)
ATGGGAGTTTCTGATGTGCCGCGCGACCTGGAAGTGGTTGCTGCCACCCCCACCAGCCTGCTGATCAG
CTGGGGTCATTACCCGCTGCATGTTCGATATTACCGCATCACTTACGGCGAAACAGGAGGCAATAGCC
CTGTCCAGGAGTTCACTGTGCCTCGTCAGATCTACACAGCTACCATCAGCGGCCTTAAACCTGGCGTT
GATTATACCATCACTGTGTATGCTGTCACTTACTACAACGAAGCTGACTACTCTCAGATCCCAATTTC
CATTAATTACCGCACAGAAATTGACAAACCATCCCAGCACCATCACCACCACCACTGA

```
1572B10  VSDVPRDLEVVAATPTSLLISWGHYPMHVRYYRITYGETGGNSPVQEFTVPVPRHTATISGLKPGVDYTITVYAVTYYNEADYSQIPISINYRT
1572C09  VSDVPRDLEVVAATPTSLLISWGHYPMHIRYYRITYGETGGNSPVQEFTVPTPKHTATISGLKPGVDYTITVYAVTYYNEADYSQIPISINYRT
1572H05  VSDVPRDLEVVAATPTSLLISWGHYPLHIRYYRITYGETGGNSPVQEFTVPRSKYTATISGLKPGVDYTITVYAVTYYEQVEYREIPISINYRT
1572H08  VSDVPRDLEVVAATPTSLLISWGHYPLHVRYYRITYGETGGNSPVQEFTVPSRKYTATISGLKPGVDYTITVYAVTYYNEADYSQIPISINYRT
1550A07  VSDVPRDLEVVAATPTSLLISWGHYPMHVRYYRITYGETGGNSPVQEFTVPVPRYTATISGLKPGVDYTITVYAVTYYAQENYKEIPISINYRT
1550C05  VSDVPRDLEVVAATPTSLLISWGHYPMHVRYYRITYGETGGNSPVQEFTVPPRRYTATISGLKPGVDYTITVYAVTYYNEADYSQIPISINYRT
1550E03  VSDVPRDLEVVAATPTSLLISWGHYPLHIRYYRITYGETGGNSPVQEFTVPRMRHTATISGLKPGVDYTITVYAVTYYSEELYKYIPISINYRT
1550E06  VSDVPRDLEVVAATPTSLLISWGHYPMHVRYYRITYGETGGNSPVQEFTVPPPRHTATISGLKPGVDYTITVYAVTYYAQENYKEIPISINYRT
1550H05  VSDVPRDLEVVAATPTSLLISWGHYPLHVRYYRITYGETGGNSPVQEFTVPRQIYTATISGLKPGVDYTITVYAVTYYNEADYSQIPISINYRT
```

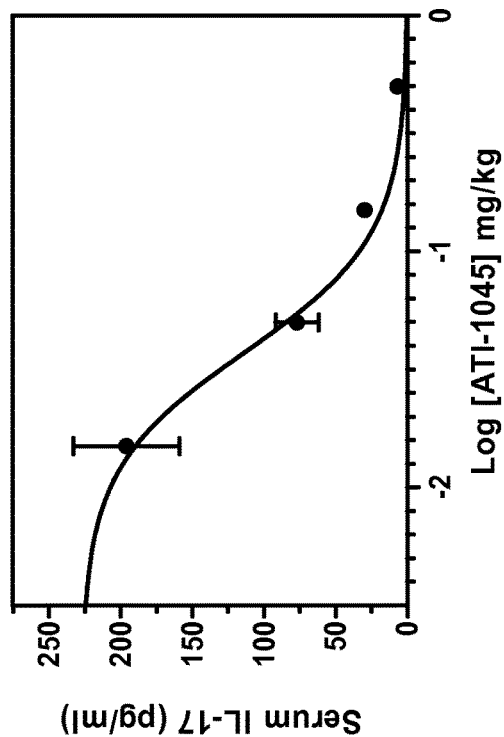
FIG. 9A
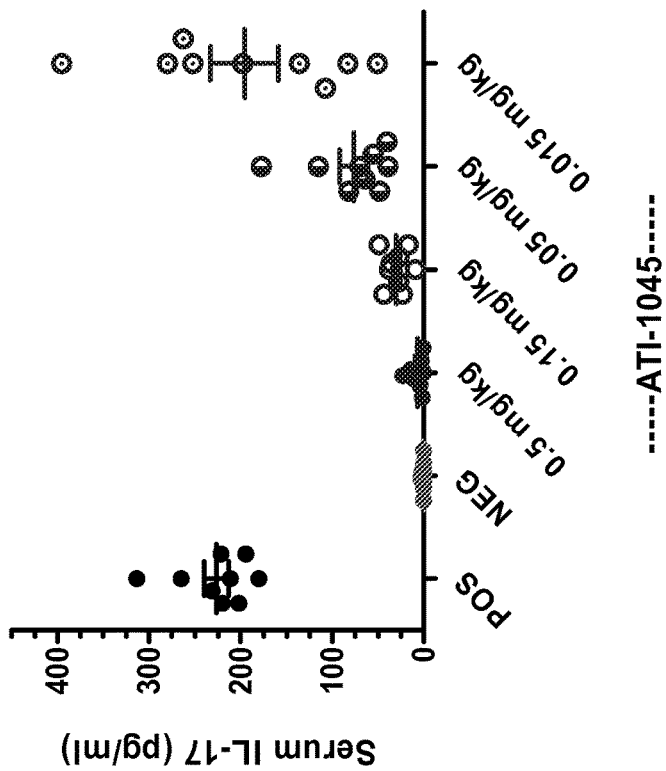

Determination of HSA *in vivo* half-life in mice 20 mg/kg 50 mg/kg

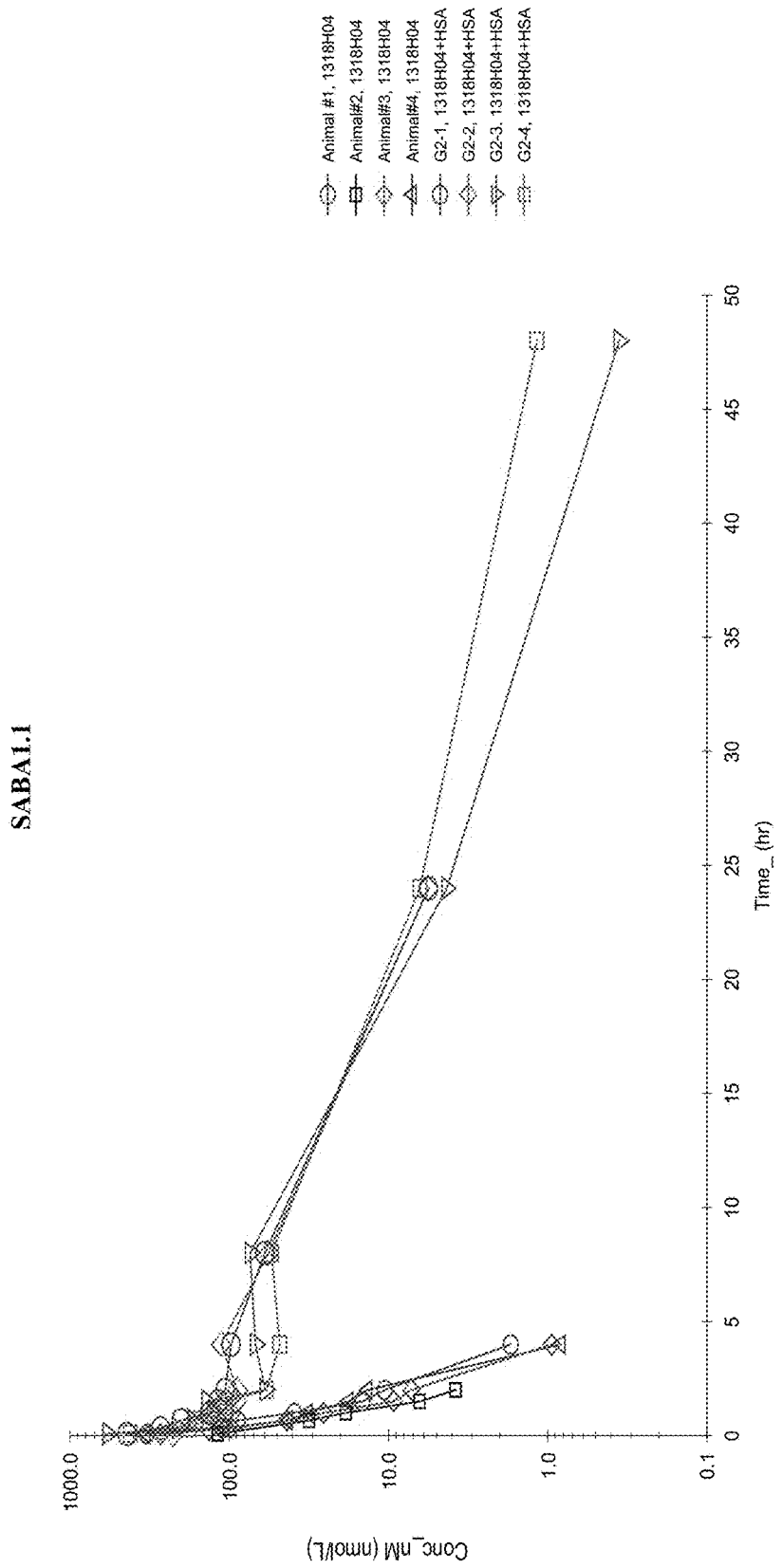

SABA2.1

SABA3.1

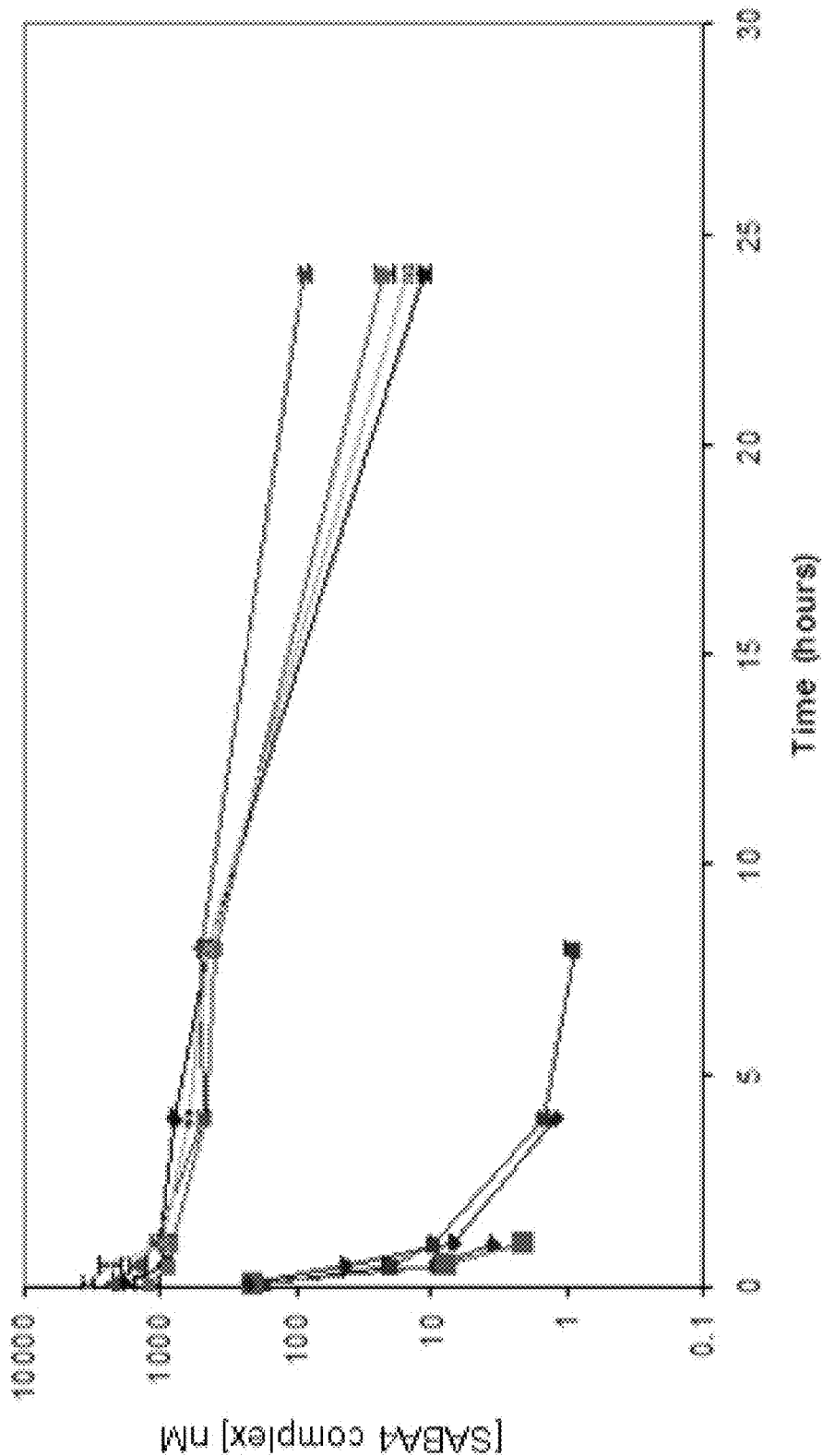
FIG. 12D SABA4.1

FIG. 13B.

| CLONE | PK (T1/2) | | Comments |
|---|---|---|---|
| | Mice | Cyno | |
| SABA1.1 | 5.6hrs | 96-137hrs | T1/2 = 96-137hrs |
| SABA5.1 | 4.6hrs | 12hrs | Poor binding affinity for RhSA. 2-fold decrease in KD observed at pH<6.0 |
| SABA2.1 | 2.8hrs | NA | Loss of binding at pH <6.5 |
| SABA3.1 | 32min | NA | Poor T1/2 observed in mice |

SABA1.1 and SABA5.1 $t_{1/2}$ in Cynomolgus monkey

SABA5.1

SABA1.2 binding to albumins from human, mouse and rat by direct binding ELISA assay SABA1.1 binds to HSA with 1:1 stoichiometry

FIG. 17

Biacore Analysis of SABA1.2 Binding to Recombinant Domain Fragments of HSA

HA1 binding to HuSA domains

- ▓ 100 nM
- ■ 1000 nM x-axis: Binding level (RU), from -10 to 130

Categories: HuSA, HuSA domain III, HuSA domain I & III

Pharmacokinetic Profile for SABA1.2 in Monkeys Dosed at 1mpk and 10mpk

Pharmacokinetic Profile for SABA1.2 in Monkeys Dosed Intravenously or Subcutaneously at 1mpk

FIBRONECTIN BASED SCAFFOLD DOMAIN PROTEINS THAT BIND IL-23

This application is a continuation of U.S. application Ser. No. 13/579,204, filed Aug. 15, 2012, now allowed, which is the 371 National Stage of International Application No. PCT/US2011/024959, filed Feb. 16, 2011, which claims the benefit of U.S. Provisional Application No. 61/305,566, filed Feb. 18, 2010, now abandoned and U.S. Provisional Application No. 61/330,706, filed May 3, 2010, now abandoned. The contents of all of the foregoing applications in their entireties are incorporated by reference into the present application.

FIELD OF THE INVENTION

The present invention relates to fibronectin based scaffold domain protein that bind interleukin 23 (IL-23), specifically the p19 subunit of IL-23. The invention also relates to the use of the innovative proteins in therapeutic applications to treat autoimmune diseases. The invention further relates to cells comprising such proteins, polynucleotide encoding such proteins or fragments thereof, and to vectors comprising the polynucleotides encoding the innovative proteins.

INTRODUCTION

IL-23 is a member of the IL-12 heterodimeric cytokine family. It contains the p40 subunit, which is common to IL-12, and a unique p19 subunit. IL-23 sends signals through a heterodimeric receptor complex consisting of IL-12Rβ1 and IL-23R (Aggarwal, S et al., "Interleukin-23 promotes a distinct CD4 T cell activation state characterized by the production of interleukin-17", *J. Biol. Chem.*, 278: 1910-1914 (2003)). IL-23 is a potential target for the treatment of chronic inflammatory disorders such as multiple sclerosis, rheumatoid arthritis, psoriasis and Crohn's disease.

Fibronectin based scaffolds are a family of proteins capable of evolving to bind any compound of interest. These proteins, which generally make use of a scaffold derived from a fibronectin type III (Fn3) or Fn3-like domain, function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins are Adnectins (Adnexus, a Bristol-Myers Squibb R&D Company).

Fibronectin type III (Fn3) domains comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. Any or all of loops AB, BC, CD, DE, EF and FG may participate in target binding. The BC, DE, and FG loops are both structurally and functionally analogous to the complementarity determining regions (CDRs) from immunoglobulins. U.S. Pat. No. 7,115,396 describes Fn3 domain proteins wherein alterations to the BC, DE, and FG loops result in high affinity TNFα binders. U.S. Publication No. 2007/0148126 describes Fn3 domain proteins wherein alterations to the BC, DE, and FG loops result in high affinity VEGFR2 binders.

It would be advantageous to obtain improved fibronectin domain scaffold proteins for therapeutic treatment of autoimmune disorders. A subset of effector T cells that produce interleukin 17 (IL-17; "Th17 cells") are highly proinflammatory and induce severe autoimmunity. Th17 cells express a distinct subset of cytokines and chemokines compared to Th1 and Th2 cells, including IL-6, tumor necrosis factor (TNF), IL-22, IL-17A and IL-17F as well as the chemokine receptor CCR6. IL-23 promotes the production of IL-17 by activated T cells (Aggarwal, S et al., "Interleukin-23 promotes a distinct CD4 T cell activation state characterized by the production of interleukin-17", *J. Biol. Chem.*, 278:1910-1914 (2003)) and is a key cytokine to induce expansion of IL-17-producing CD4+ T cells. Exposure to IL-23 seems to be the key feature that determines the pathogenicity of Th17 cells.

SUMMARY OF THE INVENTION

The application provides Adnectins™ against human IL-23-specific p19 subunit. One aspect of the invention provides for polypeptides comprising Fn3 domain in which one or more of the solvent accessible loops has been randomized or mutated. In some embodiments, the Fn3 domain is a Fn3 domain derived from the wild-type tenth module of the human fibronectin type III domain ($^{10}$Fn3). In some embodiments, the $^{10}$Fn3 polypeptide of the invention is at least 40%, 50%, 60%, 65%, 70%, 75%, 80%, 85%, or 90% identical to the human $^{10}$Fn3 domain.

In some embodiments, one or more loops selected from BC, DE, and FG may be extended or shortened in length relative to the corresponding human fibronectin loop.

In some embodiments, the polypeptides of the invention comprises a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain.

In some embodiments, the polypeptide of the invention comprises a Fn3 domain that comprises an amino acid sequence at least 80, 85, 90, 95, 98, 99 or 100% identical to the non-loop regions.

In some embodiments, the BC loop of the protein of the invention comprises an amino acid sequence selected from the group consisting of SEQ ID NOs: 2-6.

In some embodiments, the DE loop of the protein of the invention comprises an amino acid sequence selected from the group consisting of SEQ ID NOs: 7-48.

In some embodiments, the FG loop of the protein of the invention comprises an amino acid sequence selected from the group consisting of SEQ ID NOs: 49-59.

In some embodiments, the $^{10}$Fn3 domain may begin and/or end with amino acid substitutions, insertions or deletions.

In some embodiments, the protein of the invention comprises one loop sequence from the BC loop sequences shown in SEQ ID NOs: 2-6, one DE loop sequence shown in SEQ ID NOs: 7-48 and one FG loop sequence shown in SEQ ID NOs: 49-59.

In some embodiments, the protein of the invention comprises a BC, DE and FG loop amino acid sequence at least 70, 75, 80, 85, 90, 95, 98, 99 or 100% identical to of any one of SEQ ID NOS:2-59.

In some embodiments, the anti-IL-23 Adnectin comprises the amino acid sequence of any one of SEQ ID NOS:60-100.

In some embodiments, the anti-IL-23 Adnectin comprises the Fn3 domain amino acid sequence from position 3-96 of any one of SEQ ID NOS:60-100.

In some embodiments, the anti-IL-23 Adnectin comprises the amino acid sequence at least 70, 75, 80, 85, 90, 95, 98, 99 or 100% identical to of any one of SEQ ID NOS:60-100.

In one aspect, the anti-IL-23 Adnectin further comprising a pharmacokinetic (PK) moiety. In some embodiments, the PK moiety comprises polyethylene glycol (PEG).

In one aspect, the application provides an anti-IL-23 Adnectin useful in the treatment of autoimmune diseases.

In one aspect, the present invention provides a fusion polypeptide comprising a fibronectin type III tenth ($^{10}$Fn3) domain and anti-IL-23 Adnectin, wherein the $^{10}$Fn3 domain binds to HSA with a Kd of 1 uM or less. In certain embodiments, the $^{10}$Fn3 domain comprises an amino acid sequence at least 70% identical to SEQ ID NO: 103. In one embodiment, the $^{10}$Fn3 domain comprises a BC loop having the amino acid sequence set forth in SEQ ID NO: 104, a DE loop having the amino acid sequence set forth in SEQ ID NO: 105, and an FG loop having the amino acid sequence set forth in SEQ ID NO:106. In another embodiment, the $^{10}$Fn3 domain comprises one or more of a BC loop having the amino acid sequence set forth in SEQ ID NO: 104, a DE loop having the amino acid sequence set forth in SEQ ID NO: 105, and an FG loop having the amino acid sequence set forth in SEQ ID NO: 106.

In one embodiment, the $^{10}$Fn3 domain of the fusion polypeptide also binds to one or more of rhesus serum albumin (RhSA), cynomolgus monkey serum albumin (CySA), or murine serum albumin (MuSA). In other embodiments, the $^{10}$Fn3 domain does not cross-react with one or more of RhSA, CySA or MuSA.

In certain embodiments, the $^{10}$Fn3 domain of the fusion polypeptide binds to HSA with a Kd of 1 uM or less. In some embodiments, the $^{10}$Fn3 domain binds to HSA with a Kd of 500 nM or less. In other embodiments, the $^{10}$Fn3 domain binds to HSA with a Kd of at least 200 nM, 100 nM, 50 nM, 20 nM, 10 nM, or 5 nM.

In other embodiments, the $^{10}$Fn3 domain of the fusion polypeptide binds to domain I or II of HSA. In one embodiment, the $^{10}$Fn3 domain binds to both domains I and II of HSA. In some embodiments, the $^{10}$Fn3 domain binds to HSA at a pH range of 5.5 to 7.4. In other embodiments, the $^{10}$Fn3 domain binds to HSA with a Kd of 200 nM or less at pH 5.5. In another embodiment, the $^{10}$Fn3 domain binds to HSA with a Kd of at least 500 nM, 200 nM, 100 nM, 50 nM, 20 nM, 10 nM, or 5 nM at a pH range of 5.5 to 7.4. In one embodiment, the $^{10}$Fn3 domain binds to HSA with a Kd of at least 500 nM, 200 nM, 100 nM, 50 nM, 20 nM, 10 nM, or 5 nM at pH 5.5.

In some embodiments, the serum half-life of the fusion polypeptide in the presence of serum albumin is at least 5-fold greater than the serum half-life of the polypeptide in the absence of serum albumin. In certain embodiments, the serum half-life of the fusion polypeptide in the presence of serum albumin is at least 2-fold, 5-fold, 7-fold, 10-fold, 12-fold, 15-fold, 20-fold, 22-fold, 25-fold, 27-fold, or 30-fold greater than the serum half-life of the polypeptide in the absence of serum albumin. In some embodiments, the serum albumin is any one of HSA, RhSA, CySA, or MuSA.

In certain embodiments, the serum half-life of the fusion polypeptide in the presence of serum albumin is at least 20 hours. In certain embodiments, the serum half-life of the fusion polypeptide in the presence of serum albumin is at least 10 hours, 12 hours, 15 hours, 20 hours, 25 hours, 30 hours, 40 hours, 50 hours, 75 hours, 90 hours, 100 hours, 110 hours, 120 hours, 130 hours, 150 hours, 170 hours, or 200 hours. In some embodiments, the half-life of the fusion polypeptide is observed in a primate (e.g., human or monkey) or a murine.

In any of the foregoing aspects and embodiments, the $^{10}$Fn3 domain comprises a sequence selected from SEQ ID NO: 107, 111, 115, 119, and 123-143.

BRIEF DESCRIPTION OF THE FIGURES

FIG. 1 shows the full length DNA sequence alignment of the anti-IL23 Adnectin of the invention.

FIG. 3 shows the full length amino acid sequence alignment of the anti-IL23 adnectin of the invention.

FIG. 9A shows that ATI001045 Inhibits Serum IL-17Levels in Mouse Pharmacodynamic Model as described in Example 4.

FIGS. 12A-D show the half-life determination of SABA1-SABA4 in mice.

FIG. 13b compares data from cynomolgus monkey and mice.

FIG. 17 shows Biacore analysis of SABA1.2 binding to recombinant domain fragments of HSA.

DETAILED DESCRIPTION OF THE INVENTION

Definitions

Figure 2:
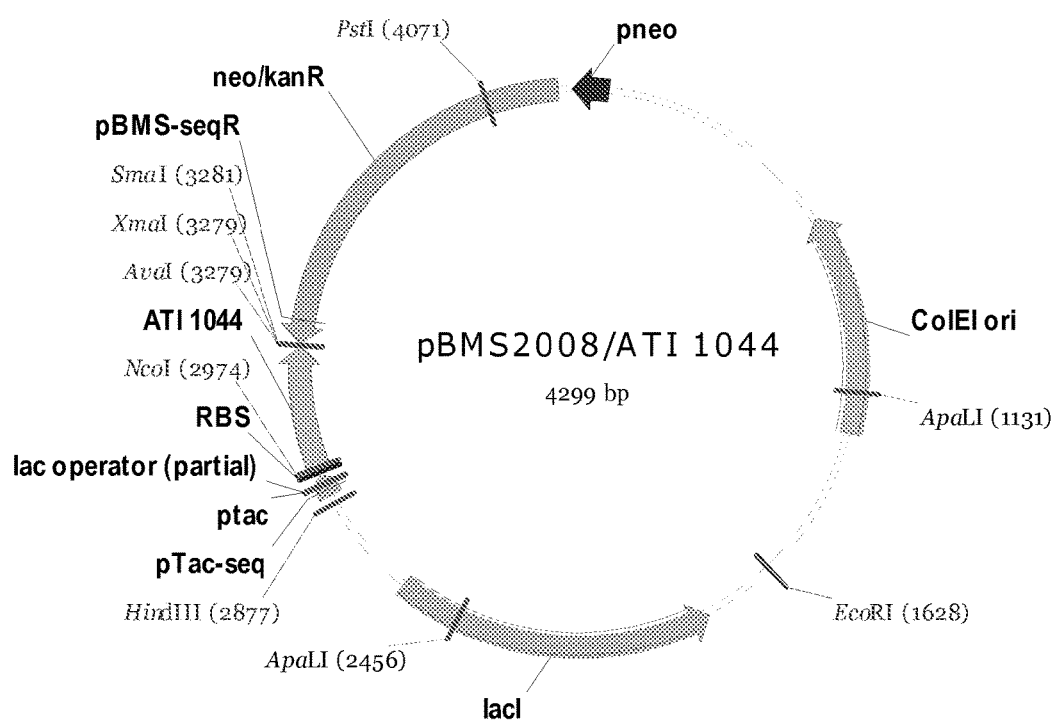
FIG. 2 shows pBMS2008/ATI001044 protein expression vector as described in Example 2.

By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D). The peptides of the invention are proteins derived from the tenth type III domain of fibronectin that have been modified to bind specifically to the p19 subunit of IL-23 and are referred to herein as "Adnectin" or "anti-IL-23 Adnectin".

The term "PK" is an acronym for "pharmokinetic" and encompasses properties of a compound including, by way of example, absorption, distribution, metabolism, and elimination by a subject. A "PK modulation protein" or "PK moiety" refers to any protein, peptide, or moiety that affects the pharmacokinetic properties of a biologically active molecule when fused to or administered together with the biologically active molecule. Examples of a PK modulation protein or PK moiety include PEG, human serum albumin (HSA) binders (as disclosed in U.S. Publication Nos. 2005/0287153 and 2007/0003549), human serum albumin, Fc or Fc fragments, and sugars (e.g., sialic acid).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR®) software. Those skilled in the art can determine appropriate parameters for measuring alignment, including any algorithms needed to achieve maximal alignment over the full-length of the sequences being compared.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or nonreducing condition using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

The "half-life" of an amino acid sequence or compound can generally be defined as the time taken for the serum concentration of the polypeptide to be reduced by 50%, in vivo, for example due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may for example generally involve the steps of suitably administering to the primate a suitable dose of the amino acid sequence or compound of the invention; collecting blood samples or other samples from said primate at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Reference is for example made to the standard handbooks, such as Kenneth, A. et al., *Chemical Stability of Pharmaceuticals: A Handbook for Pharmacists* and in Lee, P. I. D. et al., *Pharmacokinetic Analysis: A Practical Approach* (1996). Reference is also made to Gibaldi, M. et al., *Pharmacokinetics,* 2nd Rev. Edition, Marcel Dekker, publ. (1982).

Half-life can be expressed using parameters such as the t½-alpha, t½-beta and the area under the curve (AUC). In the present specification, an "increase in half-life" refers to an increase in any one of these parameters, any two of these parameters, or all three these parameters. An "increase in half-life" in particular refers to an increase in the t½-beta, either with or without an increase in the t½-alpha and/or the AUC or both.

Overview

The application provides Adnectins against human IL-23-specific p19 subunit. In order to identify IL-23 specific antagonist, IL-23 was presented to large synthetic libraries of Adnectin using anti-p40 mAbs. Adnectins that bound to IL-23 p19 subunit were screened for binding to human IL-23, competition of the IL-23/IL-23R interaction and inhibition of IL-23 induced signaling in a T-cell line. The anti-IL-23 Adnectins were subjected to further selective pressure by lowering the target concentration and selecting for anti-IL-23 Adnectins with slow off-rates. From this optimization process a family of Adnectins were identified as IL-23 specific inhibitors with favorable biochemical and biophysical properties.

Fibronectin Based Scaffolds

One aspect of the application provides for polypeptides comprising Fn3 domain in which one or more of the solvent accessible loops has been randomized or mutated. In some embodiments, the Fn3 domain is an Fn3 domain derived from the wild-type tenth module of the human fibronectin type III domain($^{10}$Fn3):
VSDVPRDLEVVAATPTSLLI
<u>SWDAPAVTVRYYRITYGETGGNSPVQEFTV</u>
PGSKST,ATISGLKPGVDYTITVYAVT
<u>GRGDSPASSKPISINYRT</u> (SEQ ID NO: 1). In the $^{10}$Fn3 sequence above, the BC, DE and FG loops are underlined.

A variety of mutant $^{10}$Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO02/04523). A variety of additional alterations in the $^{10}$Fn3 scaffold that are either beneficial or neutral have been disclosed. See, for example, Batori et al., *Protein Eng.*, 15(12):1015-1020 (December 2002); Koide et al., *Biochemistry*, 40(34):10326-10333 (Aug. 28, 2001).

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO:1, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87 (Xu et al., *Chemistry & Biology*, 9:933-942 (2002)).

In some embodiments, the $^{10}$Fn3 polypeptide may be at least 40%, 50%, 60%, 65%, 70%, 75%, 80%, 85%, or 90% identical to the human $^{10}$Fn3 domain, shown in SEQ ID NO:1. Much of the variability will generally occur in one or more of the loops. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO:1, provided that such variation does not disrupt the stability of the polypeptide in physiological conditions.

In some embodiments, the disclosure provides polypeptides comprising a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain. In some embodiments, the BC and FG loops are altered, in some embodiments, the BC, DE, and FG loops are altered, i.e., the Fn3 domains comprise non-naturally occurring loops. By "altered" is meant one or more amino acid sequence alterations relative to a template sequence (corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In some embodiments, one or more loops selected from BC, DE, and FG may be extended or shortened in length relative to the corresponding human fibronectin loop. In some embodiments, the length of the loop may be extended by 2-25 amino acids. In some embodiments, the length of the loop may be decreased by 1-11 amino acids. To optimize antigen binding, therefore, the length of a loop of $^{10}$Fn3 may be altered in length as well as in sequence to obtain the greatest possible flexibility and affinity in antigen binding.

In some embodiments, the polypeptide comprises a Fn3 domain that comprises an amino acid sequence at least 80, 85, 90, 95, 98, 99 or 100% identical to the non-loop regions of SEQ ID NO:1, wherein at least one loop selected from BC, DE, and FG is altered. In some embodiments, the altered BC loop has up to 10 amino acid substitutions, up to 4 amino acid deletions, up to 10 amino acid insertions, or a combination thereof. In some embodiments, the altered DE loop has up to 6 amino acid substitutions, up to 4 amino acid deletions, up to 13 amino acid insertions or a combination thereof. In some embodiments, the FG loop has up to 12 amino acid substitutions, up to 11 amino acid deletions, up to 25 amino acid insertions or a combination thereof.

In some embodiments, the BC loop of the protein of the invention comprises an amino acid sequence selected from the group consisting of GHYPMHV (SEQ ID NO: 2), GHYPLHV (SEQ ID NO: 3), GHYPMHI (SEQ ID NO:4), GHYPLHI (SEQ ID NO:5) and GHYPLHL (SEQ ID NO:6).

In some embodiments, the DE loop of the protein of the invention comprises an amino acid sequence selected from the group consisting of HRTH(SEQ ID NO:7), YYHY(SEQ ID NO:8), SKQH (SEQ ID NO:9), SNVH (SEQ ID NO:10), NRAH (SEQ ID NO:11), RKTY(SEQ ID NO:12), RSRY (SEQ ID NO:13), SRYY (SEQ ID NO:14), PHRY (SEQ ID NO:15), RSTH (SEQ ID NO:16), SRIY (SEQ ID NO:17), HQRY (SEQ ID NO:18), KQVY (SEQ ID NO:19), AHRY (SEQ ID NO:20), RSRH (SEQ ID NO:21), ARQY (SEQ ID NO:22), RTQY (SEQ ID NO:23), PRYH (SEQ ID NO:24), MRQH (SEQ ID NO:25), SRKY (SEQ ID NO:26), RQKY (SEQ ID NO:27), HAKY(SEQ ID NO:28), SNRY (SEQ ID NO:29), NTSH (SEQ ID NO:30), SQVY (SEQ ID NO:31), NRVY (SEQ ID NO:32), PRSH (SEQ ID NO:33), RTKY (SEQ ID NO:34), SRYH (SEQ ID NO:35), PRRY(SEQ ID NO:36), RQKY (SEQ ID NO:37), RYKY (SEQ ID NO:38), VPRH (SEQ ID NO:39), TPKH (SEQ ID NO:40), RSKY (SEQ ID NO:41), SRKY (SEQ ID NO:42), VPRY (SEQ ID NO:43), PRRY (SEQ ID NO:44), RMRH (SEQ ID NO:45), PPRH (SEQ ID NO:46), RQIY (SEQ ID NO:47), and MRQH(SEQ ID NO:48).

In some embodiments, the FG loop of the protein of the invention comprises an amino acid sequence selected from the group consisting of YYNEADYSQI (SEQ ID NO:49), YYQEYEYRYI (SEQ ID NO:50), YYMEEKYAVI (SEQ ID NO:51), YYAQENYKEI (SEQ ID NO:52), YYKEANYREI (SEQ ID NO:53), YYAQEEYHII (SEQ ID NO:54), YYKEADYSQI (SEQ ID NO:55), YYEQVEYREI (SEQ ID NO:56), YYEQPIYATI (SEQ ID NO:57), YYEQVEYREI (SEQ ID NO:58) and YYSEELYKYI (SEQ ID NO:59).

The $^{10}$Fn3 domain may begin with amino acid alterations. For example, an additional MG sequence may be placed at the N-terminus of an Fn3 domain. The M will usually be cleaved off, leaving a G at the N-terminus In some embodiments, sequences may be placed at the C-terminus of the $^{10}$Fn3 domain. For example, in site directed PEGylation where a cysteine containing linker such as GSGC (SEQ ID NO: 101) is added to the C-terminus. Alternatively, PEGylation of the naturally occurring C-terminus tail that has been mutated by changing the Ser to a Cys for a cysteine containing linker EIDKPCQ (SEQ ID NO: 102). Examples of the anti-IL-23 adnectin of the invention comprising the GSGC linker include ATI001014, ATI001015, ATI001016, ATI001044, ATI001045 and ATI001047. ATI000934 is an example of the anti-Il-23 adnectin of the invention comprising the EIDKPCQ linker.

In some embodiments, the protein of the invention comprises one loop sequence from the BC loop sequences shown in SEQ ID NOs: 2-6, one DE loop sequence shown in SEQ ID NOs: 7-48 and one FG loop sequence shown in SEQ ID NOs: 49-59. In some embodiments, the protein of the invention comprises a BC, DE and FG loop amino acid sequence at least 70, 75, 80, 85, 90, 95, 98, 99 or 100% identical to of any one of SEQ ID NOS:2-59.

Further, one skilled in the art will recognize that BC loop sequences shown in SEQ ID NO: 2-6 share a common sequence motif GHYPX$_1$HX$_2$ (SEQ ID NO:257) where X$_1$ is either M or L, and X$_2$ is either I or V, and the FG loop sequences shown in SEQ ID NO: 49-59 share a common sequence motif YYX$_3$X$_3$X$_3$X$_3$YX$_3$X$_3$I (SEQ ID NO: 258) where X$_3$ can be any amino acid. It would therefore be possible to generate additional Adnectins that bind IL-23 with BC loops that fit the consensus sequence GHYPX$_1$HX$_2$ and/or with other FG loops, beyond those explicitly listed in SEQ ID NOS:49-59, that fit the pattern YYX$_3$X$_3$X$_3$X$_3$YX$_3$X$_3$I.

In some embodiments, the anti-IL-23 Adnectin comprises the amino acid sequence of any one of SEQ ID NOS:60-100. In some embodiments, the anti-IL-23 Adnectin comprises the Fn3 domain amino acid sequence from position 3-96 of any one of SEQ ID NOS:60-100. In some embodiments, the anti-IL-23 Adnectin comprises the amino acid sequence at least 70, 75, 80, 85, 90, 95, 98, 99 or 100% identical to any one of SEQ ID NOS: 60-100. In some embodiments, the anti-IL-23 Adnectin comprises the amino acid sequence at least 70, 75, 80, 85, 90, 95, 98, 99 or 100% identical to amino acid sequence from position 3-96 any one of SEQ ID NOS:60-100.

In some embodiments, the anti-IL-23 Adnectin may be pegylated and/or contain a his-tag. As used herein, ATI000934 refers to a protein wherein the loop sequences are identical to those of construct 1571G06 (Seq ID 87), and the protein contains the residues EIDKPCQ at the C-terminus where the protein is pegylated and contains a his-tag. ATI001014 refers to a protein wherein the loop sequences are identical to those of construct 1571G04 (Seq ID 86), and the protein contains a GSGC linker at the C-terminus where the protein is pegylated and contains a his-tag. ATI001015 refers to a protein wherein the loop sequences are identical to those of construct 1572G06 (Seq ID 91), and the protein contains a GSGC linker at the C-terminus where the protein is pegylated and contains a his-tag. ATI001016 refers to a protein wherein the loop sequences are identical to those of construct 1490B03 (Seq ID 79), and the protein contains a GSGC linker at the C-terminus where the protein is pegylated and contains a his-tag. ATI001044 refers to a protein wherein the loop sequences are identical to those of construct1490B03 (Seq ID 79), and the protein contains a GSGC linker at the C-terminus, but protein is not pegylated and there is no his tag. ATI001045 refers to a protein wherein the loop sequences are identical to those of construct 1490B03 (Seq ID 79), and the protein contains a GSGC linker at the C-terminus where the protein is pegylated; and there is no his tag. ATI001047 refers to a protein wherein the loop sequences are identical to those of construct 1571G04 (Seq ID 86), and the protein contains a GSGC linker at the C-terminus where the protein is pegylated, and there is no his tag Fibronectin naturally binds certain types of integrins through its integrin-binding motif, "arginine-glycine-aspartic acid" (RGD). In some embodiments, the polypeptide comprises a $^{10}$Fn3 domain that lacks the (RGD) integrin binding motif.

Pharmacokinetic Moieties

In one aspect, the application provides for anti-IL-23 Adnectin further comprising a pharmacokinetic (PK) moiety. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The anti-IL-23 Adnectin may be attached to a moiety that reduces the clearance rate of the polypeptide in a mammal (e.g., mouse, rat, or human) by greater than three-fold relative to the unmodified Adnectin. Other measures of improved pharmacokinetics may include serum half-life, which is often divided into an alpha phase and a beta phase. Either or both phases may be improved significantly by addition of an appropriate moiety.

Moieties that tend to slow clearance of a protein from the blood, herein referred to as "PK moieties", include polyoxyalkylene moieties, e.g., polyethylene glycol, sugars (e.g., sialic acid), and well-tolerated protein moieties (e.g., Fc, Fc fragments, transferrin, or serum albumin). The Adnectin may be fused to albumin or a fragment (portion) or variant of albumin as described in U.S. Publication No. 2007/0048282.

In some embodiments, the PK moiety is a serum albumin binding protein such as those described in U.S. Publication Nos. 2007/0178082 and 2007/0269422.

In some embodiments, the PK moiety is a serum immunoglobulin binding protein such as those described in U.S. Publication No. 2007/0178082.

In some embodiments, the Adnectin comprises polyethylene glycol (PEG). One or more PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus Pegylation may be achieved by site-directed pegylation, wherein a suitable reactive group is introduced into the protein to create a site where pegylation preferentially occurs. In some embodiments, the protein is modified to introduce a cysteine residue at a desired position, permitting site directed pegylation on the cysteine. PEG may vary widely in molecular weight and may be branched or linear.

In some embodiments, the Adnectin comprises an Fn3 domain and a PK moiety. In some embodiments, the Fn3 domain is a $^{10}$Fn3 domain. In some embodiments, the PK moiety increases the serum half-life of the polypeptide by more than 5, 10, 20, 30, 40, 50, 60, 70, 80, 90, 100, 120, 150, 200, 400, 600, 800, 1000% or more relative to the Fn3 domain alone.

In some embodiments, the PK moiety is a polymeric sugar. In some embodiments, the PK moiety is a polyethylene glycol moiety. In some embodiments the PK moiety is a serum albumin binding protein. In some embodiments the PK moiety is human serum albumin. In some embodiments the PK moiety is a serum immunoglobulin binding protein. In some embodiments, the PK moiety is transferrin. In some embodiments the PK moiety is another Adnectin specific for a serum protein.

Biophysical and Biochemical Characterization

The application provides Adnectin comprising a Fn3 domain that binds to the p19 subunit of IL-23. As shown in Table 1 and Example 4, polypeptide binding to a target molecule may be assessed in terms of equilibrium constants (e.g., dissociation, $K_D$) and in terms of kinetic constants (e.g., on-rate constant, $K_{on}$ and off-rate constant, $k_{off}$). An Adnectin will generally bind to a target molecule with a $K_D$ of less than 500 nM, 100 nM, 10 nM, 1 nM, 500 pM, 200 pM, 100 pM, although higher $K_D$ values may be tolerated where the $K_{off}$ is sufficiently low or the $K_{on}$, is sufficiently high.

The BC, DE and FG loop sequences of the family of anti-IL-23 Adnectin of the invention are presented in Table 1 below, as well as the corresponding full length SEQ ID NO.

TABLE 1

Anti-IL-23 Adnectin Family

| Clone ID | BC Loop | DE Loop | FG loop | On-rate (ka, $M^{-1}s^{-1}$) | Off-rate ($k_d, s^{-1}$) | Affinity ($K_D$, M) | Kit 225 pSTAT3 IC50 (nM) | SEQ ID NO |
|---|---|---|---|---|---|---|---|---|
| 1434A08 | GHYPMHV | HRTH | YYNEADYSQI | n.d. | n.d. | n.d. | 4.9 | 60 |
| 1437G04 | GHYPLHV | YYHY | YYNEADYSQI | 1.34E+05 | 4.46E-04 | 3.3E-09 | 3.3 | 61 |
| 1437A09 | GHYPMHV | SKQH | YYNEADYSQI | 8.06E+04 | 4.60E-04 | 5.7E-09 | 20.2 | 62 |
| 1438E05 | GHYPMHV | SNVH | YYNEADYSQI | n.d. | n.d. | n.d. | 39.6 | 63 |
| 1438D01 | GHYPMHV | NRAH | YYNEADYSQI | n.d. | n.d. | n.d. | 11.4 | 64 |
| 1438B02 | GHYPMHV | RKTY | YYNEADYSQI | n.d. | n.d. | n.d. | 8.6 | 65 |
| 1438A09 | GHYPMHV | RSRY | YYNEADYSQI | n.d. | n.d. | n.d. | 10.8 | 66 |
| 1486G03 | GHYPMHV | SRYY | YYNEADYSQI | 8.62E+04 | 4.25E-04 | 4.9E-09 | 3 | 67 |
| 1486C04 | GHYPMHV | PHRY | YYNEADYSQI | 1.12E+05 | 3.79E-04 | 3.4E-09 | 31.9 | 68 |
| 1486D04 | GHYPLHI | RSTH | YYNEADYSQI | 1.51E+05 | 3.52E-04 | 2.3E-09 | 2 | 69 |
| 1486B05 | GHYPMHV | SRIY | YYNEADYSQI | 1.34E+05 | 3.81E-04 | 2.8E-09 | 4 | 70 |
| 1486D05 | GHYPLHV | HQRY | YYNEADYSQI | 1.20E+05 | 3.44E-04 | 2.9E-09 | 4 | 71 |
| 1487C03 | GHYPLHI | KQVY | YYNEADYSQI | 1.61E+05 | 3.82E-04 | 2.4E-09 | 3.7 | 72 |
| 1487G03 | GHYPLHV | AHRY | YYNEADYSQI | 1.03E+05 | 3.16E-04 | 3.1E-09 | 3 | 73 |
| 1487D09 | GHYPMHI | RSRH | YYNEADYSQI | 1.50E+05 | 2.50E-04 | 1.7E-09 | 2 | 74 |
| 1487H04 | GHYPMHV | ARQY | YYQEYEYRYI | 5.96E+04 | too slow to measure | <nM | 2 | 75 |
| 1490E02 | GHYPMHV | RTQY | YYNEADYSQI | 9.73E+04 | 4.65E-04 | 4.8E-09 | n.d. | 76 |
| 1490G02 | GHYPMHV | PRYH | YYMEEKYAVI | 1.97E+05 | 3.32E-04 | 1.7E-09 | 0.4 | 77 |
| 1490H05 | GHYPLHV | MRQH | YYAQENYKEI | 1.56E+05 | 3.22E-04 | 2.1E-09 | 0.4 | 78 |
| 1490B03 | GHYPLHV | SRKY | YYKEANYREI | 1.53E+05 | too slow to measure | <nM | 0.3 | 79 |
| 1490H06 | GHYPLHI | RQKY | YYNEADYSQI | 9.35E+04 | too slow to measure | <nM | 2.3 | 80 |
| 1490A07 | GHYPLHI | HAKY | YYAQENYKEI | 1.63E+05 | too slow to measure | <nM | 0.6 | 81 |
| 1490C07 | GHYPLHV | SNRY | YYNEADYSQI | 9.56E+04 | 4.26E-04 | 4.5E-09 | 5.6 | 82 |
| 1490H08 | GHYPLHI | NTSH | YYNEADYSQI | 1.67E+05 | 5.87E-04 | 3.5E-09 |  | 83 |
| 1491A05 | GHYPLHV | SQVY | YYAQENYKEI | 1.98E+05 | 4.08E-04 | 2.1E-09 | 0.3 | 84 |
| 1571H03 | GHYPLHV | NRVY | YYAQEEYHII | 1.18E+05 | 3.95E-04 | 3.4E-09 | 0.4 | 85 |
| 1571G04 | GHYPLHV | PRSH | YYAQENYKEI | 1.70E+05 | 3.61E-04 | 2.1E-09 | 0.1 | 86 |
| 1571G06 | GHYPLHL | RTKY | YYKEADYSQI | 1.31E+05 | 2.38E-04 | 1.8133E-09 | 0.3 | 87 |
| 1571F10 | GHYPLHI | SRYH | YYEQVEYREI | 2.68E+05 | too slow to measure | <nM | 0.1 | 88 |

TABLE 1-continued

Anti-IL-23 Adnectin Family

| Clone ID | BC Loop | DE Loop | FG loop | On-rate (ka, $M^{-1}s^{-1}$) | Off-rate ($k_d, s^{-1}$) | Affinity ($K_D$, M) | Kit 225 pSTAT3 IC50 (nM) | SEQ ID NO |
|---|---|---|---|---|---|---|---|---|
| 1572D04 | GHYPMHV | PRRY | YYEQPIYATI | 1.03E+05 | 2.94E-04 | 2.9E-09 | 4 | 89 |
| 1572F05 | GHYPLHI | RQKY | YYNEADYSQI | 1.32E+05 | 2.85E-04 | 2.2E-09 | 3 | 90 |
| 1572G06 | GHYPLHV | RYKY | YYAQENYKEI | 1.05E+05 | too slow to measure | <nM | 0.05 | 91 |
| 1572B10 | GHYPMHV | VPRH | YYNEADYSQI | 6.53E+04 | too slow to measure | <nM | 0.8 | 92 |
| 1572C09 | GHYPMHI | TPKH | YYNEADYSQI | 6.07E+04 | too slow to measure | <nM | 0.5 | 93 |
| 1572H05 | GHYPLHI | RSKY | YYEQVEYREI | 3.75E+05 | 2.30E-04 | 6.1E-10 | 0.01 | 94 |
| 1572H08 | GHYPLHV | SRKY | YYNEADYSQI | 5.73E+04 | too slow to measure | <nM | 2.8 | 95 |
| 1550A07 | GHYPMHV | VPRY | YYAQENYKEI | 1.17E+05 | 1.33E-04 | 1.1E-09 | 1.0 | 96 |
| 1550C05 | GHYPMHV | PRRY | YYNEADYSQI | 6.59E+04 | 1.35E-04 | 2.1E-09 | 16.8 | 97 |
| 1550E03 | GHYPLHI | RMRH | YYSEELYKYI | 9.95E+04 | 1.86E-04 | 1.9E-09 | 5.3 | 98 |
| 1550E06 | GHYPMHV | PPRH | YYAQENYKEI | 5.54E+04 | 1.16E-04 | 2.1E-09 | 0.4 | 99 |
| 1550H05 | GHYPLHV | RQIY | YYNEADYSQI | 6.52E+04 | 2.12E-04 | 3.3E-09 | 1.5 | 100 |

*Method for affinity determinations: The anti-His antibody, mAb050 (RnD Systems, MN) was diluted to 20 ug/mL in acetate 5.0 and immobilized to ~9000 RU on flow cells 1 and 2 of a CM5 chip surface (GE Healthcare, Piscataway, NJ) according to the manufacturer's instructions. All surface plasmon experiments were conducted in HBS-EP (10 mM Hepes 150 mM NaCl 3 mM EDTA 0.05% Surfactant P20) at 25° C. IL-23 was injected over anti-His mAb captured Adnectins for 2 minutes followed by a 10 minute dissociation phase. Evaluation of the binding specificity was completed using Biacore T100 evaluation software. Additional detailed methods are described in Example 4.

Additional anti-IL-23 Adnectin characterization is described in Table 2.

TABLE 2

Anti-IL-23 Adnectin IC50/EC50

| clone ID | BC | DE | FG | PBMNC pSTAT3 IC50 (nM) | IL-17 EC50 (nM) | IL-22 EC50 (nM) |
|---|---|---|---|---|---|---|
| 1571G04 | GHYPLHV | PRSH | YYAQENYKEI | 0.23 ± .05 | 1.4 ± 0.3 | 1.3 ± 0.7 |
| 1490B03 | GHYPLHV | SRKY | YYKEANYREI | .09 ± .01 | 1.4 ± 0.1 | 1.7 ± 0.8 |
| 1572G06 | GHYPLHV | RYKY | YYAQENYKEI | .21 ± .03 | 1.6 ± 0.3 | 1.9 ± 0.3 |
| 1550E06 | GHYPMHV | PPRH | YYAQENYKEI | 1.15 ± .5 | 1.5 ± 0.6 | 2.1 ± 0.8 |
| 1571H03 | GHYPLHV | NRVY | YYAQEEYHII | n.d. | 2.9 ± 0.8 | 2.3 ± 0.4 |
| 1490H05 | GHYPLHV | MRQH | YYAQENYKEI | n.d. | 1.8 ± 2.1 | 2.9 ± 1.0 |
| 1571G06 | GHYPLHL | RTKY | YYKEADYSQI | 0.93 ± .5 | 3.5 ± 1.4 | 5.1 ± 4.3 |
| 1572C09 | GHYPMHI | TPKH | YYNEADYSQI | n.d. | 7.9 ± 6.1 | 5.3 ± 4.5 |

(n.d. not determined)
(Detailed methods described in Example 4).

Nucleic Acid-Protein Fusion Technology

In one aspect, the application provides Adnectin comprising fibronectin type III domains that bind p19 subunit of IL-23. One way to rapidly make and test Fn3 domains with specific binding properties is the nucleic acid-protein fusion tagging technology, termed PROfusion, which exploits nucleic acid-protein fusions (RNA- and DNA-protein fusions) to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558, 6,261,804, 6,214,553, 6,281,344, 6,207,446, 6,518,018, 6,818,418; and Roberts et al., *Proc. Natl., Acad. Sci.*, 94:12297-12302 (1997), herein incorporated by reference.

Vectors and Polynucleotides Embodiments

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*, 100(2):438-442 (Jan. 21, 2003); Sinclair et al., *Protein Expr. Purif.*, 26(I):96-105 (October 2002); Connell, N. D., *Curr. Opin. Biotechnol.*, 12(5):446-449 (October 2001); Makrides et al., *Microbiol. Rev.*, 60(3):512-538 (September 1996); and Sharp et al., *Yeast*, 7(7):657-678 (October 1991).

General techniques for nucleic acid manipulation are described for example in Sambrook et al., *Molecular Cloning: A Laboratory Manual*, 2nd Edition, Vols. 1-3, Cold Spring Harbor Laboratory Press, publ. (1989), or Ausubel, F. et al., *Current Protocols in Molecular Biology*, Green Publishing and Wiley-Interscience, New York, publ. (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene, to facilitate recognition of transformants, are additionally incorporated.

The proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell.

For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders.

For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein of the invention, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein of the invention. Promoter sequences are also known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tall to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding proteins of the invention by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature,* 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein of the invention. One useful transcription termination component is the bovine growth hormone polyadenylation region. See WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual,* Elsevier, New York, publ. (1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* genus, such as *S. cerevisiae,* may also be used for production of polypeptides. Various mammalian or insect cell culture systems can also be employed to express recombinant proteins. Baculovirus systems for production of heterologous proteins in insect cells are reviewed by Luckow et al. (*Bio/Technology,* 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* the preferred method for expression. The protein is then purified from culture media or cell extracts.

Protein Production

Host cells are transformed with the herein-described expression or cloning vectors for protein production and cultured in conventional nutrient media modified as appropriate for inducing promoters, selecting transformants, or amplifying the genes encoding the desired sequences. In the examples shown here, the host cells used for high-throughput protein production (HTPP) and mid-scale production was the BL21 DE3 plysS-bacterial strain. The host cells used to produce the proteins of this invention may be cultured in a variety of media, such as those described in Ham et al., *Meth. Enzymol.,* 58:44 (1979), Barites et al., *Anal. Biochem.,* 102:255 (1980), U.S. Pat. Nos. 4,767,704, 4,657,866, 4,927,762, 4,560,655, 5,122,469, 6,048,728, 5,672,502, or U.S. Pat. No. RE30,985. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Proteins of the invention can also be produced by chemical synthesis (e.g., by the methods described in *Solid Phase Peptide Synthesis,* 2nd Edition, The Pierce Chemical Co., Rockford, Ill., publ. (1984). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, or preferably at least 95% pure, and most preferably at least 98% pure. Regardless of the exact numerical value of the purity, the polypeptide is sufficiently pure for use as a pharmaceutical product.

A platform manufacturing process was used to prepare anti-IL-23 Adnectin. Example 1 describes an example of the manufacturing process. The Adnectin is produced in *Escherichia coli* (*E. coli*). *E. coli* MG1655 cells were transformed with expression vector (pBMS2008/ATI001044) which produces the protein in an insoluble form as inclusion bodies. The recombinant strain is grown in stirred tank fermentors. At the end of fermentation the inclusion bodies are collected, solubilized, and refolded in preparation for purification. The purified Adnectin is conjugated to a 40 kDa branched methoxyPEG using a maleimide linker. The conjugated material is subsequently repurified to remove free PEG, free Adnectin and product related impurities. Quality control testing is performed on the bulk drug substance.

Therapeutic In Vivo Uses

In one aspect, the application provides anti-IL-23 Adnectin useful in the treatment of autoimmune diseases such as lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g., insulin dependent diabetes mellitis, type I diabetes mellitis), Goodpasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjögren's syndrome, rheumatic diseases (e.g., rheumatoid arthritis), polymyositis, scleroderma, and mixed connective tissue disease.

The application also provides methods for administering anti-IL-23 Adnectins to a subject. In some embodiments, the subject is a human. In some embodiments, the anti-IL-23 Adnectins are pharmaceutically acceptable to a mammal, in particular a human. A "pharmaceutically acceptable" polypeptide refers to a polypeptide that is administered to an animal without significant adverse medical consequences, such as essentially endotoxin free or having very low endotoxin levels.

Formulation and Administration

The application further provides pharmaceutically acceptable compositions comprising the anti-IL-23 Adnectin described herein, wherein the composition is essentially endotoxin free. Therapeutic formulations comprising anti-IL-23 Adnectin are prepared for storage by mixing the described Adnectin having the desired degree of purity with optional physiologically acceptable carriers, excipients or stabilizers (Osol, A., ed., *Remington's Pharmaceutical Sciences,* 16th Edition (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethoninm chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, PLURONIC® or polyethylene glycol (PEG).

The formulations herein may also contain more than one active compound as necessary for the particular indication being treated, preferably those with complementary activities that do not adversely affect each other. Such molecules are suitably present in combination in amounts that are effective for the purpose intended.

The formulations to be used for in vivo administration must be sterile. This is readily accomplished by filtration through sterile filtration membranes.

The skilled artisan will understand that the dosage of each therapeutic agent will be dependent on the identity of the agent.

For therapeutic applications, the anti-IL-23 Adnectin is administered to a subject, in a pharmaceutically acceptable dosage form. It can be administered intravenously as a bolus or by continuous infusion over a period of time, or by subcutaneous routes. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, (2) 0.9% saline (0.9% w/v NaCl), and (3) 5% (w/v) dextrose.

The method of the present invention can be practiced in vitro, in vivo, or ex vivo.

Administration of anti-IL-23 Adnectin, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being administered.

When present in an aqueous dosage form, rather than being lyophilized, the protein typically will be formulated at a concentration of about 0.1 mg/ml to 100 mg/ml, although wide variation outside of these ranges is permitted. For the treatment of disease, the appropriate dosage of anti-IL-23 Adnectin will depend on the type of disease to be treated, the severity and course of the disease, whether the Adnectin is administered for preventive or therapeutic purposes, the course of previous therapy, the patient's clinical history and response to the Adnectin, and the discretion of the attending physician. The protein is suitably administered to the patient at one time or over a series of treatments.

Fusions of Serum Albumin Binding Adnectin (SABA)

In certain aspects, the application provides fusion proteins comprising anti-IL23-Adnectin fused to a $^{10}$Fn3 domains that binds to human serum albumin (a Serum Albumin Binding Adnectin ($^{10}$Fn3 domain) or SABA). Such fusion proteins have extended serum half lives in the presence of albumin relative to anti-IL23-Adnectin alone.

In certain aspects, the application provides fusion proteins comprising $^{10}$Fn3 domains that bind specifically to serum albumin, e.g., human serum albumin (HSA) to prolong the $t_{1/2}$ of the fusion protein.

In certain embodiments, the serum half-life of the anti-IL23-Adnectin fused to the SABA is increased relative to the serum half-life of the anti-IL23-Adnectin when not conjugated to the SABA. In certain embodiments, the serum half-life of the SABA fusion is at least 20, 40, 60, 80, 100, 120, 150, 180, 200, 400, 600, 800, 1000, 1200, 1500, 1800, 1900, 2000, 2500, or 3000% longer relative to the serum half-life of the anti-IL23-Adnectin when not fused to the SABA. In other embodiments, the serum half-life of the SABA fusion is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the anti-IL23-Adnectin when not fused to the SABA. In some embodiments, the serum half-life of the SABA fusion is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

Accordingly, the SABA fusion molecules described herein are useful for increasing the half-life of anti-IL23-Adnectin by creating a fusion between anti-IL23-Adnectin and the SABA. Such fusion molecules may be used to treat conditions which respond to the biological activity of IL23. The present invention contemplates the use of the SABA fusion molecules in diseases caused by the disregulation of IL-23.

The fusion may be formed by attaching anti-IL23-Adnectin to either end of the SABA molecule, i.e., SABA-anti-IL23-Adnectin or anti-IL23-Adnectin-SABA arrangements.

In one aspect, the disclosure provides fusion proteins comprising anti-IL23-Adnectin comprising a serum albumin binding $^{10}$Fn3 domain. In exemplary embodiments, the serum albumin binding $^{10}$Fn3 proteins described herein bind to HSA with a $K_D$ of less than 3 uM, 2.5 uM, 2 uM, 1.5 uM, 1 uM, 500 nM, 100 nM, 50 nM, 10 nM, 1 nM, 500 pM, 200 pM, 100 pM, 50 pM or 10 pM. In certain embodiments, the serum albumin binding $^{10}$Fn3 proteins described herein bind to HSA with a $K_D$ of less than 3 uM, 2.5 uM, 2 uM, 1.5 uM, 1 uM, 500 nM, 100 nM, 50 nM, 10 nM, 1 nM, 500 pM, 200 pM, 100 pM, 50 pM or 10 pM at a pH range of 5.5 to 7.4 at 25° C. or 37° C. In some embodiments, the serum albumin binding $^{10}$Fn3 proteins described herein bind more tightly to HSA at a pH less than 7.4 as compared to the binding affinity for HSA at a pH of 7.4 or greater.

In certain embodiments, the fusion proteins comprising HSA binding $^{10}$Fn3 domains described herein may also bind serum albumin from one or more of monkey, rat, or mouse. In certain embodiments, the serum albumin binding $^{10}$Fn3 proteins described herein bind to rhesus serum albumin (RhSA) or cynomolgus monkey serum albumin (CySA) with a $K_D$ of less than 3 uM, 2.5 uM, 2 uM, 1.5 uM, 1 uM, 500 nM, 100 nM, 50 nM, 10 nM, 1 nM, 500 pM or 100 pM.

In certain embodiments, the fusion proteins comprising serum albumin binding $^{10}$Fn3 domains described herein bind to domain I and/or domain II of HSA. In one embodiment, the fusion proteins comprising serum albumin binding $^{10}$Fn3 domains described herein do not bind to domain III of HSA.

In certain embodiments, the serum albumin binding $^{10}$Fn3 (SABA) portion of the fusion proteins comprises a sequence having at least 40%, 50%, 60%, 70%, 75%, 80% or 85% identity to the wild-type $^{10}$Fn3 domain (SEQ ID NO: 1). In one embodiment, at least one of the BC, DE, or FG loops is modified relative to the wild-type $^{10}$Fn3 domain. In another embodiment, at least two of the BC, DE, or FG loops are modified relative to the wild-type $^{10}$Fn3 domain. In another embodiment, all three of the BC, DE, and FG loops are modified relative to the wild-type $^{10}$Fn3 domain. In other embodiments, a SABA comprises a sequence having at least 40%, 50%, 60%, 70%, 75%, 80%, 85%, 90%, or 95% identity to any one of the 26 core SABA sequences shown in Table 3 (i.e., SEQ ID NO: 103, 107, 111, 115, 119, and 123-143) or any one of the extended SABA sequences shown in Table 3 (i.e., SEQ ID NO: 188-215, minus the 6×HIS tag).

In certain embodiments, the core amino acid residues are fixed and any substitutions, conservative substitutions, deletions or additions occur at residues other than the core amino acid residues. In exemplary embodiments, the BC, DE, and FG loops are replaced with polypeptides comprising the BC, DE and FG loop sequences from any of the HSA binders shown in Table 3 below (i.e., SEQ ID NOs: 103, 107, 111, 115, 119, and 123-143 in Table 3).

In certain embodiments, a SABA (e.g., a SABA core sequence or a sequence based thereon as described above) may be modified to comprise an N-terminal extension sequence and/or a C-terminal extension sequence. Exemplary extension sequences are shown in Table 3. For example, SEQ ID NO: 188 designated as SABA1.1 comprises the core SABA 1 sequence (SEQ ID NO: 103) with an N-terminal sequence MGVSDVPRDLE (SEQ ID NO: 144, designated as AdNT1), and a C-terminal sequence EIDKPSQ (SEQ ID NO: 153). SABA1.1 further comprises a His6 tag at the C-terminus, however, it should be understood that the His6 tag is completely optional and may be placed anywhere within the N- or C-terminal extension sequences. Further, any of the exemplary N- or C-terminal extension sequences provided in Table 3 (SEQ ID NO: 144-163), and any variants thereof, can be used to modify any given SABA core sequence provided in Table 3.

In other embodiments, the tail sequences may be combined with other known linker sequences (e.g., SEQ ID NO: 164-187 in Table 3) as necessary when designing a SABA fusion molecule.

Conjugation Linkers

SABA fusions may be covalently or non-covalently linked. In some embodiments, a serum albumin binding $^{10}$Fn3 may be directly or indirectly linked to a anti-IL23-Adnectin via a polypeptide linker. Suitable linkers for joining Fn3 are those which allow the separate domains to fold independently of each other forming a three dimensional structure that permits high affinity binding to a target molecule.

The disclosure provides a number of suitable linkers that meet these requirements, including glycine-serine based linkers, glycine-proline based linkers, as well as the linker having the amino acid sequence PSTSTST (SEQ ID NO: 184). The Examples described herein demonstrate that Fn3 domains joined via polypeptide linkers retain their target binding function. In some embodiments, the linker is a glycine-serine based linker. These linkers comprise glycine and serine residues and may be between 8 and 50, 10 and 30, and 10 and 20 amino acids in length. Examples include linkers having an amino acid sequence $(GS)_7$ (SEQ ID NO: 171), $G(GS)_6$ (SEQ ID NO: 166), and $G(GS)_7G$ (SEQ ID NO: 168). Other linkers contain glutamic acid, and include, for example, $(GSE)_5$ (SEQ ID NO: 173) and GGSE GGSE (SEQ ID NO: 177). Other exemplary glycine-serine linkers include $(GS)_4$ (SEQ ID NO: 170), $(GGGGS)_7$ (SEQ ID NO: 179), $(GGGGS)_5$ (SEQ ID NO: 180), and $(GGGGS)_3G$ (SEQ ID NO: 181). In some embodiments, the linker is a glycine-proline based linker. These linkers comprise glycine and proline residues and may be between 3 and 30, 10 and 30, and 3 and 20 amino acids in length. Examples include linkers having an amino acid sequence $(GP)_3G$ (SEQ ID NO: 182) and $(GP)_5G$ (SEQ ID NO: 183). In other embodiments, the linker may be a proline-alanine based linker having between 3 and 30, 10 and 30, and 3 and 20 amino acids in length. Examples of proline alanine based linkers include, for example, $(PA)_3$ (SEQ ID NO: 185), $(PA)_6$ (SEQ ID NO: 186) and $(PA)_9$ (SEQ ID NO: 187). It is contemplated, that the optimal linker length and amino acid composition may be determined by routine experimentation by methods well known in the art.

In some embodiments, the fusions described herein are linked via a polypeptide linker having a protease site that is cleavable by a protease in the blood or target tissue. Such embodiments can be used to release a therapeutic protein for better delivery or therapeutic properties or more efficient production.

Additional linkers or spacers, may be introduced at the C-terminus of a Fn3 domain between the Fn3 domain and the polypeptide linker. Additional linkers or spacers may be introduced at the N-terminus of a Fn3 domain between the Fn3 domain and the polypeptide linker.

In some embodiments, a therapeutic moiety may be directly or indirectly linked to a SABA via a polymeric linker. Polymeric linkers can be used to optimally vary the distance between each component of the fusion to create a protein fusion with one or more of the following characteristics: 1) reduced or increased steric hindrance of binding of one or more protein domains when binding to a protein of interest, 2) increased protein stability or solubility, 3) decreased protein aggregation, and 4) increased overall avidity or affinity of the protein.

In some embodiments, a therapeutic moiety is linked to a SABA via a biocompatible polymer such as a polymeric sugar. The polymeric sugar can include an enzymatic cleavage site that is cleavable by an enzyme in the blood or target tissue. Such embodiments can be used to release a therapeutic proteins for better delivery or therapeutic properties or more efficient production.

Summary of Serum Albumin-Binding Adnectins (SABA) Sequences

Many of the SABA sequences referenced in this application are summarized in Table 3 below. Unless otherwise specified, all N-terminal extensions are indicated with a single underline, all C-terminal tails/extensions are indicated with a double underline, and linker sequences are boxed. Loop regions BC, DE and FG are shaded for each core SABA sequence.

TABLE 3

Summary of SABA Exemplary Sequences

| SEQ ID NO: | Sequence Name | Description | Sequence |
|---|---|---|---|
| 103 | SABA1 | Core 1 Adnectin | EVVAATPTSLLISWHSYYEQNSYYRITYGE TGGNSPVQEFTVPYSQTTATISGLKPGVDY TITVYAVYGSKYYYPISINYRT |
| 104 | SABA1BC | Core 1 BC Loop | HSYYEQNS |
| 105 | SABA1DE | Core 1 DE Loop | YSQT |
| 106 | SABA1FG | Core 1 FG Loop | YGSKYYY |
| 107 | SABA2 | Core 2 Adnectin | EVVAATPTSLLISWPKYDKTGHYYRITYGE TGGNSPVQEFTVPTRQTTATISGLKPGVDY TITVYAVSKDDYYPHEHRPISINYRT |
| 108 | SABA2BC | Core 2 BC Loop | PKYDKTGH |
| 109 | SABA2DE | Core 2 DE Loop | TRQT |
| 110 | SABA2FG | Core 2 FG Loop | SKDDYYPHEHR |
| 111 | SABA3 | Core 3 Adnectin | EVVAATPTSLLISWSNDGPGLSYYRITYGE TGGNSPVQEFTVPSSQTTATISGLKPGVDY TITVYAVSYYTKKAYSAGPISINYRT |
| 112 | SABA3BC | Core 3 BC Loop | SNDGPGLS |
| 113 | SABA3DE | Core 3 DE Loop | SSQT |
| 114 | SABA3FG | Core 3 FG Loop | SYYTKKAYSAG |
| 115 | SABA4 | Core 4 Adnectin; contains a scaffold mutation; scaffold-perfect version is SABA5 | EMVAATPTSLLISWEDDSYYSRYYRITYGE TGGNSPVQEFTVPSDLYTATISGLKPGVDY TITVYAVYDVTDLIMHEPISINYRT |
| 116 | SABA4BC | Core 4 BC Loop | EDDSYYSR |
| 117 | SABA4DE | Core 4 DE Loop | SDLY |
| 118 | SABA4FG | Core 4 FG Loop | YDVTDLIMHE |
| 119 | SABA5 | Core 5 Adnectin; see description for SAVA4 | EVVAATPTSLLISWEDDSYYSRYYRITYGE TGGNSPVQEFTVPSDLYTATISGLKPGVDY TITVYAVYDVTDLIMHEPISINYRT |
| 120 | SABA5BC | Core 5 BC Loop | EDDSYYSR |
| 121 | SABA5DE | Core 5 DE Loop | SDLY |
| 122 | SABA5FG | Core 5 FG Loop | YDVTDLIMHE |
| 123 | SABA6 | Core 6 Adnectin | EVVAATPTSLLISWYMDEYDVRYYRITYGE TGGNSPVQEFTVPNYYNTATISGLKPGVDY TITVYAVTRIKANNYMYGPISINYRT |
| 124 | SABA7 | Core 7 Adnectin | EVVAATPTSLLISWNHLEHVARYYRITYGE TGGNSPVQEFTVPEYPTTATISGLKPGVDY TITVYAVTITMLKYPTQSPISINYRT |
| 125 | SABA8 | Core 8 Adnectin | EVVAATPTSLLISWGHYRRSGHYYRITYGE TGGNSPVQEFTVPDPSSYTATISGLKPGVDY TITVYAVSKDDYYPHEHRPISINYRT |
| 126 | SABA9 | Core 9 Adnectin | EVVAATPTSLLISWDASHYERRYYRITYGE TGGNSPVQEFTVPRYHHTATISGLKPGVDY TITVYAVTQAQEHYQPPPISINYRT |
| 127 | SABA10 | Core 10 Adnectin | EVVAATPTSLLISWNSYYHSADYYRITYGE TGGNSPVQEFTVPYPPTTATISGLKPGVDY TITVYAVYSAKSYYPPISINYRT |
| 128 | SABA11 | Core 11 Adnectin | EVVAATPTSLLISWSKYSKHGHYYRITYGE TGGNSPVQEFTVPSGNATATISGLKPGVDY TITVYAVEDTNDYPHTHRPISINYRT |
| 129 | SABA12 | Core 12 Adnectin | EVVAATPTSLLISWHGEPDQTRYYRITYGE TGGNSPVQEFTVPPYRRTATISGLKPGVDY TITVYAVTSGYTGHYQPISINYRT |
| 130 | SABA13 | Core 13 Adnectin | EVVAATPTSLLISWSKYSKHGHYYRITYGE TGGNSPVQEFTVPDPSSYTATISGLKPGVDY TITVYAVSKDDYYPHEHRPISINYRT |
| 131 | SABA14 | Core 14 Adnectin | EVVAATPTSLLISWYEPYTPIHYYRITYGE TGGNSPVQEFTVPGYYGTATISGLKPGVDY TITVYAVYGYYQYTPISINYRT |
| 132 | SABA15 | Core 15 Adnectin | EVVAATPTSLLISWSKYSKHGHYYRITYGE TGGNSPVQEFTVPSGNATATISGLKPGVDY TITVYAVSDDNKYYHQHRPISINYRT |
| 133 | SABA16 | Core 16 Adnectin | EVVAATPTSLLISWGHYRRSGHYYRITYGE TGGNSPVQEFTVPDPSSYTATISGLKPGVDY TITVYAVSKDDYYPHEHRPISINYRT |
| 134 | SABA17 | Core 17 Adnectin | EVVAATPTSLLISWSKYSKHGHYYRITYGE TGGNSPVQEFTVPSGNATATISGLKPGVDY TITVYAVEDTNDYPHTHRPISINYRT |
| 135 | SABA18 | Core 18 Adnectin | EVVAATPTSLLISWYEPGASVYYYRITYGE TGGNSPVQEFTVPSYYHTATISGLKPGVDY TITVYAVYGYYEYEPISINYRT |

TABLE 3-continued

Summary of SABA Exemplary Sequences

| SEQ ID NO: | Sequence Name | Description | Sequence |
|---|---|---|---|
| 136 | SABA19 | Core 19 Adnectin | EVVAATPTSLLISWQSYYAHSDYYRITYGETGGNSPVQEFTVPYPPQTATISGLKPGVDYTITVYAVYAGSSYYPISINYRT |
| 137 | SABA20 | Core 20 Adnectin | EVVAATPTSLLISWGHYRRSGHYYRITYGETGGNSPVQEFTVPDPSSYTATISGLKPGVDYTITVYAVSKDDYYPHEHRPISINYRT |
| 138 | SABA21 | Core 21 Adnectin | EVVAATPTSLLISWPEPGTPVYYRITYGETGGNSPVQEFTVPAYYGTATISGLKPGVDYTITVYAVYGYYDYSPISINYRT |
| 139 | SABA22 | Core 22 Adnectin | EVVAATPTSLLISWYRYEKTQHYYRITYGETGGNSPVQEFTVPPESGTATISGLKPGVDYTITVYAVYAGYEYPHTHRPISINYRT |
| 140 | SABA23 | Core 23 Adnectin | EVVAATPTSLLISWVKSEEYYRYYRITYGETGGNSPVQEFTVPYYVHTATISGLKPGVDYTITVYAVTEYYYAGAVVSVPISINYRT |
| 141 | SABA24 | Core 24 Adnectin | EVVAATPTSLLISWYDPYTYGSYYRITYGETGGNSPVQEFTVPGPYTTTATISGLKPGVDYTITVYAVSYYYSTQPISINYRT |
| 142 | SABA25 | Core 25 Adnectin | EVVAATPTSLLISWSNDGPGLSYYRITYGETGGNSPVQEFTVPSSQTTATISGLKPGVDYTITVYAVSYYTKKAYSAGPISINYRT |
| 143 | SABA26 | Core 26 Adnectin | EVVAATPTSLLISWPDPYYKPDYYRITYGETGGNSPVQEFTVPRDYTTATISGLKPGVDYTITVYAVYSYYGYYPISINYRT |
| | Exemplary Adnectin N-Terminal Extension Sequences | | |
| 144 | AdNT1 | Exemplary leader | MGVSDVPRDL |
| 145 | AdNT2 | Exemplary leader | GVSDVPRDL |
| 146 | AdNT3 | Exemplary leader | VSDVPRDL |
| 147 | AdNT4 | Exemplary leader | SDVPRDL |
| 148 | AdNT5 | Exemplary leader | DVPRDL |
| 149 | AdNT6 | Exemplary leader | VPRDL |
| 150 | AdNT7 | Exemplary leader | PRDL |
| 151 | AdNT8 | Exemplary leader | RDL |
| 152 | AdNT9 | Exemplary leader | DL |
| | Exemplary Adnectin C-Terminal Extension Sequences | | |
| 153 | AdCT1 | Exemplary tail | EIDKPSQ |
| 154 | AdCT2 | Exemplary tail | EIDKPS |
| 155 | AdCT3 | Exemplary tail | EIDKPC |
| 156 | AdCT4 | Exemplary tail | EIDKP |
| 157 | AdCT5 | Exemplary tail | EIDK |
| 158 | AdCT6 | Exemplary tail | EI |
| 159 | AdCT7 | Exemplary tail | EIEKPSQ |
| 160 | AdCT8 | Exemplary tail | EIDKPSQLE |
| 161 | AdCT9 | Exemplary tail | EIEDEDEDED |
| 162 | AdCT10 | Exemplary tail | EIEKPSQEDEDEDEDED |
| 163 | AdCT11 | Exemplary tail | EGSGS |
| 164 | L1 | G(GS)$_2$ | GGSGS |
| 165 | L2 | G(GS)$_4$ | GGSGSGSGS |
| 166 | L3 | G(GS)$_6$ | GGSGSGSGSGSGS |
| 167 | L4 | G(GS)$_7$ | GGSGSGSGSGSGSGS |
| 168 | L5 | G(GS)$_7$G | GGSGSGSGSGSGSGSG |
| 169 | L6 | GSGS | GSGS |
| 170 | L7 | (GS)$_4$ | GSGSGSGS |
| 171 | L7 | (GS)$_7$ | GSGSGSGSGSGSGS |
| 172 | L9 | GS(A)9GS | GSAAAAAAAAAGS |
| 173 | L10 | (GSE)$_5$ | GSEGSEGSEGSEGSE |
| 174 | L11 | (PAS)$_5$ | PASPASPASPASPAS |
| 175 | L12 | (GSP)$_5$ | GSPGSPGSPGSPGSP |
| 176 | L13 | GS(TVAAPS)$_2$ | GSTVAAPSTVAAPS |
| 177 | L14 | (GGSE)$_2$ | GGSEGGSE |
| 178 | L15 | (ST)$_3$G | STSTSTG |
| 179 | L16 | (GGGGS)$_7$ | GGGGSGGGGSGGGGSGGGGSGGGGSGGGGSGGGGS |
| 180 | L17 | (GGGGS)$_5$ | GGGGSGGGGSGGGGSGGGGSGGGGS |
| 181 | L18 | (GGGGS)$_3$G | GGGGSGGGGSGGGGSG |
| 182 | L19 | (GP)$_3$G | GPGPGPG |
| 183 | L20 | (GP)$_5$G | GPGPGPGPGPG |
| 184 | L21 | P(ST)$_3$ | PSTSTST |
| 185 | L22 | (PA)$_3$ | PAPAPA |
| 186 | L23 | (PA)$_6$ | PAPAPAPAPAPA |
| 187 | L24 | (PA)$_9$ | PAPAPAPAPAPAPAPAPA |

TABLE 3-continued

Summary of SABA Exemplary Sequences

| SEQ ID NO: | Sequence Name | Description | Sequence |
|---|---|---|---|
| | | Exemplary Extensions to Adnectin Core Sequences | |
| 188 | SABA1.1 | Adnectin core 1 sequence having AdNT1 and AdCT1 terminal sequences with His6 tag | MGVSDVPRDLEVVAATPTSLLISWHSYYEQ NSYYRITYGETGGNSPVQEFTVPYSQTTAT ISGLKPGVDYTITVYAVYGSKYYYPISINY RTEIDKPSQHHHHHH |
| 189 | SABA1.2 | Adnectin core 1 sequence having AdNT1 and AdCT1 terminal sequences with | MGVSDVPRDLEVVAATPTSLLISWHSYYEQ NSYYRITYGETGGNSPVQEFTVPYSQTTAT ISGLKPGVDYTITVYAVYGSKYYYPISINY RTEIEDEDEDEDED |
| 190 | SABA1.3 | His6 tag Adnectin core 1 sequence having AdNT1 and AdCT1 terminal sequences with | MGVSDVPRDLEVVAATPTSLLISWHSYYEQ NSYYRITYGETGGNSPVQEFTVPYSQTTAT ISGLKPGVDYTITVYAVYGSKYYYPISINY RTEIEDEDEDEDEDHHHHHH |
| 191 | SABA2.1 | His6 tag Adnectin core 2 sequence having AdNT1 and AdCT1 terminal sequences with | MGVSDVPRDLEVVAATPTSLLISWPKYDKT GHYYRITYGETGGNSPVQEFTVPTRQTTAT ISGLKPGVDYTITVYAVSKDDYYPHEH RPISINYRTEIDKPSQHHHHHH |
| 192 | SABA3.1 | His6 tag Adnectin core 3 sequence having AdNT1 and AdCT1 terminal sequences with | MGVSDVPRDLEVVAATPTSLLISWSNDGPG LSYYRITYGETGGNSPVQEFTVPSSQTTAT ISGLKPGVDYTITVYAVSYYTKKAY SAGPISINYRTEIDKPSQHHHHHH |
| 193 | SABA4.1 | His6 tag Adnectin core 4 sequence having AdNT1 and AdCT1 terminal sequences with | MGVSDVPRDLEMVAATPTSLLISWEDDSYY SRYYRITYGETGGNSPVQEFTVPSDLYTAT ISGLKPGVDYTITVYAVTYDVTDLIM HEPISINYRTEIDKPSQHHHHHH |
| 194 | SABA5.1 | His6 tag Adnectin core 5 sequence having AdNT1 | MGVSDVPRDLEVVAATPTSLLISWEDDSYY SRYYRITYGETGGNSPVQEFTVPSDLYTAT ISGLKPGVDYTITVYAVTYDVTDLIM HEPISINYRTEIDKPSQHHHHHH |
| | | and AdCT1 terminal sequences with | |
| 195 | SABA6.1 | His6 tag Adnectin core 6 sequence having AdNT1 and AdCT1 terminal sequences with | MGVSDVPRDLEVVAATPTSLLISWYMDEYD VRYYRITYGETGGNSPVQEFTVPNYYNTAT ISGLKPGVDYTITVYAVTRIKANNY MYGPISINYRTEIDKPSQHHHHHH |
| 196 | SABA7.1 | His6 tag Adnectin core 7 sequence having AdNT1 and AdCT1 terminal sequences with | MGVSDVPRDLEVVAATPTSLLISWNHLEHV ARYYRITYGETGGNSPVQEFTVPEYPTTAT ISGLKPGVDYTITVYAVTITMLKYP TQSPISINYRTEIDKPSQHHHHHH |
| 197 | SABA8.1 | His6 tag Adnectin core 8 sequence having AdNT1 and AdCT1 terminal sequences with | MGVSDVPRDLEVVAATPTSLLISWGHYRRS GHYYRITYGETGGNSPVQEFTVPDSSYTAT ISGLKPGVDYTITVYAVSKDDYYPHEH RPISINYRTEIDKPSQHHHHHH |
| 198 | SABA9.1 | His6 tag Adnectin core 9 sequence having AdNT1 and AdCT1 terminal sequences with | MGVSDVPRDLEVVAATPTSLLISWDASHYE RRYYRITYGETGGNSPVQEFTVPRYHHTAT ISGLKPGVDYTITVYAVTQAQEHYQP PISINYRTEIDKPSQHHHHHH |
| 199 | SABA10.1 | His6 tag Adnectin core 10 sequence having AdNT1 and AdCT1 terminal sequences with | MGVSDVPRDLEVVAATPTSLLISWNSYYHS ADYYRITYGETGGNSPVQEFTVPYPPTTAT ISGLKPGVDYTITVYAVYSAKSYY PISINYRTEIDKPSQHHHHHH |
| 200 | SABA11.1 | His6 tag Adnectin core 11 sequence having AdNT1 and AdCT1 terminal sequences with | MGVSDVPRDLEVVAATPTSLLISWSKYSKH GHYYRITYGETGGNSPVQEFTVPSGNATAT ISGLKPGVDYTITVYAVEDTNDYPH THRPISINYRTEIDKPSQHHHHHH |
| 201 | SABA12.1 | His6 tag Adnectin core 12 | MGVSDVPRDLEVVAATPTSLLISWHGEPDQ TRYYRITYGETGGNSPVQEFTVPPYRRTAT ISGLKPGVDYTITVYAVTSGYTGHY |

TABLE 3-continued

Summary of SABA Exemplary Sequences

| SEQ ID NO: | Sequence Name | Description | Sequence |
|---|---|---|---|
| | | sequence having AdNT1 and AdCT1 terminal sequences with | QPISINYRTEIDKPSQHHHHHH |
| 202 | SABA13.1 | His6 tag Adnectin core 13 sequence having AdNT1 and AdCT1 terminal sequences with | MGVSDVPRDLEVVAATPTSLLISWSKYSKH GHYYRITYGETGGNSPVQEFTVDPSSYTAT ISGLKPGVDYTITVYAVSKDDYYPHEH RPISINYRTEIDKPSQHHHHHH |
| 203 | SABA14.1 | His6 tag Adnectin core 14 sequence having AdNT1 and AdCT1 terminal sequences with | MGVSDVPRDLEVVAATPTSLLISWYEPYTP IHYYRITYGETGGNSPVQEFTVPGYYGTAT ISGLKPGVDYTITVYAVYGYYQYTPISINY RTEIDKPSQHHHHHH |
| 204 | SABA15 | His6 tag core 15 sequence having AdNT1 and AdCT1 terminal sequences with His6 tag | MGVSDVPRDLEVVAATPTSLLISWSKYSKH GHYYRITYGETGGNSPVQEFTVPSGNATAT ISGLKPGVDYTITVYAVSDDNKYYH QHRPISINYRTEIDKPSQHHHHHH |
| 205 | SABA16.1 | Adnectin core 16 sequence having AdNT1 and AdCT1 terminal sequences with His6 tag | MGVSDVPRDLEVVAATPTSLLISWGHYRRS GHYYRITYGETGGNSPVQEFTVDPSSYTAT ISGLKPGVDYTITVYAVSKDDYYPHEH RPISINYRTEIDKPSQHHHHHH |
| 206 | SABA17.1 | Adnectin core 17 sequence having AdNT1 and AdCT1 terminal sequences with His6 tag | MGVSDVPRDLEVVAATPTSLLISWSKYSKH GHYYRITYGETGGNSPVQEFTVPSGNATAT ISGLKPGVDYTITVYAVEDTNDYPH THRPISINYRTEIDKPSQHHHHHH |
| 207 | SABA18.1 | Adnectin core 18 sequence having AdNT1 and AdCT1 terminal sequences with His6 tag | MGVSDVPRDLEVVAATPTSLLISWYEPGAS VYYYRITYGETGGNSPVQEFTVPSYYHTAT ISGLKPGVDYTITVYAVYGYYEYEPISINY RTEIDKPSQHHHHHH |
| 208 | SABA19.1 | Adnectin core 19 sequence having AdNT1 and AdCT1 terminal sequences with His6 tag | MGVSDVPRDLEVVAATPTSLLISWQSYYAH SDYYRITYGETGGNSPVQEFTVPYPPQTAT ISGLKPGVDYTITVYAVYAGSSYYPISINY RTEIDKPSQHHHHHH |
| 209 | SABA20.1 | Adnectin core 20 sequence having AdNT1 and AdCT1 terminal sequences with His6 tag | MGVSDVPRDLEVVAATPTSLLISWGHYRRS GHYYRITYGETGGNSPVQEFTVDPSSYTAT ISGLKPGVDYTITVYAVSKDDYYPHEH RPISINYRTEIDKPSQHHHHHH |
| 210 | SABA21.1 | Adnectin core 21 sequence having AdNT1 and AdCT1 terminal sequences with His6 tag | MGVSDVPRDLEVVAATPTSLLISWPEPGTP VYYYRITYGETGGNSPVQEFTVPAYYGTAT ISGLKPGVDYTITVYAVYGYYDYSPISINY RTEIDKPSQHHHHHH |
| 211 | SABA22.1 | Adnectin core 22 sequence having AdNT1 and AdCT1 terminal sequences with His6 tag | MGVSDVPRDLEVVAATPTSLLISWYRYEKT QHYYRITYGETGGNSPVQEFTVPPESGTAT ISGLKPGVDYTITVYAVYAGYEYPHT HRPISINYRTEIDKPSQHHHHHH |
| 212 | SABA23.1 | Adnectin core 23 sequence having AdNT1 and AdCT1 terminal sequences with His6 tag | MGVSDVPRDLEVVAATPTSLLISWVKSEEY YRYYRITYGETGGNSPVQEFTVPYYVHTAT ISGLKPGVDYTITVYAVTEYYYAGAVVSVP ISINYRTEIDKPSQHHHHHH |
| 213 | SABA24.1 | Adnectin core 24 sequence having AdNT1 and AdCT1 terminal sequences with His6 tag | MGVSDVPRDLEVVAATPTSLLISWYDPYTY GSYYRITYGETGGNSPVQEFTVGPYTTTAT ISGLKPGVDYTITVYAVSYYYSTQPISINY RTEIDKPSQHHHHHH |
| 214 | SABA25.1 | Adnectin core 25 sequence having AdNT1 and AdCT1 terminal sequences | MGVSDVPRDLEVVAATPTSLLISWSNDGPG LSYYRITYGETGGNSPVQEFTVPSSQTTAT ISGLKPGVDYTITVYAVSYYTKKAY SAGPISINYRTEIDKPSQHHHHHH |

TABLE 3-continued

Summary of SABA Exemplary Sequences

| SEQ ID NO: | Sequence Name | Description | Sequence |
|---|---|---|---|
| | | with His6 tag | |
| 215 | SABA26.1 | Adnectin core 26 sequence having AdNT1 and AdCT1 terminal sequences with His6 tag | MGVSDVPRDLEVVAATPTSLLISWPDPYYK PDYYRITYGETGGNSPVQEFTVPRDYTTAT ISGLKPGVDYTITVYAVYSYYGYYPISINY RT<u>EIDKPSQ</u>HHHHHH |

EXAMPLES

Example 1

Manufacturing Process

Fermentation and Harvest

A production fermentation is prepared with sterile basal medium. A vial is thawed and used to inoculate a transfer vessel containing growth medium. The inoculum is immediately transferred to the production fermentation. The culture is maintained at a temperature of 34° C. with agitation and allowed to grow to an $OD_{600}$ of 5-10 (one OD unit is approximately $1 \times 10^9$ cells/mL) is reached. The addition of feed medium is initiated at this OD. The fermentation proceeds to $OD_{600}$=25 at which point the culture is induced to produce the Adnectin by the addition of isopropyl β-D-1-thiogalactopyranoside (IPTG). The temperature of the vessel is increased from 34° C. to 39° C. at the time of induction. Samples are taken aseptically every hour and tested for cell density.

After 9-12 hrs of induced fermentation the vessel is prepared for harvest by reducing the temperature to 25° C., addition of ethylenediaminetetraacetic acid (EDTA) to a final concentration of 10 mM, pH increase to 7.8 by the addition of sodium hydroxide and reduction of agitation. After a one hour hold period the fermentor content is drained into a collection vessel.

Preparation of Inclusion Bodies

Cell disruption of the harvest pool is done by passing the material through a MICROFLUIDIZER® which disrupts the cells and the releases their contents. Following cell disruption the inclusion bodies are collected using a disc stack centrifuge to separate solids and liquid phases in a continuous process by extremely high centrifugal forces. Inclusion bodies are then washed twice with buffer (20-25° C.) and twice with water (20-25° C.). Each time the washed inclusion bodies are collected by centrifugation. The washed inclusion bodies are recovered as a slurry.

Solubilizaton of Inclusion Bodies and Protein Refolding

Solubilization buffer is added to the inclusion body slurry followed by stirring at room temperature for 1 hr. An $OD_{280}$=20 (total protein) is targeted during this process.

The protein refolding is performed using a two step dilution process. Dilution buffer is added to the solubilized inclusion bodies at a ratio of one part solubilized inclusion bodies to one half part dilution buffer (v/v). A second dilution is carried out by adding solubilized inclusion bodies to refold buffer to target an $OD_{280}$=0.7 (total protein). The dilutions are carried out while stirring at room temperature. Following thorough mixing for one hour, the stirring is stopped and the protein solution is held at room temperature overnight. The solubilized and refolded Adnectin is passed through a 0.8 μm-0.22 μm filter and tested for protein content by $A_{280}$ and RP-HPLC.

Purification and Conjugation to PEG

Refolded and filtered Adenctin is directly loaded onto a cation exchange (CEX1) column for initial capture. The bound material is washed with wash buffer and eluted with 50 mM sodium acetate, 500 mM sodium chloride, 1.5% propylene glycol, pH 5.5. The eluate pool is assayed for purity, identity, concentration, and endotoxin.

The eluate from the capture chromatography is further purified using hydrophobic interaction chromatography (HIC). The CEX1 eluate is directly loaded on the HIC column, washed and subsequently eluted with 50 mM sodium acetate, 30% propylene glycol, pH 5.5. The eluate pool is assayed for purity, identity and concentration.

The purified Adenctin is then formatted directly with a maleimide derivative of a 40 kDa branched PEG (mPEG2-MAL). The HIC eluate is stirred at room temperature and the mPEG2-MAL is added. After 1 hr of mixing at room temperature, the reaction mixture is allowed to incubate overnight at the same temperature. The PEGylation solution is then processed on the final CEX column (CEX2). Samples are taken for protein content, purity and endotoxin.

The pH and conductivity of the PEGylation solution are adjusted to 4.0 and 1.0 mS/cm respectively, with 75 mM acetic acid prior to loading on the final cation exchange column (CEX2) for repurification. Once loaded, the bound material is washed with buffer and subsequently eluted with 50 mM sodium acetate, 25 mM sodium chloride, pH 5.0. Samples are taken for protein content, purity and endotoxin.

The CEX2 eluate is concentrated to 15 mg/mL in a tangential flow filtration unit equipped with a 30 kDa nominal molecular weight cut off membrane with a V-screen. The bulk drug substance in 50 mM sodium acetate, 25 mM sodium chloride, pH 5.0. is passed through a 0.22 μm filter and frozen at −80° C.

Example 2

Gene, Vector and Host Cell

A plasmid encoding the protein under the control of the T7 promoter was generated for use in strain construction. This plasmid DNA was used to transform competent E. coli K-12 MG1655 cells (F-lambda-, ilvG-rfb-50 rph-1). The host strain was designed to allow induction of expression from genes upon addition of IPTG. The transformed MG1655 strain is resistant to kanamycin. The protein expression vector is shown in FIG. 2. A single colony selection from plates is used to inoculate a fermentation culture which is then aliquoted and frozen away to be used as a research cell bank.

Example 3

Biophysical and Biochemical Characterization

The structure and quality of the protein of the invention were examined by several comprehensive analytical methods.

MALDI-MS

Mass spectral profiles were analyzed by MALDI. To evaluate precision of MALDI analysis on the samples, 20 individual spots were placed onto the steel plate for each sample and analyzed sequentially. A total of 20 spectra were generated.

Peptide Mapping

Peptide mapping was used to confirm correct expression of the amino acid sequence (primary structure) predicted from the cDNA sequence for the protein of the invention as well as the corresponding unPEGylated protein. In order to obtain complete sequence coverage, trypsin (cleavage to C-terminal side of Lys and Arg residues) and endoproteinase Glu-C (cleavage to C-terminal side of Glu residues) were employed to yield two overlapping sets of peptide fragments. Peptide mapping was also used to determine covalent post-translational modifications including residual N-terminal methionine, disulfide-bridging, deamidation of asparagine, methionine oxidation (etc.). Peptides were identified and characterized by liquid chromatography mass spectrometry (LC-MS) via molecular weight and tandem mass spectrometry (MSMS) which provides partial sequence information via collision-induced dissociation (CID).

SDS-PAGE

Sodium dodecyl sulfate polyacrylamide gel electrophoresis (SDS-PAGE) was used to visualize molecular weight banding patterns of unPEGylated and PEGylated anit-IL-23 Adnectins. The samples were prepared in a sample buffer with or without a reducing agent. After heating in SDS, the samples and molecular weight markers were electrophoretically analyzed on pre-cast, gradient (4-20%) polyacrylamide gels. After electrophoresis, the gels were fixed and stained using Coomassie Blue. The equivalence of the banding patterns of samples was assessed visually.

Size-Exclusion Chromatography/Multi-Angle Light Scattering (SECMALS)

Size-exclusion chromatography (SEC) was used for the quantitative analysis of monomer, High Molecular Weight (HMW), and Low Molecular Weight (LMW) species. Following SEC separation, the molecular mass of separated species was determined by multi-angle light scattering in tandem with a differential refractometer.

Example 4

In Vitro Nonclinical Pharmacology $K_D$ by SPR

The binding characteristics were characterized by Surface Plasmon Resonance (SPR). Human IL-23 was immobilized at two to four levels in one dimension of a ProteOn XPR (Bio-Rad) chip surfaces and exposed to 6 different concentrations of anti-IL-23 adnectins in the other dimension of the same SPR chip surface. This allowed kinetic determination in the absence of regeneration. Duplicate chips were used for kinetic determinations at 25° C. and 37° C. Evaluation of the kinetic parameters was performed using the Langmuir interaction model and constant parameter fitting with the ProteOn Manager software.

As shown in Table 4 below, the off-rates for these anti-IL-23 adnectins are slow (on the order of $10^{-5}$ $s^{-1}$) at 25° C. Even at 37° C. the off rates were close to the limit of detection for SPR technologies so it is possible that the reported dissociation constant measurements are under-estimates.

TABLE 4

Kinetic Parameters of Anti-IL-23 Adnectin Against Directly Immobilized Human IL-23

| Anti-IL-23 adnectin | Analysis temp (° C.) | $k_{on}$ ($M^{-1}$ $s^{-1}$) | $k_{off}$ ($s^{-1}$) | $K_D$ (nM) |
|---|---|---|---|---|
| 1490B03 | 25 | 2.8 ± 0.6 E+04 | 8.2 ± 1.1 E−06 | 0.03 ± 0.002 |
| 1571G04 | 25 | 5.7 ± 0.6 E+04 | 1.2 ± 0.2 E−05 | 0.2 ± 0.05 |
| ATI000934 | 25 | 9.4E+03 | 1.8E−05 | 1.9 |
| ATI001014 | 25 | 9.4 ± 0.2 E+03 | 1.7 ± 0.3 E−05 | 1.8 ± 0.2 |
| ATI001047 | 25 | 1.3 ± 0.03 E+04 | 2 ± 0.1 E−05 | 1.6 ± 0.1 |
| ATI001045 | 25 | 1.5 ± 0.2 E+05 | 2.5 ± 0.4 E−05 | 0.17 ± 0.01 |
| ATI001045 | 37 | 2.03 ± 0.01 E+05 | 5.5 ± 0.6 E−05 | 0.27 ± 0.03 |

Solution Phase Affinity

The solution affinity of ATI001045 for human IL-23 was measured using a Kinetic Exclusion Assay (KinExA). In one format duplicate titrations of hIL-23 were performed for each of three concentrations. The relative unbound ATI001045 concentration was measured by capture on a human IL-23 solid matrix followed by detection with a fluorescently labeled antibody that recognizes the Adnectin scaffold. Due to technical limitations, the lowest concentration that could be tested was 0.75 nM. Hence, while the global $K_D$ analysis shown in Table 5, gives an estimate of 51 pM for the $K_D$, the affinity could be as low as single digit pM or as high as 150 pM within a 95% confidence interval.

TABLE 5

Solution Phase Affinity Measurements for ATI001045

| $K_D$ 95% confidence interval: | 51 pM |
|---|---|
| $K_D$ high | 153 pM |
| $K_D$ low | 1 pM |

The solution affinity of ATI001045 and ATI001047 for human IL-23 was also measured using an alternate format in the KinExA. Duplicate titrations of adnectins were performed for each of three (ATI001045) or single (ATI001047) concentrations of human IL-23 (quadruplicate for the lowest concentration). The relative unbound human IL-23 concentration was measured by capture on a non-PEGylated ATI001045 solid matrix followed by detection with a fluorescently labeled antibody that recognizes the p40 subunit of hIL-23. The global $K_D$ analysis shown in Table 6 gives a $K_D$ of 9.4 pM with a 95% confidence interval of 22-2.4 pM for ATI001045 and a $K_D$ of 36.3 pM with a 95% confidence interval of 60.1 to 19.4 pM.

TABLE 6

Solution Phase Affinity Measurements

| | ATI001045 | ATI001047 |
|---|---|---|
| $K_D$ 95% confidence interval: | 9.4 pM | 36.33 pM |
| $K_D$ high | 22 pM | 60.07 pM |
| $K_D$ low | 2.4 pM | 19.44 pM |

STAT3 Phosphorylation on Kit225 Cells

Parham et al. ("A receptor for the heterodimeric cytokine IL-23 is composed of IL-12Rbeta1 and a novel cytokine receptor subunit, IL-23R", *J. Immunol.*, 168(11):5699-5708 (Jun. 1, 2002)) cloned the IL-23R from the human IL-2 dependent T-cell line, Kit225. These cells have been characterized for expression of both IL-12RB1 and IL-23R by FACS analysis and responded to IL-23 by stimulation of pSTAT3 and to IL-12 by stimulation of pSTAT4. Kit225 cells were seeded into 96 well plates and quiesced in the absence of FBS and IL-2 for 3 hrs at 37° C. Following this incubation, human recombinant IL-23 (or IL-23 preincubated with antagonist for 1 hr) was applied and the cells returned to the incubator for 15 minutes at 37° C. to stimulate the phosphorylation of STAT3 (abbreviated as p-STAT3). Each condition was assayed in duplicate in 96-well plates. Stimulation was stopped by placing the cells on ice and addition of ice-cold PBS. Finally, the cells were pelleted and lysed following standard protocols and pSTAT3 production detected by ELISA.

The optimal concentration of IL-23 for stimulation was 35 pM Inhibition of the IL-23 induced pSTAT3 was demonstrated by a titration of anti-p40 monoclonal antibody (mAb1510) as well as an anti-p19 polyclonal antibody (AF1716). ATI001045, ATI001047, ATI001014 and ATI001016 had equivalent activity with an $IC_{50}$ of ~300 pM, approximately 150 fold more potent than the anti-p 19 polyclonal antibody while ATI001015 had an IC50 of ~1.2 nM, approximately 40 fold more potent than the anti-p19 polyclonal antibody. Adnectin ATI000934 is ⅓rd the potency of ATI001045, with an $IC_{50}$ of 1 nM (Table 7).

TABLE 7

Inhibition of IL-23 Induced STAT3 Phosphorylation by Anti-IL-23 Antagonists

| | pSTAT3 $IC_{50}$ ± SD (nM) |
|---|---|
| ATI001045 | 0.28 ± 0.14 |
| ATI001047 | 0.36 |
| ATI001014 | 0.3 ± 0.1 |
| ATI001015 | 1.24 |
| ATI001016 | 0.3 ± 0.1 |
| ATI000934 | 0.8 ± 0.2 |
| Anti-p40 (mAb1510) | 0.19 + 0.04 |
| anti-p19 (AF1716) | 52 ± 13 |

STAT3 Phosphorylation on Human PBMCs

A secondary cell-based confirmatory assay was developed with the goal of evaluating phosphorylation of STAT3 as a mechanism of action in primary human cells. Peripheral blood mononuclear cells (PBMC) from healthy donors consist primarily of naïve and quiescent T-cells that nominally express low levels of IL-23R and do not appreciably respond when stimulated with exogenous IL-23. However, polyclonal activation of naïve PBMC with IL-2 results in activation and differentiation of naïve T-cells with subsequent increased expression of IL-23R. These activated cells are then susceptible to stimulation with exogenous IL-23 which activates the STAT pathway, resulting in phosphorylation of STAT3.

Figure 4:
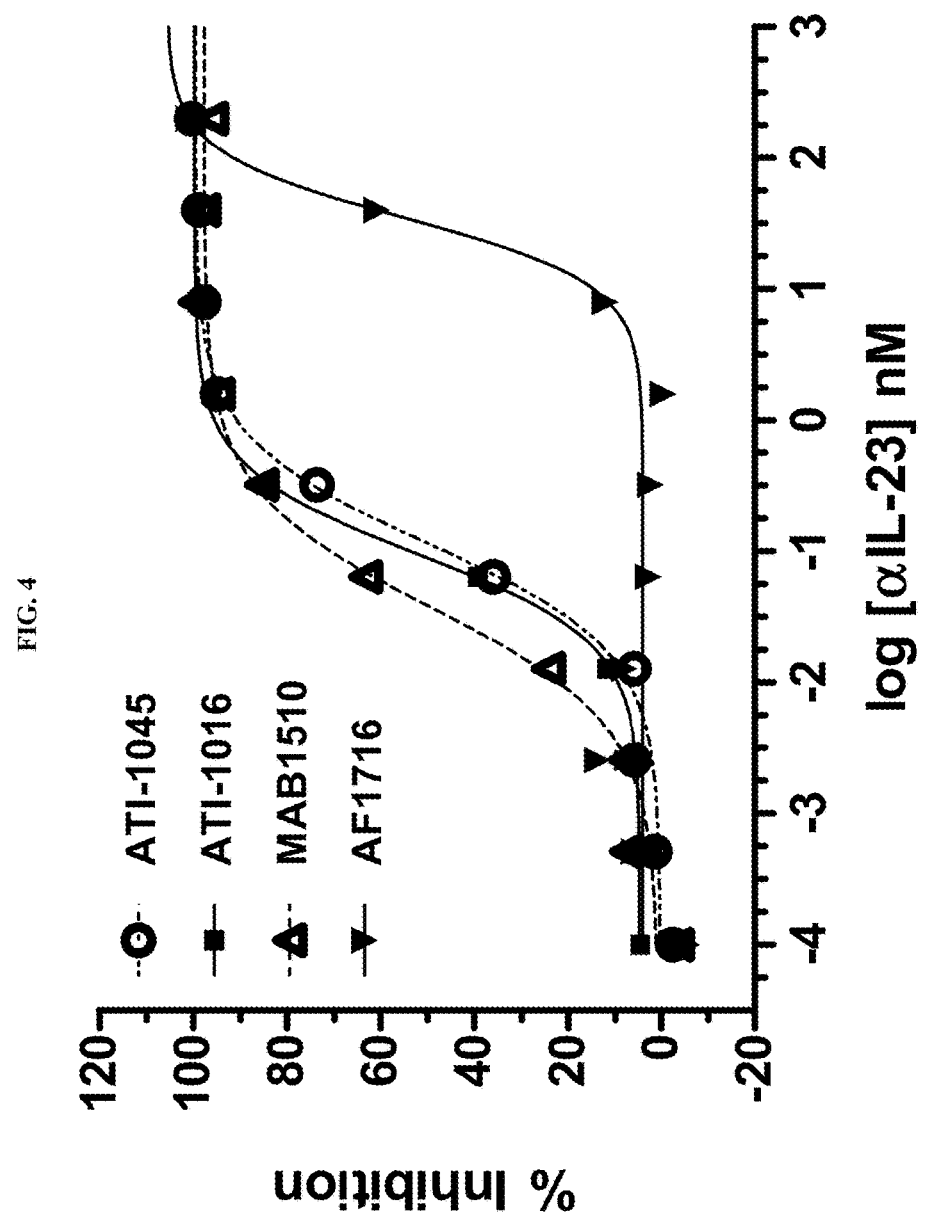
FIG. 4 shows a representative $IC_{50}$ curves from PBMC pSTAT3 inhibition by anti-IL-23 adnectin as described in Example 4.
Figure 5:
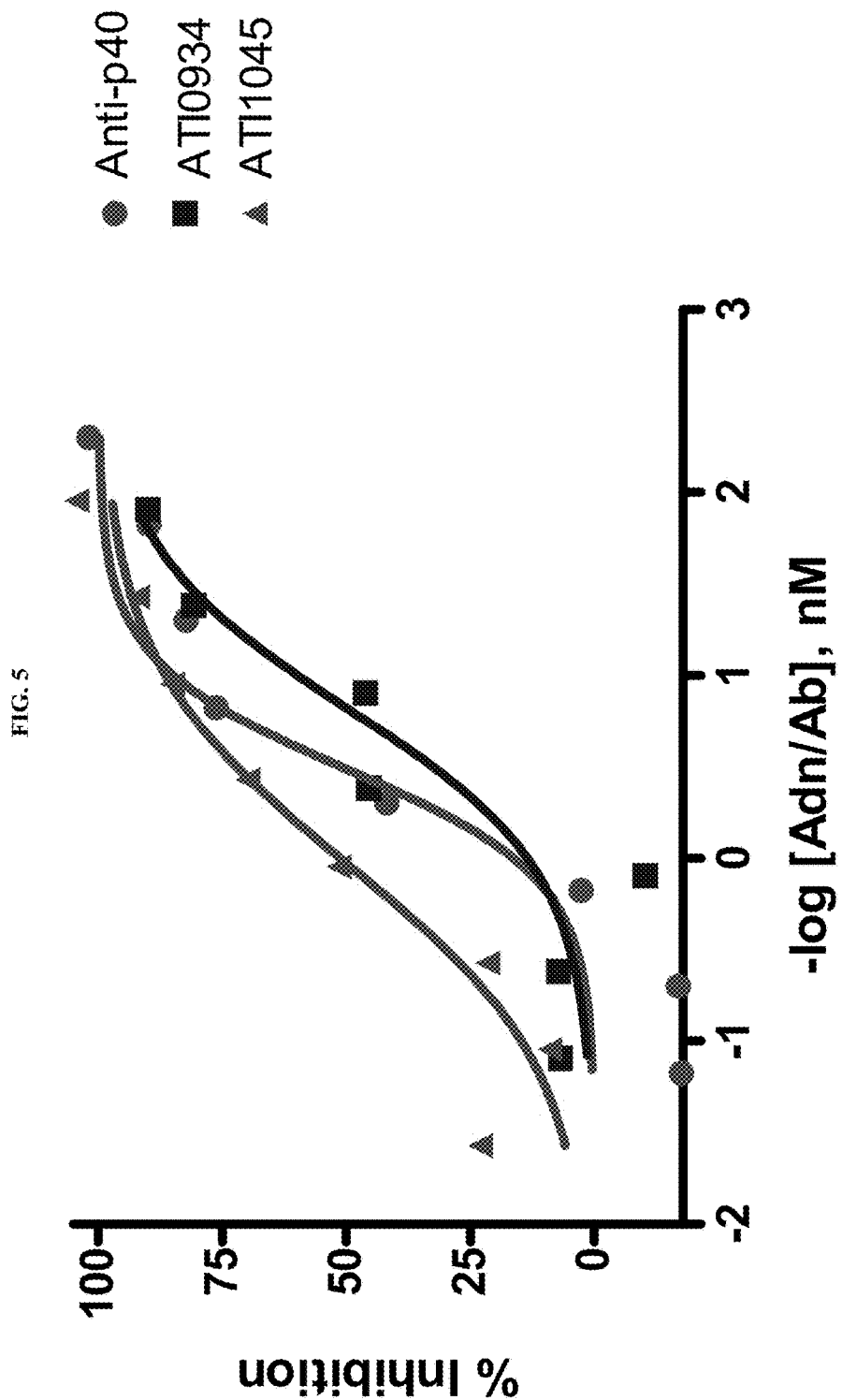
FIG. 5 shows a representative $IC_{50}$ curves for inhibition of IL-23-dependent IL-17A by anti-IL-23 adnectins and anti-p40 monoclonal antibody (MAB1510) as described in Example 4.

Commercially available antibodies (AF1716, an anti-p19 pAb and mAb1510, an anti-p40 mAb, both from R&D Systems) were used as positive controls for inhibition of IL-23 induced STAT3 phosphorylation. The inhibitory activity of six adnectins was compared in ten separate experiments using blood from multiple donors (summarized in Table 8). Exemplary data for a subset are shown in FIG. 4. The anti-IL-23 adnectins were significantly (>150-fold) more potent than the anti-p19 in inhibiting STAT3 phosphorylation but similar to 5 fold less potent than the anti-p40 monoclonal antibody.

TABLE 8

Inhibition of PBMC pSTAT3 by Anti-IL-23 Antagonists

| | pSTAT3 $IC_{50}$ ± SD (nM) |
|---|---|
| 1490B03 | 0.03 ± 0.02 |
| 1571G04 | 0.09 ± 0.06 |
| 1572G06 | 0.07 ± 0.02 |
| ATI 934 | 0.14 ± 0.12 |
| ATI 1016 | 0.06 ± 0.03 |
| ATI 1045 | 0.07 ± 0.03 |
| MAB1510 | 0.03 ± 0.04 |
| AF1716 | 21.4 ± 9.4 |

IL-23 Induced Cytokine Production by Mouse Splenocytes

Initial cellular assays with primary cells were designed to evaluate the capacity of anti-IL-23 adnectins to inhibit IL-23-dependent cytokine secretion from murine Th17 cells. To differentiate murine Th17 cells for analysis, CD4+ T cells were enriched with magnetic beads, co-cultured with irradiated splenocytes, and activated with anti-CD3 in presence of TGF-β and IL-6 and neutralizing antibodies for IL-4 and IFN-γ. After 6 days in culture, the polarized Th17 cells were harvested, re-seeded in a 96-well plate and stimulated with 100 ng/ml human IL-23 and 5 ng/ml murine IL-2. The addition of IL-2 was required to maintain cell viability and enable robust cytokine production in response to IL-23 but did not strongly induce IL-17A or IL-22 production alone. Because IL-2 induces a low level of cytokine secretion, each sample set included cells stimulated with IL-2 alone to control for baseline levels of cytokine produced in the absence of IL-23. The IL-23-dependent response was evaluated by calculating the difference between the level of cytokine induced by the combination of IL-2 and IL-23 and the baseline level induced by IL-2 alone. A dose range of adnectins were added during re-stimulation of the Th17 cells with IL-2 and IL-23 to test their inhibitory potential. A dose range of human anti-p40 antibody (R&D Systems MAB1510) was run in parallel as positive controls for assessing IL-23 inhibition. Each condition was tested in triplicate wells of a 96-well plate. After 4 days, the conditioned media from the triplicates was pooled, cleared of cellular debris, and assayed for both IL-17A and IL-22 concentrations by ELISA.

Stimulation of Th17 cells with IL-2 and IL-23 induced a 2- to 3-fold increase of IL-17A and at least a 5-fold enhancement of IL-22 compared to the levels induced by IL-2 alone. ATI000934, ATI001014, ATI001015, ATI001016, ATI001045 and the positive control anti-p40 monoclonal antibody mediated dose-dependent decreases in IL-23-dependent IL-17A and IL-22 secretion. $IC_{50}$ values for inhibition of both IL-17A and IL-22 secretion were calculated for each adnectin as well as the anti-p40 control and these data were summarized in Table 9. All of the adnectins tested were within 2-fold as potent as the anti-p40 control for inhibition of IL-23-dependent IL-17A secretion and within 2- to 3-fold as potent for inhibition of IL-23-dependent IL-22 production.

TABLE 9

Inhibition of IL-23-Dependent Cytokines by Anti-IL-23 Adnectins

| Adnectin/Ab | $IC_{50}$ ± S.D. IL-17 (nM) | $IC_{50}$ ± S.D. IL-22 (nM) |
|---|---|---|
| anti-p40 (MAB1510) | 2.3 ± 0.7 (n = 5) | 1.9 ± 0.7 (n = 5) |
| ATI000934 | 5.3 ± 1.6 (n = 2) | N.D. |

TABLE 9-continued

Inhibition of IL-23-Dependent Cytokines by Anti-IL-23 Adnectins

| Adnectin/Ab | $IC_{50} \pm S.D.$<br>IL-17 (nM) | $IC_{50} \pm S.D.$<br>IL-22 (nM) |
|---|---|---|
| ATI001045 | 1.3 ± 0.3 (n = 3) | 2.2 ± 1.1 (n = 3) |
| ATI001014 | 3.7 ± 0.0 (n = 2) | 6.5 ± 2.2 (n = 4) |
| ATI001015 | 2.0 ± 0.1 (n = 2) | 5.5 ± 2.4 (n = 4) |
| ATI001016 | 2.0 ± 2.0 (n = 4) | 3.0 ± 1.8 (n = 5) |

IL-23 Induced Cytokine Production by Human T Cells

Figure 6:
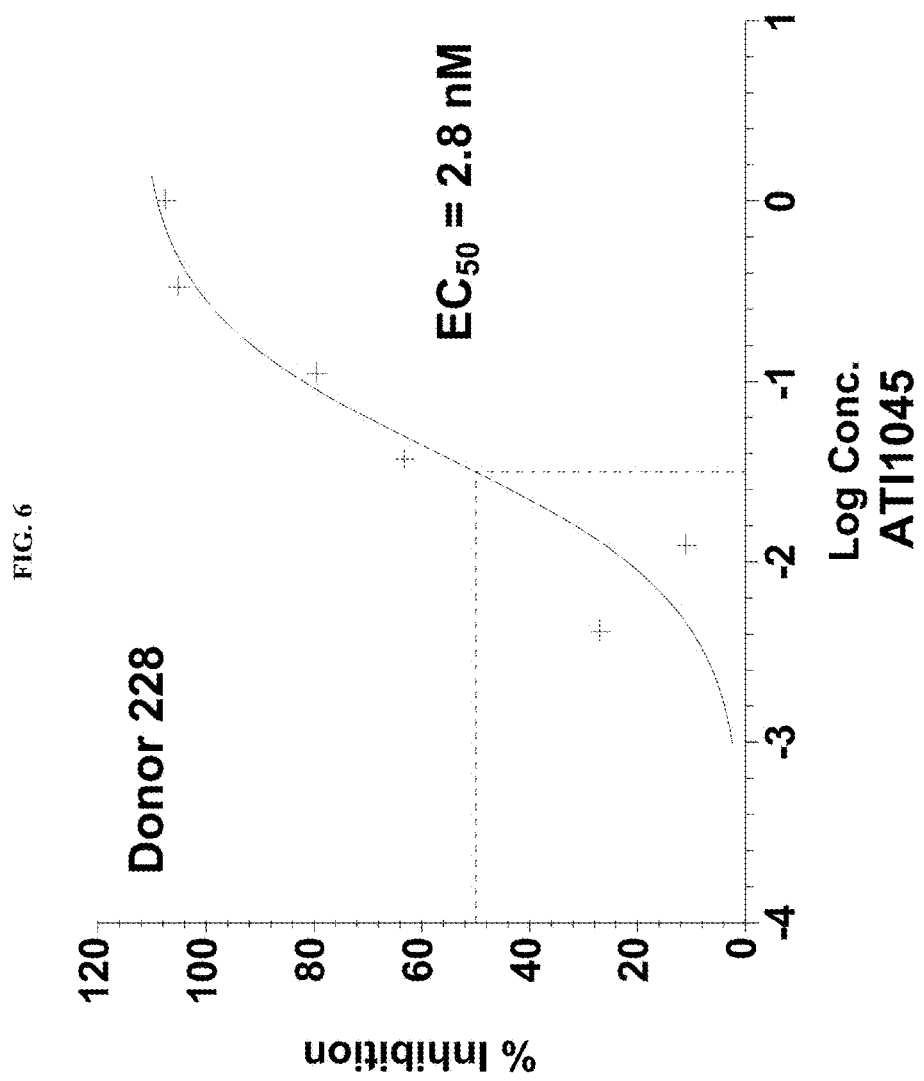
FIG. 6 shows ATI001045 inhibition of IL-23-induced IL-17 production by PBMCs of donor 228 (one of 4 donors tested as described in Example 4).

PBMCs were obtained by density-gradient separation of EDTA-treated whole blood from normal healthy donors. T cells were prepared from E+ fractions of PBMC rosetted with sheep red blood cells (SRBC). The T cells were plated at 100,000 cells per well into 96-well flat bottom plates that were coated with anti-CD3 (OKT at 10 ng/ml) for 1 hour at 37° C. and washed with PBS. Mixtures of RPMI-FCS media containing anti-CD28 (9.3 at 1 ng/ml) and IL-1β (10 ng/ml) or IL-1β+IL-23 (1 ng/ml) were prepared. This combination of cytokines has been shown to promote the differentiation of human T cells into IL-17-secreting T cells. ATI001045, starting concentration of 1 mg/ml was added to the mixture containing IL-1β+IL-23. IL-17 was detected in supernatants using DUOSET® ELISA development kits (R&D Systems). ATI001045 inhibited IL-17 production with an $EC_{50}$ of 2.0±1.6 nM (n=4 different donors), using the IL-1β alone as background. The commercial anti-p40 antibody (MAB1510) was used as an internal control and inhibited IL-17 production with an EC50 of 2.2±1.4 nM (n=3). Exemplary data from donor 228 is shown in FIG. 6.

Selectivity of Anti-IL-23 Adnectin for IL-23 Over IL-12

Figure 7:
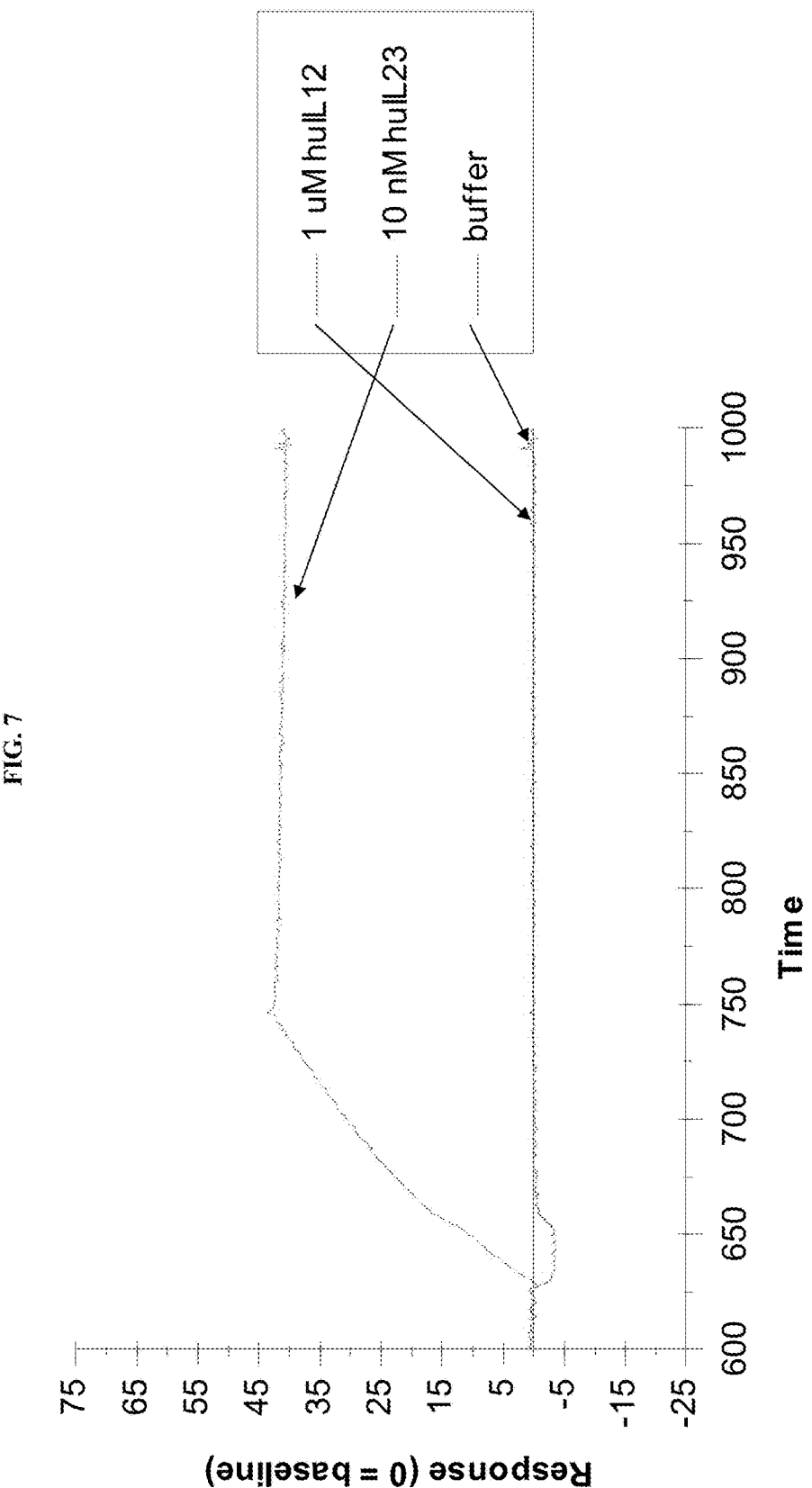
FIG. 7 shows representative selectivity data for the anti-IL-23 adnectins. Buffer subtracted sensorgrams illustrating the association and dissociation phases of 10 nM IL-23 and 1 uM IL-12 binding to captured ATI001016 as described in Example 4 are shown.

Adnectins listed in Table 2 as well as ATI001016 were used to examine the biochemical selectivity towards IL-23/IL-12. The binding analysis involved the capture of anti-IL-23 Adnectins on immobilized anti-His antibody followed by flow of IL-23 or IL-12 over the Adnectin. The selectivity of the Adnectins for IL-23 was assessed by comparing the binding signal for a 100 fold higher concentration of IL-12 over IL-23. Exemplary data in FIG. 7 shows that ATI001016 displayed robust binding (~40 RU) towards 10 nM human IL-23 while no detectable binding was observed for 1 μM human IL-12.

NK-92 cells are a human natural killer cell line known to respond to IL-12 in an IL-2 dependent fashion by secreting IFN-γ. Cells are typically washed to remove IL-2 then seeded into 96-well plates, then treated with 25 pM recombinant human IL-12 (or IL-12 preincubated with antagonists) and incubated for an additional 20 hours. Clarified supernatants are assayed for IFN-γ by ELISA.

Figure 8:
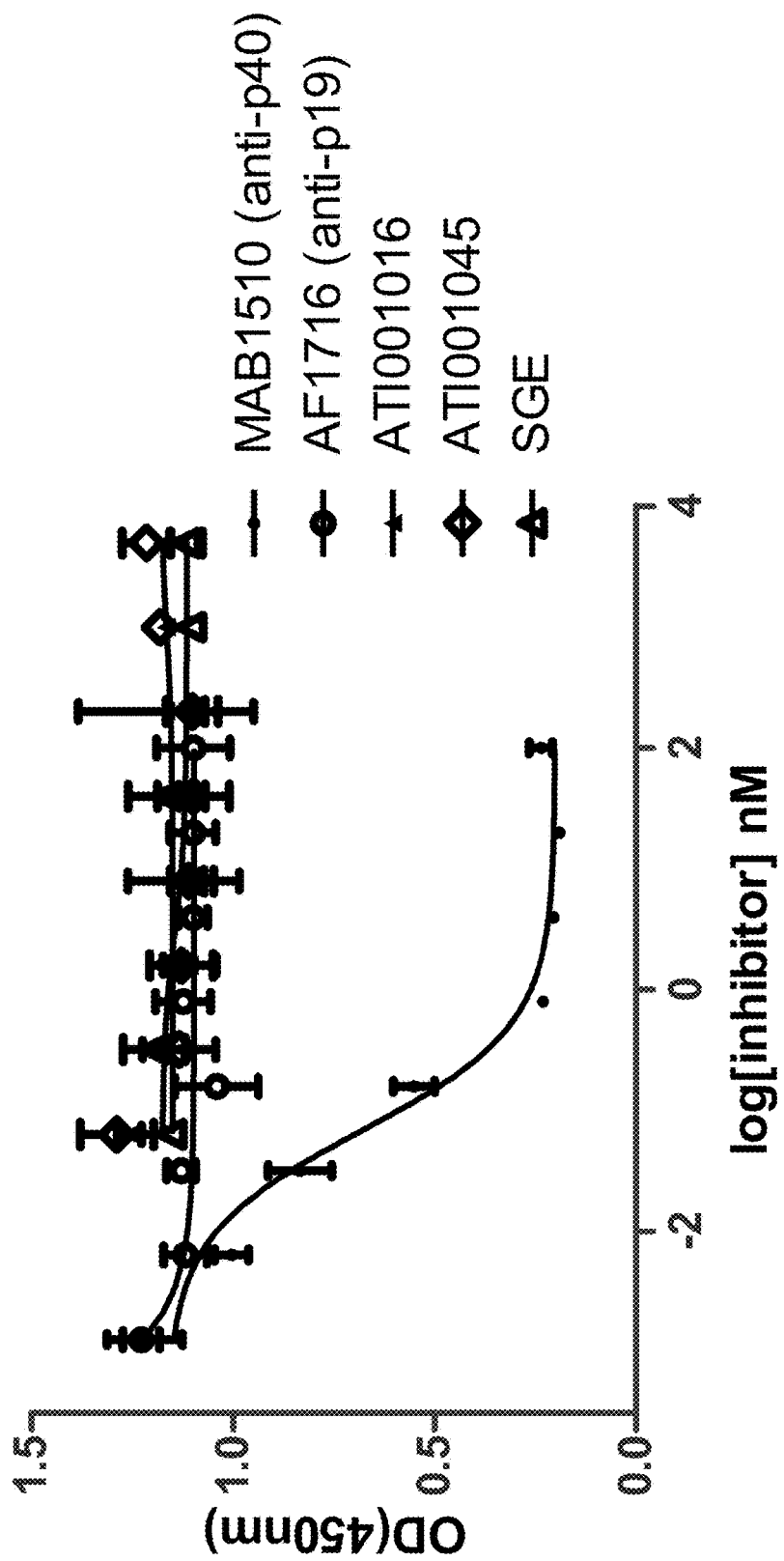
FIG. 8 shows that anti-IL-23 adnectins do not inhibit IL-12 induced IFN-γ production in NK-92 cells as described in Example 4.

A 4 point, 5 fold dilution series starting at 5 uM was prepared of each of the adnectin clones listed in Table 2 and incubated with 25 pM IL-12 for 30 minutes at 37° C. prior to the addition to NK-92 cells. A 12 point, 5 fold dilution series starting at 5 μM of ATI001045 and ATI001016 were incubated with 25 pM IL-12 for 30 minutes at 37° C. prior to the addition to NK-92 cells. None of the clones listed in Table 2 nor ATI001045 or ATI001016 detectably inhibited IFN-γ secretion at any of the concentrations tested demonstrating that these anti-IL-23 adnectins do not inhibit the interaction of IL-12 with the receptors on the surface of NK-92 cells. They appear equivalent to a negative control and 100 nM anti-p19 polyclonal antibody. As a positive control, anti-p40 monoclonal antibody (mAb1510) inhibited IL-12 induced IFN-γ secretion with an $IC_{50}$ of 0.07 nM (FIG. 8).

Anti-IL-23 Adnectin Block IL-23 Induced IL-17 in a Pharmacodynamic Model

Female C57B1/6 mice were injected intraperitoneally (IP) with recombinant murine IL-2 and human IL-23 according with the following schedule.

TABLE 10

Dosing and Injection Schedule

| | Time = −24 h | Time = 0 h | Time = 7 h | Time = 23 h |
|---|---|---|---|---|
| Murine IL-2 | 5 μg | 5 μg | 10 μg | 5 μg |
| Human IL-23 | 0 | 10 μg | 10 μg | 10 μg |

All mice were euthanized 7-8 hours following the final dose of IL-2 and IL-23 at Time=30 h. Serum was collected and assayed for IL-17 and IL-23 by ELISA.

Figure 9B:
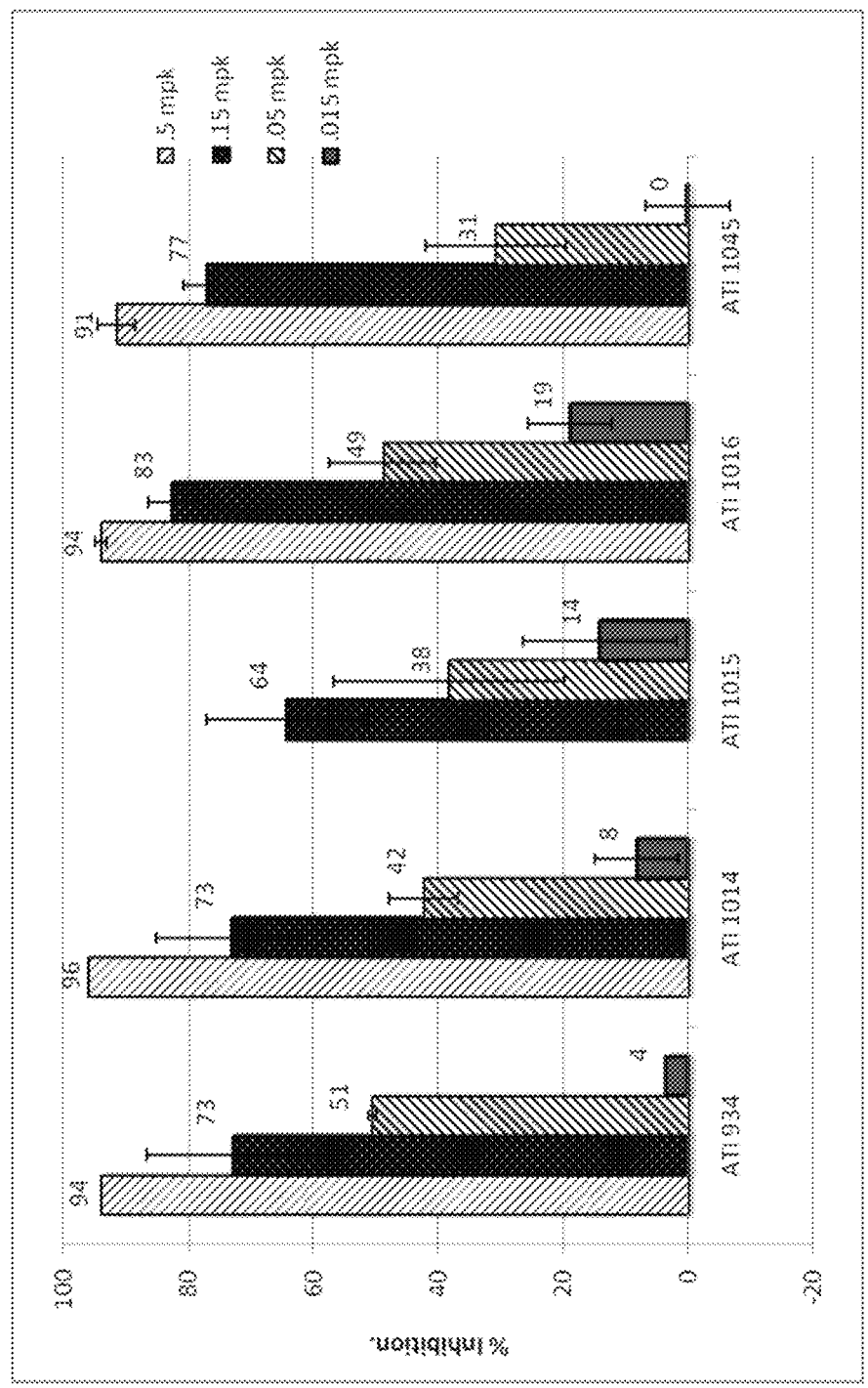
FIG. 9B shows a comparison of inhibitory activities of anti-IL-23 adnectins in a mouse pharmacodynamic model as described in Example 4.

Human IL-23 binds to the mouse receptor and induces the production of cytokines such as IL-17 and IL-22. Splenocytes from animals dosed intraperitoneally (IP) with IL-2 and human IL-23 secrete IL-17 when stimulated in culture ex vivo with anti-mouse CD3e. Significant levels of IL-17 can be detected in the serum of animals that were subjected to the treatment regimen described in Table 10 in which C57B1/6 mice are primed with IL-2 24 hours prior to 3 dual injections of IL-2+IL-23 over an additional span of 24 hours. Presumably, IL-2 polyclonally activates and expands Th populations in situ and up-regulates the expression of IL-23 receptor. This provides a method where the mechanisms of drug action and the relationship between drug concentration and effect in an in vivo setting can be investigated. The model was validated with an anti-p40 monoclonal antibody, mAb1510 (data not shown). In eight separate experiments, five anti-IL-23 adnectins were tested for their ability to inhibit the production of murine IL-17 when dosed SC at 0.5, 0.15, 0.05 and 0.015 mg/kg 2 hours prior to the initial dose of IL-2+IL-23 in eight separate experiments. Exemplary dose response data for ATI001045 is shown in FIG. 9a (calculated average ED50 of 0.03 mg/kg). All anti-IL-23 adnectins tested showed dose dependent inhibition of human IL-23 murine IL-17 production in serum though the extent of inhibition was variable across adnectins.

Activity of Anti-IL-23 Adnectin in the IL-23 Induced Skin Acanthosis Model

The intra-dermal injection of IL-23 into the skin of the back or into the external ear pinna of mice induces dermal inflammation and hyperplasia of the epidermis (acanthosis) (Zheng, Y., "Interleukin-22, a TH17 cytokine, mediates IL-23-induced dermal inflammation and acanthosis", *Nature*, Vol. 445/8 (February 2007)). In these studies, recombinant human IL-23 (rHuIL-23) was injected into mouse ears to explore the downstream consequences of aberrant cutaneous IL-23 exposure.

Six to eight week old C57BL/6 female mice were injected with 5 ug of dual chain, recombinant, human IL-23 into the right ear every other day until Day 12. PBS was injected into the contra-lateral ear as a control. In one study, treatment with ATI001045 began approximately 2 hours before the first IL-23 injection and continued 3 times per week until Day 12. ATI001045 was administered SC at doses of 0.1, 0.3, 1, 3 mg/kg. In a second study vehicle or ATI000934-123 (1753E02) was administered IP at 1, 3, or 10 mg/kg approximately 1 hour prior to IL-23 administration and 3 times per week thereafter until Day 10. Anti-HuIL-12/IL-23 p40 Antibody (R&D mAb1510) at 10 mg/kg was given IP on Day 0 and 4 as a positive control. Ear thickness (in thousandths of an inch) was measured every-other-day, prior to the next ear injection, using a MITUTOYO® (#2412F) dial caliper. Ear thickness was calculated by subtracting the value of the control ear from the measurement for the IL-23 injected ear for each animal At the end of the study (Day 14 for ATI001045 and Day 12 for ATI000934), following euthanasia with $CO_2$ gas, ears were excised at the hairline and formalin fixed/paraffin-embedded tissues were examined histologically on H&E stained slides.

Figure 10A:
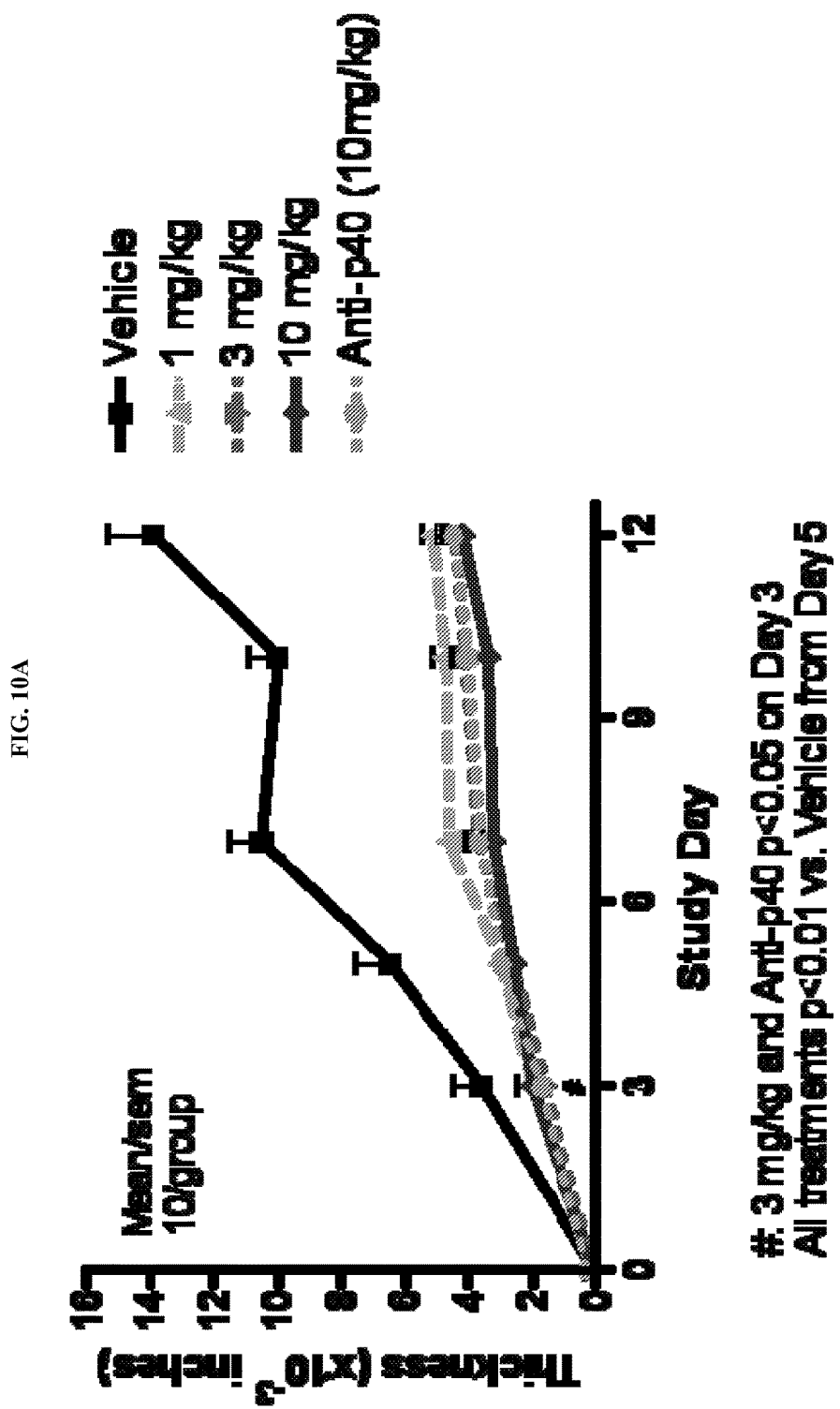
FIG. 10A shows ATI000934 dose response in human IL-23 induced acanthosis as described in Example 4.
Figure 10B:
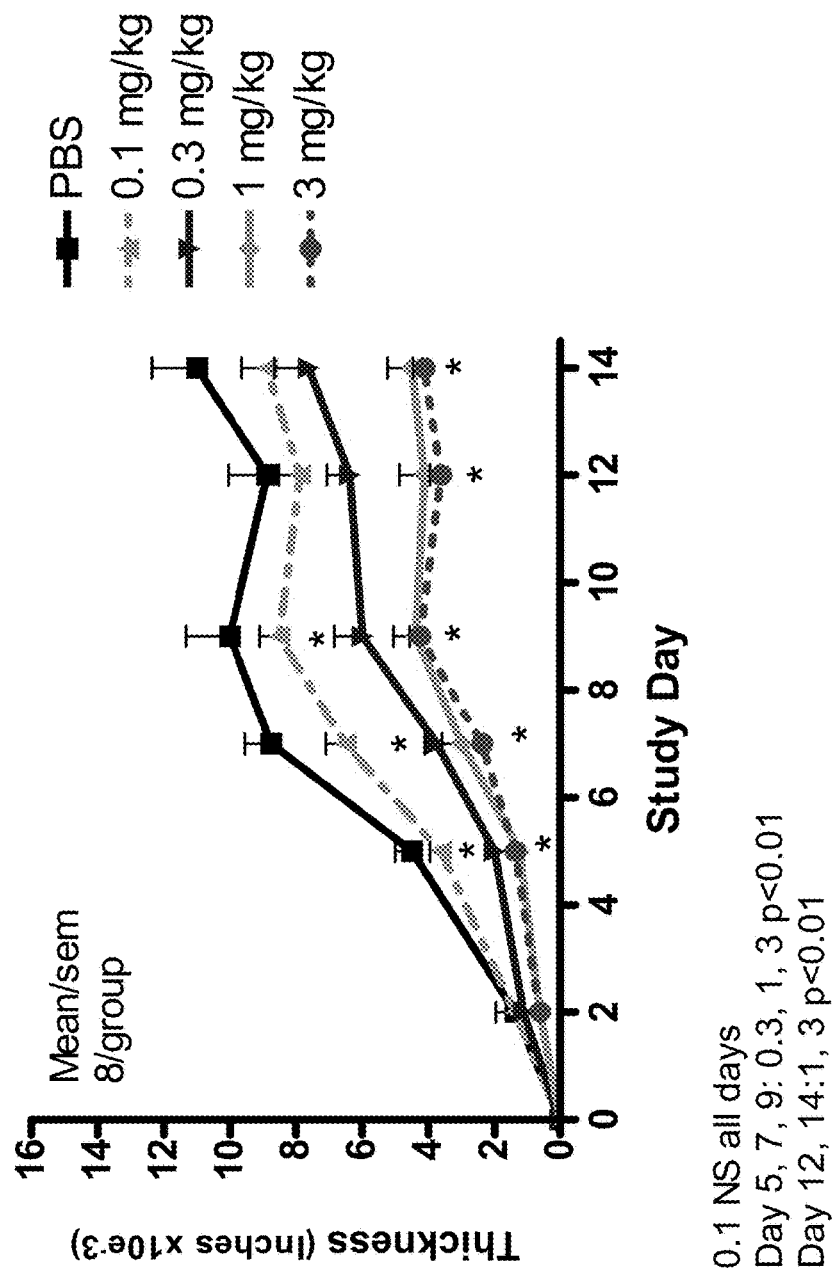
FIG. 10B shows ATI001045 Dose Response in Human IL-23-Induced acanthosis as described in Example 4.

Overall, doses of 1, 3, and 10 mg/kg of ATI000934 provided a similar level of inhibition of IL-23-induced ear thickening in this study (FIG. 10). Ear thickness in all treatment groups was significantly (p<0.01 ANOVA/Dunnett's) less than Vehicle, including the anti-p40 group, from Day 5 through the end of the study on Day 12. On Day 12, terminal plasma samples were obtained 48 hours post last dose and analyzed for circulating levels of ATI000934 which were determined to be 11, 18, 36 ug/ml respectively.

Following the last measurement on Day 12, ears were collected at necropsy for routine histologic examination from 10 animals per group. The majority of animals administered ATI000934 had acanthosis and dermal infiltrates, but the histologic severity score was reduced from that observed in vehicle treated animals. There was no apparent dose response. All of the animals administered anti-p40 also had acanthosis and dermal infiltrates, but the histologic severity score was also reduced from that observed in vehicle treated animals.

ATI001045 (1 mg/kg and 3 mg/kg) dose-dependently reduced ear thickness compared to Vehicle (PBS) treated animals from Day 5 through Day 14 (p<0.01 vs. Vehicle ANOVA/Dunnett's, FIG. 10). In contrast, the 0.1 mg/kg dose level was not statistically different (p>0.05) from Vehicle treatment on any study day. Treatment with 0.3 mg/kg provided intermediate reduction that was statistically less than Vehicle on Days, 5, 7, 9. Serum samples collected 48 hours post last dose were evaluated for circulating levels of ATI001045 which were determined to be 0.698, 2.72, 8, 22.5 ug/ml for doses of 0.1, 0.3, 1, 3 mg/kg respectively. Histological analysis revealed that administration of ATI001045 resulted in a dose dependent reduction of IL-23 induced cellular infiltrates and acanthosis which correlated with the ear thickness score.

Example 5

Material and Methods Used Herein

High Throughput Protein Production (HTPP)

Selected binders were cloned into pET9d vector and transformed into *E. coli* BL21 DE3 plysS cells were inoculated in 5 ml LB medium containing 50 μg/mL kanamycin in a 24-well format and grown at 37° C. overnight. Fresh 5 ml LB medium (50 μg/mL kanamycin) cultures were prepared for inducible expression by aspiration 200 μl from the overnight culture and dispensing it into the appropriate well. The cultures were grown at 37° C. until A600 0.6-0.9. After induction with 1 mM isopropyl-β-thiogalactoside (IPTG) the culture was expressed for 6 hours at 30° C. and harvested by centrifugation for 10 minutes at 2750 g at 4° C.

Cell pellets (in 24-well format) were lysed by resuspension in 450 μl of Lysis buffer (50 mM $NaH_2PO_4$, 0.5 M NaCl, 1× Complete Protease Inhibitor Cocktail-EDTA free (Roche), 1 mM PMSF, 10 mM CHAPS, 40 mM Imidazole, 1 mg/ml lysozyme, 30 μg/ml DNAse, 2 μg/mlaprotonin, pH 8.0) and shaken at room temperature for 1-3 hours. Lysates were clarified and re-racked into a 96-well format by transfer into a 96-well Whatman GF/D UNIFILTER® fitted with a 96-well, 1.2 ml catch plate and filtered by positive pressure. The clarified lysates were transferred to a 96-well Ni-Chelating Plate that had been equilibrated with equilibration buffer (50 mM $NaH_2PO_4$, 0.5 M NaCl, 40 mM Imidazole, pH 8.0) and was incubated for 5 min. Unbound material was removed by positive pressure. The resin was washed 2×0.3 ml/well with Wash buffer #1 (50 mM $NaH_2PO_4$, 0.5 M NaCl, 5 mM CHAPS, 40 mM Imidazole, pH 8.0) with each wash removed by positive pressure. Prior to elution each well was washed with 50 μl Elution buffer (PBS+20 mM EDTA), incubated for 5 min and this wash was discarded by positive pressure. Protein was eluted by applying an additional 100 μl of Elution buffer to each well. After a 30 minute incubation at room temperature the plate(s) were centrifuged for 5 minutes at 200 g and eluted protein is collected in 96-well catch plates containing 5 μl of 0.5M MgCl2 added to the bottom of elution catch plate prior to elution. Eluted protein was quantified using a total protein assay (BCA) with SGE as the protein standard.

Midscale Expression and Purification of Insoluble Fibronectin-Based Scaffold Protein Binders For expression, selected clone(s), followed by the HIS6tag, were cloned into a pET9d vector and were expressed in *E. coli* BL21 DE3 plysS cells. Twenty ml of an inoculum culture (generated from a single plated colony) was used to inoculate 1 liter of LB medium or TB-Overnight Expression Media (auto induction) containing 50 μg/ml Kanamycin and 34 μg/ml chloramphenicol. Cultures in LB medium were incubated at 37° C. until A600 0.6-1.0 at which time they then induced with 1 mM isopropyl-β-thiogalactoside (IPTG) and grown for 4 hours at 30° C. Cultures grown in TB-Overnight Expression Media were incubated at 37° C. for 5 hours at which time the temperature was lowered to 18° C. grown fir 19 hours. Cultures were harvested by centrifugation for 30 minutes at 10,000 g at 4° C. Cell pellets were frozen at −80° C. the cell pellet was resuspended in 25 ml of lysis buffer (20 mM $NaH_2PO_4$, 0.5 M NaCl, 1× Complete Protease Inhibitor Cocktail-EDTA free (Roche), pH 7.4) using an ULTRA-TURRAX® homogenizer (IKA works) on ice. Cell lysis was achieved by high pressure homogenization (18,000 psi) using a Model M-110S MICROFLUIDIZER® (Microfluidics). The insoluble fraction was separated by centrifugation for 30 minutes at ≥23,300 g at 4° C. The insoluble pellet recovered from centrifugation of the lysate was washed with 20 mM sodium phosphate/500 mM NaCl, pH7.4. The pellet was resolubilized in 6.0M guanidine hydrochloride in 20 mM sodium phosphate/500 mM NaCl pH 7.4 with sonication followed by incubation at 37 degrees for 1-2 hours. The resolubilized pellet was filtered to 0.45 μm and loaded onto a HISTRAP® column equilibrated with the 20 mM sodium phosphate/500 mM NaCl/6.0M guanidine pH7.4 buffer. After loading, the column was washed for an additional 25 CV with the same buffer. Bound protein was eluted with 50 mM Imidazole in 20 mM sodium phosphate/500 mM NaCl/6.0M guan-HCl pH7.4. The purified protein was refolded by dialysis against 50 mM sodium acetate/150 mM NaCl pH 4.5 or PBS pH 7.2.

Midscale Expression and Purification of Soluble Fibronectin-Base Scaffold Protein Binders As an alternative to purification of insoluble binders, the purification of soluble binders may also be used. For expression, selected clone(s), followed by the HIS6tag, were cloned into a pET9d vector and were expressed in *E. coli* BL21 DE3 plysS cells. Twenty ml of an inoculum culture (generated from a single plated colony) was used to inoculate 1 liter of LB medium or TB-Overnight Expression Media (auto induction) containing 50 μg/ml Kanamycin and 34 μg/ml chloramphenicol. Cultures in LB medium were incubated at 37° C. until A600 0.6-1.0 at which time they were then induced with 1 mM isopropyl-β-thiogalactoside (IPTG) and grown for 4 hours at 30° C. Cultures grown in TB-Overnight Expression Media were incubated at 37° C. for 5 hours at which time the temperature was lowered to 18° C. grown fir 19 hours. Cultures were harvested by centrifugation for 30 minutes at 10,000 g at 4° C. Cell pellets are frozen at −80° C. The cell pellet is resuspended in 25 ml of lysis buffer (20 mM $NaH_2PO_4$, 0.5 M NaCl, 1× Complete Protease Inhibitor Cocktail-EDTA free (Roche), pH 7.4) using an ULTRA-TURRAX® homogenizer (IKA works) on ice. Cell lysis is achieved by high pressure homongenization (≥18,000 psi) using a Model M-110S MICROFLUIDIZER® (Microfluidics). The soluble fraction is separated by centrifugation for 30 minutes at ≥23,300 g at 4° C. The supernatant is clarified via 0.45 μm filter. The clarified lysate is loaded onto a HISTRAP® column (GE) pre-equilibrated with the 20 mM sodium phosphate/500 mM NaCl pH 7.4. The column is then washed with 25 column volumes of the same buffer, followed by 20 column volumes of 20 mM sodium phosphate/500 mM NaCl/25 mM Imidazole, pH 7.4 and then 35 column volumes of 20 mM sodium phosphate/500 mM NaCl/40 mM Imidazole, pH 7.4. Protein is eluted with 15 column volumes of 20 mM sodium phosphate/500 mM NaCl/500 mM Imidazole, pH 7.4, fractions are pooled based on absorbance at A280 and are dialyzed against 1×PBS, 50 mM Tris, 150 mM NaCl. pH 8.5 or 50 mM NaOAc; 150 mM NaCl; pH4.5. Any precipitate is removed by filtering at 0.22 mm.

Fibronectin-based scaffold proteins (Adnectins) can be pegylated with various sizes and types of PEG. To allow for pegylation, the naturally occurring residues EIDKPSQ, found at the C-terminus end of 10FN3 proteins can be modified by a single point mutation of an amino acid, typically a serine, to a cysteine. PEGylation of the protein at the single cysteine residue is accomplished by conjugating various maleimide-derivatized PEG forms, combining the PEG reagent with the protein solution and incubating. An alternative method is to replace the EIDKPSQ tail with a GSGC linker, and similarly use the cysteine residue for PEGylation. Adnectins containing an engineered cysteine residue were conjugated with PEG via Michael-addition chemistry between the thiol group on the cysteine and the maleimide functional group of the PEG reagent. Briefly, 40 kDa PEG is added in a molar excess to protein solution under slightly acidic to neutral conditions. The reaction is allowed to proceed at room temperature for 2 hours to overnight. The reaction is then applied to an ion exchange column to separate the PEGylated Adnectin from the unreacted PEG-maleimide and non-PEGylated Adnectin. SE/HPLC methods may also be used. The purified PEGylated Adnectin is typically analyzed by SDS-PAGE and size exclusion chromatography.

Example 6

Screening and Selection of Candidate Serum Albumin-Binding Adnectin (SABA)

A selection technique known as PROfusion (see, e.g., Roberts et al., *Proc. Natl. Acad. Sci. USA*, 94(23):12297-12302 (1997) and WO 2008/066752) was applied to a DNA library with variable regions designed into the BC, DE and FG loops of $^{10}Fn3$. A random library of greater than $10^{13}$ molecules was created from this design, and selection pressure was applied against a biotinylated form of HSA to isolate candidate serum albumin-binding Adnectin (SABA) with desirable binding properties.

High Throughput Protein Production (HTTP) Process

The various HSA binding Adnectins were purified using a high throughput protein production process (HTPP). Selected binders were cloned into pET9d vector containing a HIS6 tag and transformed into *E. coli* BL21(DE3)pLysS cells. Transformed cells were inoculated in 5 ml LB medium containing 50 μg/mL Kanamycin in a 24-well format and grown at 37° C. overnight. Fresh 5 ml LB medium (50 μg/mL Kanamycin) cultures were prepared for inducible expression by aspirating 200 μl from the overnight culture and dispensing it into the appropriate well. The cultures were grown at 37° C. until $A_{600}$ 0.6-0.9. After induction with 1 mM isopropyl-β-thiogalactoside (IPTG), the culture was grown for another 4 hours at 30° C. and harvested by centrifugation for 10 minutes at 3220×g at 4° C. Cell Pellets were frozen at −80° C.

Cell pellets (in 24-well format) were lysed by resuspension in 450 μl of Lysis buffer (50 mM $NaH_2PO_4$, 0.5 M NaCl, 1× Complete Protease Inhibitor Cocktail-EDTA free (Roche), 1 mM PMSF, 10 mM CHAPS, 40 mM Imidazole, 1 mg/ml lysozyme, 30 ug/ml DNAse, 2 ug/ml aprotonin, pH 8.0) and shaken at room temperature for 1 hour. Lysates were clarified and re-racked into a 96-well format by transfer into a 96-well Whatman GF/D UNIFILTER® fitted with a 96-well, 650 μl catch plate and centrifuged for 5 minutes at 200×g. The clarified lysates were transferred to a 96-well Ni-Chelating Plate that had been equilibrated with equilibration buffer (50 mM $NaH_2PO_4$, 0.5 M NaCl, 10 mM CHAPS, 40 mM Imidazole, pH 8.0) and incubated for 5 min. Unbound material was removed. The resin was washed 2×0.3 ml/well with Wash buffer #1 (50 mM $NaH_2PO_4$, 0.5 M NaCl, 5 mM CHAPS, 40 mM Imidazole, pH 8.0). Next the resin was washed with 3×0.3 ml/well with PBS. Prior to elution each well was washed with 50 μl Elution buffer (PBS+20 mM EDTA), incubated for 5 min and this wash discarded by vacuum. Protein was eluted by applying an additional 100 ul of Elution buffer to each well. After 30 minute incubation at room temperature the plate(s) were centrifuged for 5 minutes at 200×g and eluted protein collected in 96-well catch plates containing 5 μl of 0.5M $MgCl_2$ affixed to the bottom of the Ni-plates. Eluted protein was quantified using a BCA Protein assay with SGE (control Adnectin) as the protein standard. The SGE Adnectin is a wild-type $^{10}Fn3$ domain (SEQ ID NO: 1) in which integrin binding domain (amino acids RGD at positions 78-80) have been replaced with SGE.

HSA, RhSA and MuSA Direct Binding ELISA

For assaying direct binders to HSA, MaxiSorp plates (Nunc International, Rochester, N.Y.) were coated with 10 ug/mL HSA (Sigma, St. Louis, Mo.) in PBS at 4° C. overnight followed by blocking in casein block buffer (Thermo Scientific, Rockford, Ill.) for 1-3 hours at room temperature. For single-point screening assays, purified HTPP Adnectin were diluted 1:20 in casein block buffer and allowed to bind to HSA in each well for 1 hour at room temperature. For dose response assays, concentrations ranging from 0.1 nM up to 1 μM were used. After washing in PBST to remove unbound Adnectins, anti-His mAb-HRP conjugate (R&D Systems, MN) diluted 1:2500 in casein block buffer was added to the bound His-tagged Adnectin for 1 hour at room temperature. Excess conjugate was removed by washing with PBST and bound Adnectins detected using TMB detection reagents (BD Biosciences) according to the manufacturer's instructions.

Identification of Candidate Serum Albumin-Binding Adnectin (SABA)

As a result of the screening for HSA/RhSA/MuSA binding and biophysical criteria, four unique serum albumin-binding Adnectins (SABA) were identified and chosen to have their half-lives evaluated in mice. In order to carry out in vitro and in vivo characterization, midscales were undertaken for the four SABAs. Table 3 provides the sequences of twenty-six unique SABA core sequences identified from PROfusion, designated as SABA 1-26. SABA4 had a scaffold mutation that was fixed prior to midscaling. The scaffold-perfect version of SABA4 is SABA5. SABA4 and SABA5 have identical sequences in the BC, DE, and FG loops.

Example 7

Production and Formulation of Candidate SABAs

Midscale Protein Production of SABAs

The selected SABAs followed by the $His_6$tag, were cloned into a pET 9d vector and expressed in *E. coli* BL21(DE3)pLysS cells (see Table 3 for each His-tagged SABA sequence designated SABA1.1, SABA2.1, SABA3.1, and SABA5.1). 20 ml of an inoculum culture (generated from a single plated colony) was used to inoculate 1 liter of LB medium containing 50 µg/mL Kanamycin. The culture was grown at 37° C. until $A_{600}$ 0.6-1.0. After induction with 1 mM isopropyl-β-thiogalactoside (IPTG) the culture was grown for another 4 hours at 30° C. and harvested by centrifugation for 30 minutes at ≥10,000×g at 4° C. Cell Pellets were frozen at −80° C. The cell pellet was resuspended in 25 mL of lysis buffer (20 mM $NaH_2PO_4$, 0.5 M NaCl, 1× Complete Protease Inhibitor Cocktail-EDTA free (Roche), pH 7.4) using an ULTRA-TURRAX® homogenizer (IKA works) on ice. Cell lysis was achieved by high pressure homogenization (≥18,000 psi) using a Model M-110S MICROFLUIDIZER® (Microfluidics). The soluble fraction was separated by centrifugation for 30 minutes at 23,300×g at 4° C. The supernatant was clarified via 0.45 µm filter. The clarified lysate was loaded onto a HISTRAP® column (GE) pre-equilibrated with 20 mM $NaH_2PO_4$, 0.5 M NaCl, pH 7.4. The column was then washed with 25 column volumes of 20 mM $NaH_2PO_4$, 0.5 M NaCl, pH 7.4, followed by 20 column volumes of 20 mM $NaH_2PO_4$, 0.5 M NaCl, 25 mM imidazole pH 7.4, and then 35 column volumes of 20 mM $NaH_2PO_4$, 0.5 M NaCl, 40 mM imidazole pH 7.4. Protein was eluted with 15 column volumes of 20 mM $NaH_2PO_4$, 0.5 M NaCl, 500 mM imidazole pH 7.4, fractions pooled based on absorbance at $A_{280}$ and dialyzed against 1×PBS, 50 mM Tris, 150 mM NaCl pH 8.5 or 50 mM NaOAc; 150 mM NaCl; pH 4.5. Any precipitate was removed by filtering at 0.22 µm.

Midscale expression and purification yielded highly pure and active Adnectins that were expressed in a soluble form and purified from the soluble fraction of the bacterial cytosol. SEC analysis on a SUPERDEX® 200 or SUPERDEX® 75 10/30GL in a mobile phase of 100 mM $NaPO_4$, 100 mM $NaSO_4$, 150 mM NaCl, pH 6.8 (GE Healthcare) demonstrated predominantly monomeric Adnectins.

Formulation of SABA1.2

One specific SABA, SABA1.2 (SEQ ID NO: 180), was chosen for a preliminary formulation screen. SABA1.2 comprises an $(ED)_5$ extension on the "core 1" sequence of $^{10}Fn3$. For SABA1.2, a stable formulation of 10 mM succinic acid, 8% sorbitol, 5% glycine at pH 6.0 and at a product concentration of 5 mg/mL was identified. In this formulation the protein melting temperature was 75° C. as determined by Differential Scanning calorimetry (DSC) using a protein concentration of 1.25 mg/mL. The formulation provided satisfactory physical and chemical stability at 4° C. and 25° C., with an initial aggregate level at 1.2%. After one month of stability, the level of aggregation was very low (1.6% at 4° C. and 3.8% at 25° C.). The protein was also stable in this formulation after five cycles of freeze-thaw as transitioned from −80° C. and −20° C. to ambient temperature. In addition, in this formulation SABA1.2 was soluble to at least 20 mg/mL protein concentration at 4° C. and ambient temperature with no precipitation or increase in aggregation.

Example 8

Biophysical Characterization of Candidate SABAs

Size Exclusion Chromatography

Standard size exclusion chromatography (SEC) was performed on the candidate SABAs resulting from the midscale process. SEC of midscaled material was performed using a SUPERDEX® 200 10/30 or on a SUPERDEX® 75 10/30 column (GE Healthcare) on an Agilent 1100 or 1200 HPLC system with UV detection at $A_{214}$ nm and $A_{280}$ nm and with fluorescence detection (excitation=280 nm, emission=350 nm). A buffer of 100 mM sodium sulfate, 100 mM sodium phosphate, 150 mM sodium chloride, pH 6.8 at appropriate flow rate of the SEC column employed. Gel filtration standards (Bio-Rad Laboratories, Hercules, Calif.) were used for molecular weight calibration.

The results of the SEC on the midscaled purified SABAs showed predominantly monomeric Adnectin and elution in the approximate range of 10 kDa vs. globular Gel Filtration standards (BioRad) as showed.

Thermostability

Differential Scanning calorimetry (DSC) analyses of the midscaled SABAs were performed to determine their respective $T_m$'s. A 1 mg/ml solution was scanned in a N-DSC II calorimeter (calorimetry Sciences Corp) by ramping the temperature from 5° C. to 95° C. at a rate of 1 degree per minute under 3 atm pressure. The data was analyzed vs. a control run of the appropriate buffer using a best fit using Orgin Software (OrginLab Corp). The results of the SEC and DSC analyses are summarized in Table 11.

TABLE 11

Summary of SEC and DSC Analyses on Candidate SABAs

| Clone | SEC | | DSC (Tm) |
|---|---|---|---|
| | Monomer (%) | Dimer (%) | |
| SABA1.1 | 92.3 | 7.7 | 63.9° C. |
| SABA5.1 | 88 | 12 | 70.1° C. |
| SABA2.1 | 91 | 9 | 58.5° C./78.2° C. |
| SABA3.1 | 99 | BLD | 65.2° C. |

Example 9

Characterization of Candidate SABA1 Binding to Serum Albumin

The kinetics of selected SABA clones purified from HTPP and/or midscaled material were determined by capturing the respective serum albumin (HSA/RhSA/MuSA) on the surface of a Biasensor CM5 chip and flowing a concentration series of SABAs over both the reference flow cell and the captured albumins. In addition, binding to albumin was carried out under various pH conditions ranging from pH 5.5 to pH 7.4. HSA-binding Adnectins SABA2.1, SABA3.1, SABA4.1 (SABA5.1) & SABA1.1 cross reacted with RhSA but did not cross react with MuSA. SABA2 and SABA4 binding is pH sensitive whereas clone SABA3 demonstrated pH resistance binding to HSA down to pH 6.0. SABA1.1 fits biochemical criteria for pH resistance and affinity/kinetics down to pH 5.5.

Domain mapping was determined by Biacore. Selected SABA clones purified from HTPP and/or midscaled material were determined by capturing HSA or a construct consisting of just HSA-domain I & II or HSA-domain III on the surface of a Biasensor CMS chip and flowing a concentration series of the SABAs over both the reference flow cell and the captured albumins. Clones SABA2 & SABA1 bound to HSA and the HSA-domain I-II construct but not the HSA-domain III construct. Clones SABA3 & SABA4 bound to HSA but not to either the HSA-domain I-II or HSA-domain III constructs. The results are summarized in Table 12.

TABLE 12

Binding Affinity and Kinetics of Candidate SABAs (SABA1.1, 2.1, 3.1 and 4.1)

| Adnectin | Target | $K_D$ (nM) | $K_{off}(s^{-1})$ | Resistant to pH 7.4→5.5 | Epitope on HSA |
|---|---|---|---|---|---|
| SABA2 | HSA | 33.8 +/− 20.5 (n = 6) | 1.71E−04 | — | Domain I-II |
|  | RhSA | 63.6 | 4.42E−04 |  |  |
| SABA3 | HSA | 863 | 6.82E−02 | +++ (down to pH 6.0) | Neither domain I-II nor III (interfacial?) |
|  | RhSA | 431 | 3.37E−02 |  |  |
| SABA4 | HSA | 412 +/− 8 (n = 4) | 7.82E−04 | — | Neither domain I-II nor III (interfacial?) |
|  | RhSA | >1000 | 3.83E−03 |  |  |
| SABA1 | HSA | 47.2 +/− 18.2 (n = 9) | 4.57E−04 | +++ | Domain I-II |
|  | RhSA | 778 +/− 313 (n = 4) | 5.45E−03 |  |  |

Example 10

Examination of the In Vivo $t_{1/2}$ of Candidate SABAs

Figure 11A:
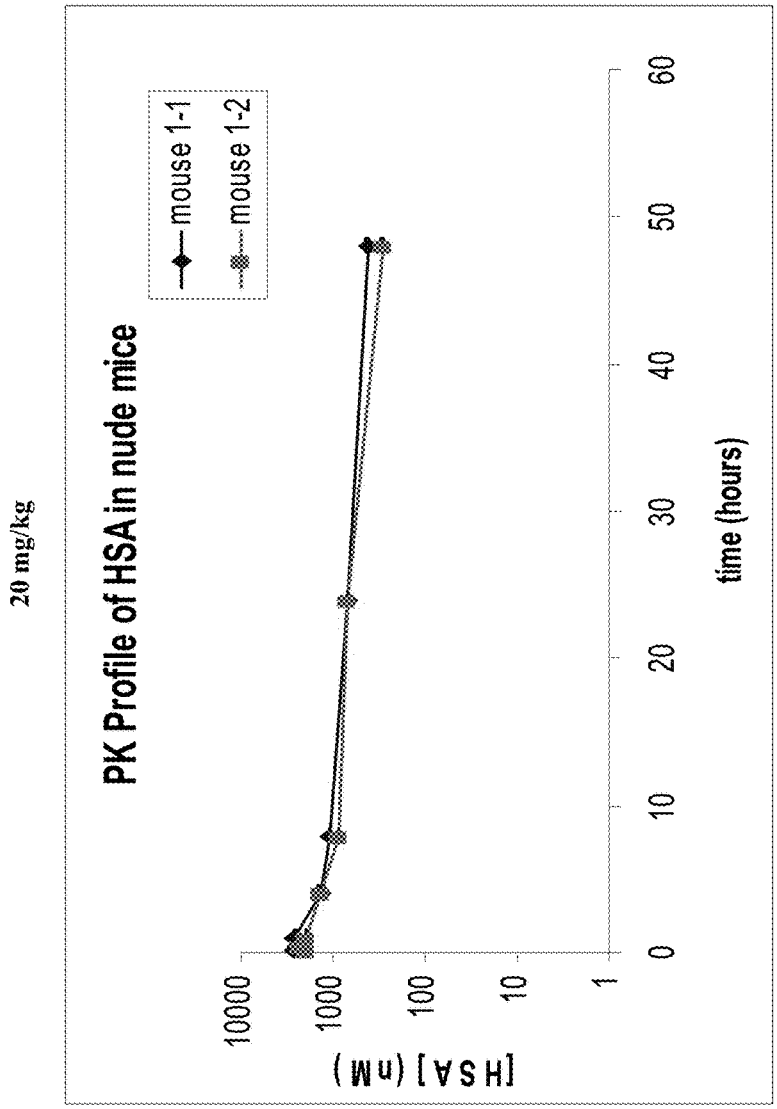
FIG. 11A and FIG. 11B shows in vivo HSA half-life in mice. HSA was injected into mice at 20 mg/kg (FIG. 11A) or 50 mg/kg (FIG. 11B).
Figure 11B:
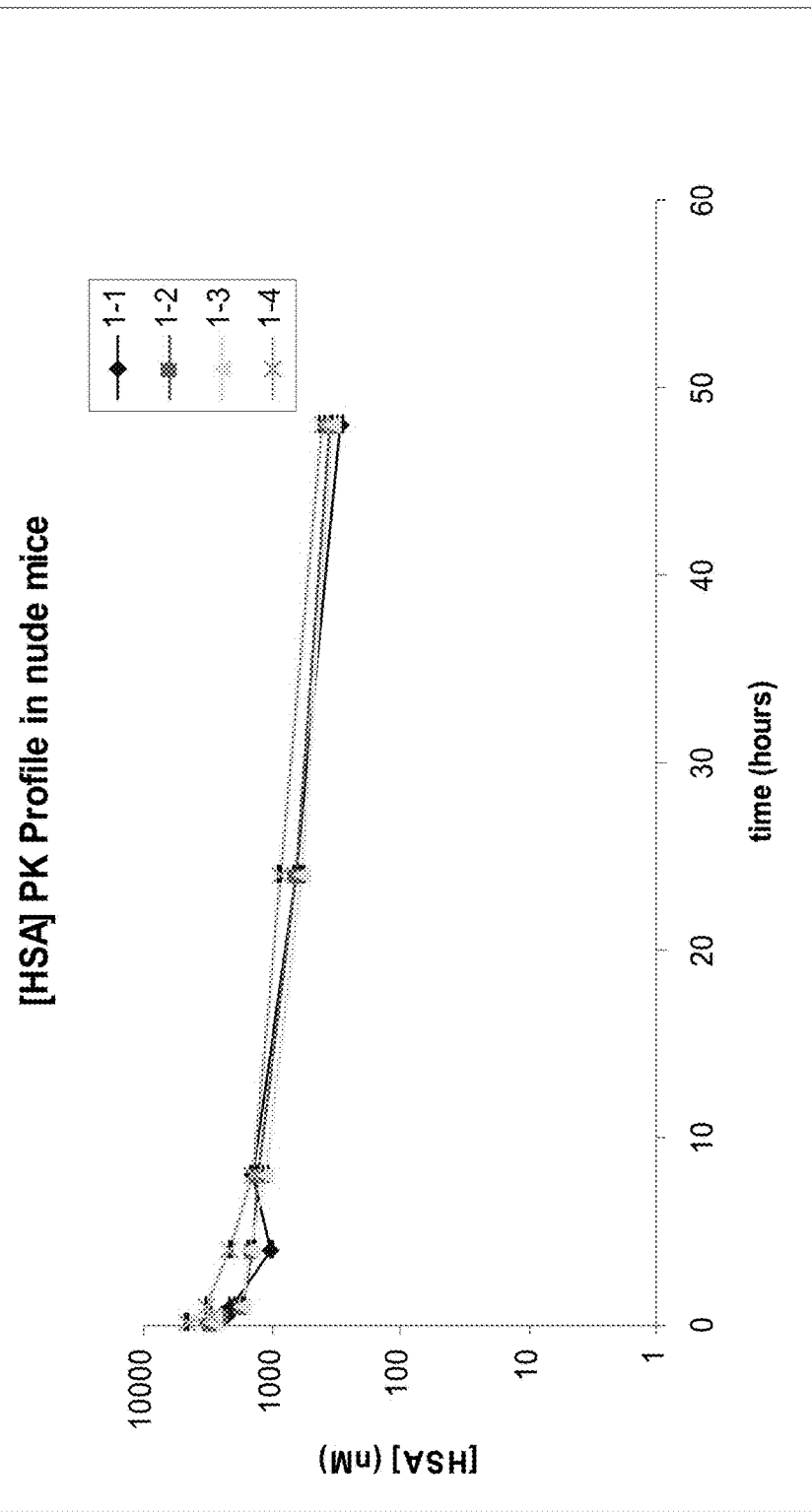

The half-life of HSA in mice was determined to allow for evaluation of HSA-binding Adnectins in mice as the HSA-binding Adnectins do not cross react with MuSA. HSA was injected into the tail vein of approximately 6 week old Ncr nude female mice at a 20 mg/kg (FIG. 11A) and 50 mg/kg dose (FIG. 11B), and the concentration of HSA in blood samples taken at intervals post-injection was determined by ELISA. The $t_{1/2}$ of HSA injected into mice at 20 mg/kg and 50 mg/kg were determined to be ~24 hrs and ~20 hrs, respectively.

Half-Life Determination of SABA1-4 in Mice

One liter E. coli growth of HSA binding clones SABA1.1, SABA2.1, SABA3.1, and SABA4.1 were prepared, purified and endotoxin removed. Each SABA variant was injected into the tail vein of mice, and the concentration in blood samples taken at intervals post-injection was determined by ELISA.

Figure 12B:
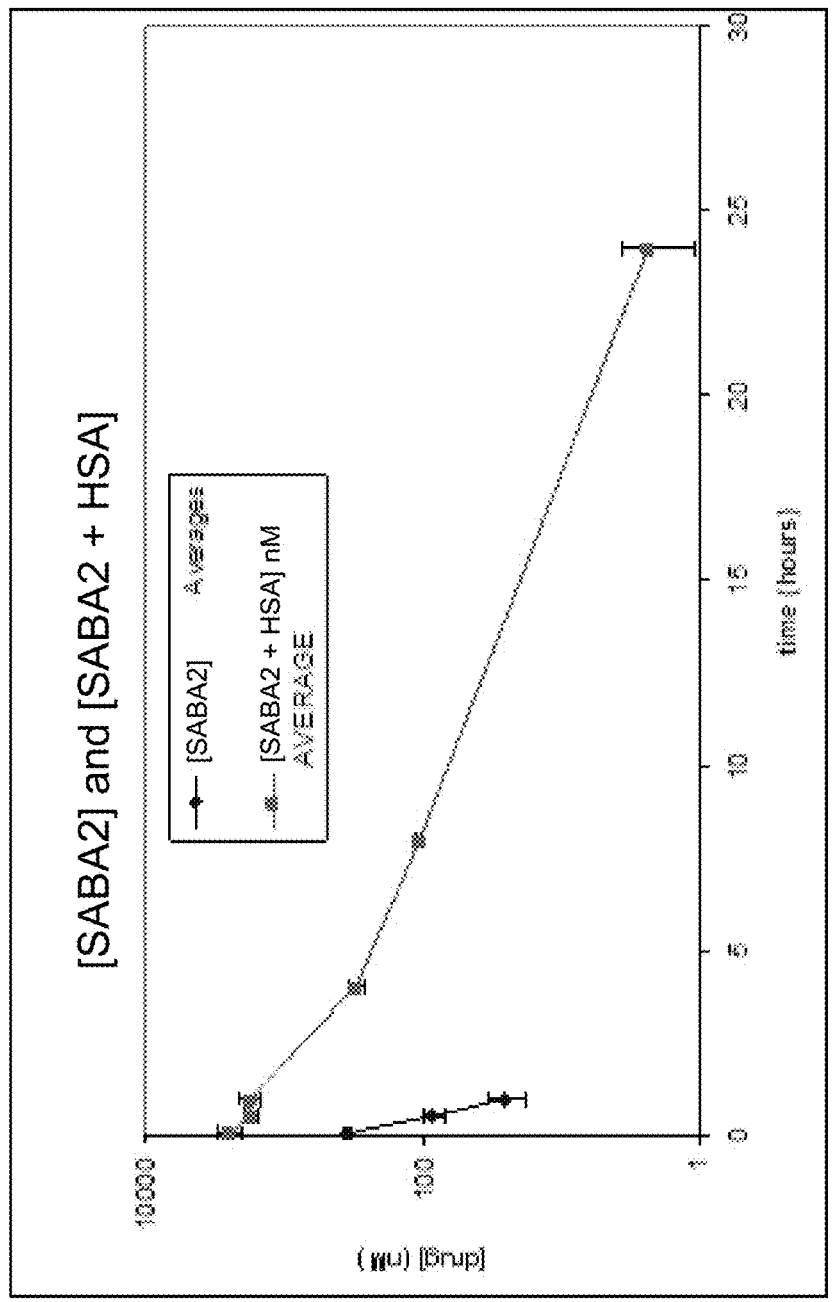
Figure 12C:
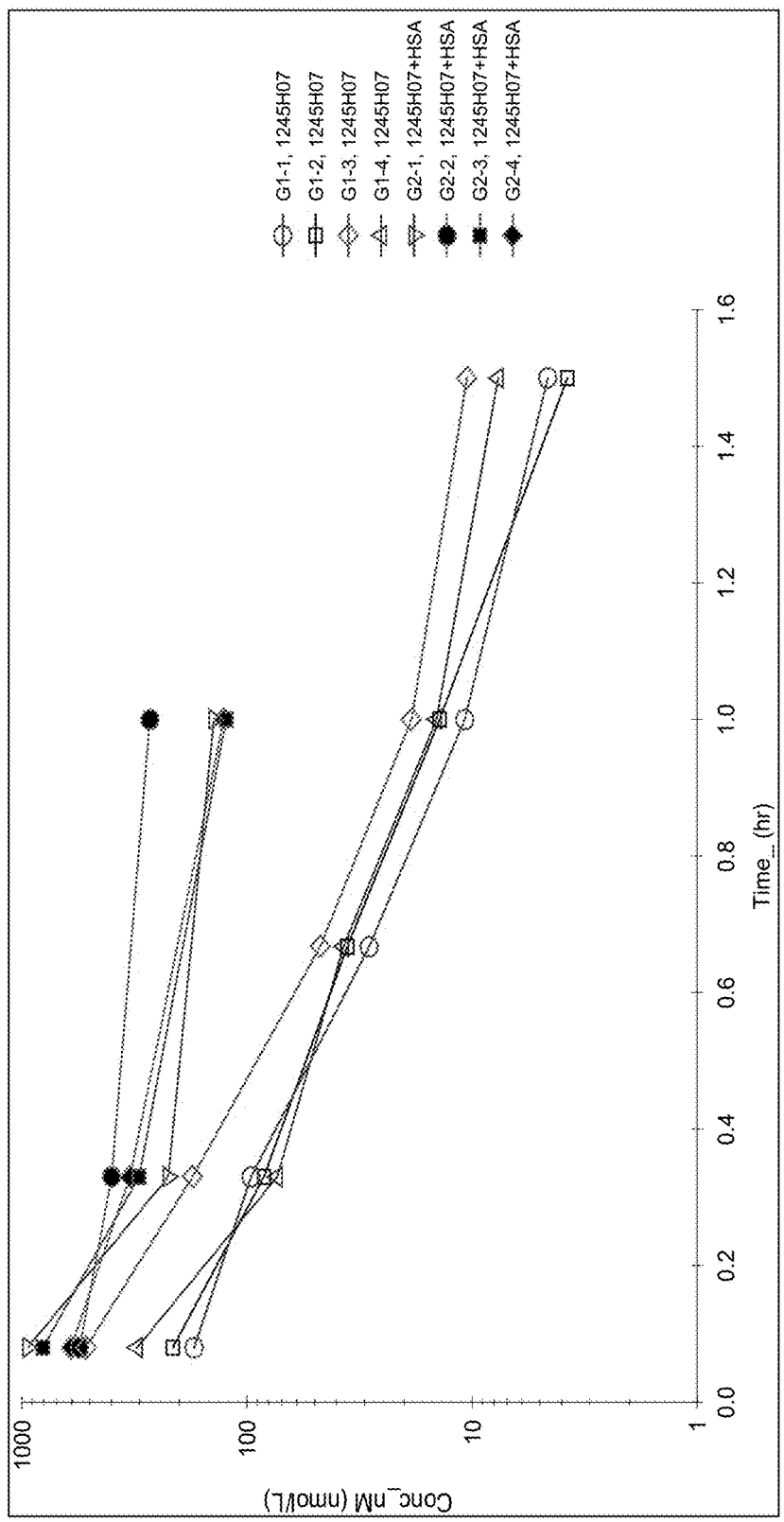
Figure 13A:
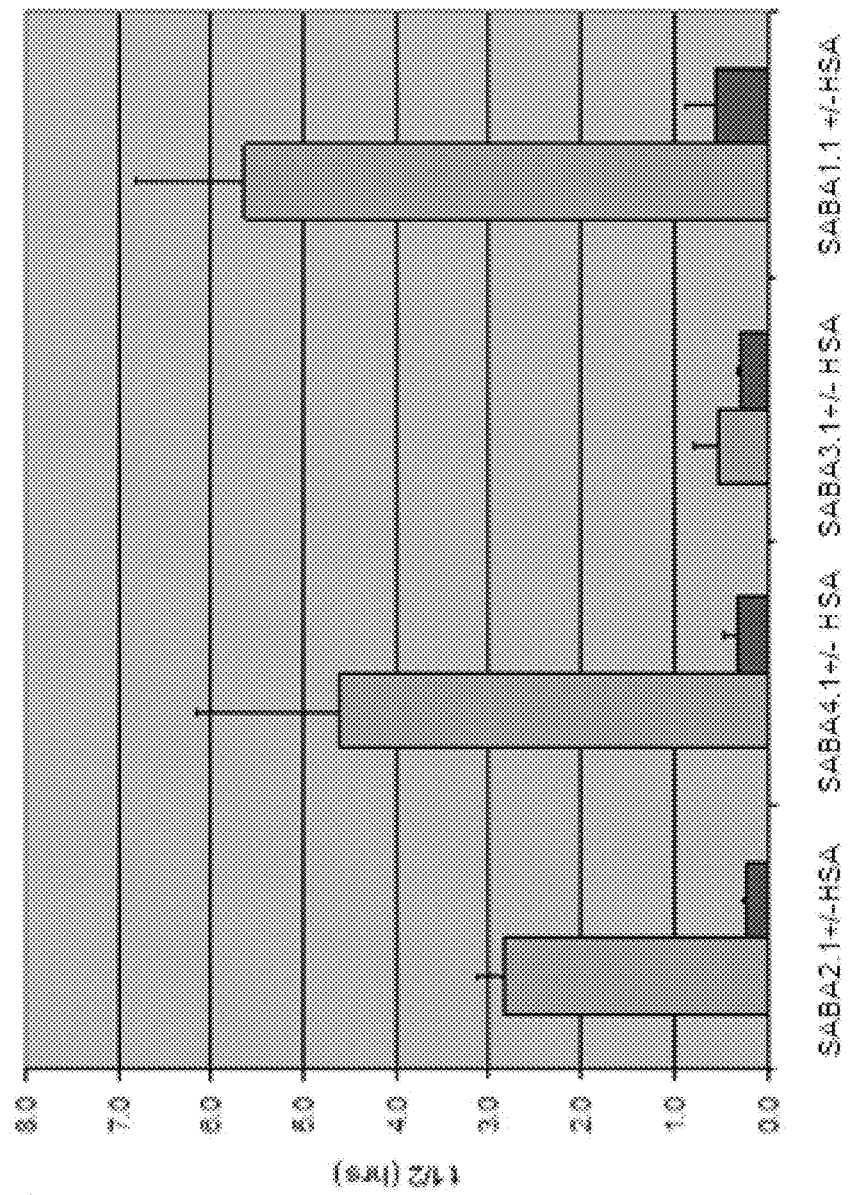
FIG. 13A shows a graph summary of half-life enhancement in mice of SABA1-4 when co-injected with HSA.

The pharmacokinetic profiles of each SABA were compared in the presence or absence of HSA in approximately 6 week old Ncr nude female mice. The mice that were co-injected with HSA had the HSA premixed with each SABA (HSA in a 3-4 molar excess) because the binding clone was selective for HSA and RhSA and did not bind the mouse serum albumin. The half-life of SABA1.1 in mice plasma was 0.56 hours whereas the half-life of SABA1.1 co-injected with HSA was 5.6 hours, a ~10-fold increase in half life (FIG. 12A). The half-life of SABA2.1 in mice plasma was 0.24 hours whereas the half-life of SABA2.1 co-injected with HSA was 2.8 hours, a ~12-fold increase in half life (FIG. 12B). The half-life of SABA3.1 in mice plasma was 0.28 hours whereas the half-life of SABA3.1 co-injected with HSA was 0.53 hours, a ~2-fold increase in half life (FIG. 12C). The half-life of SABA4.1 in mice plasma was 0.66 hours whereas the half-life of SABA4 co-injected with HSA was 4.6 hours, a ~7-fold increase in half life (FIG. 12D). A summary of the present example is shown in FIG. 13A.

Half-Life Determination of SABA1.1 and SABA5.1 in Cynomolgus Monkeys

Figure 14A:
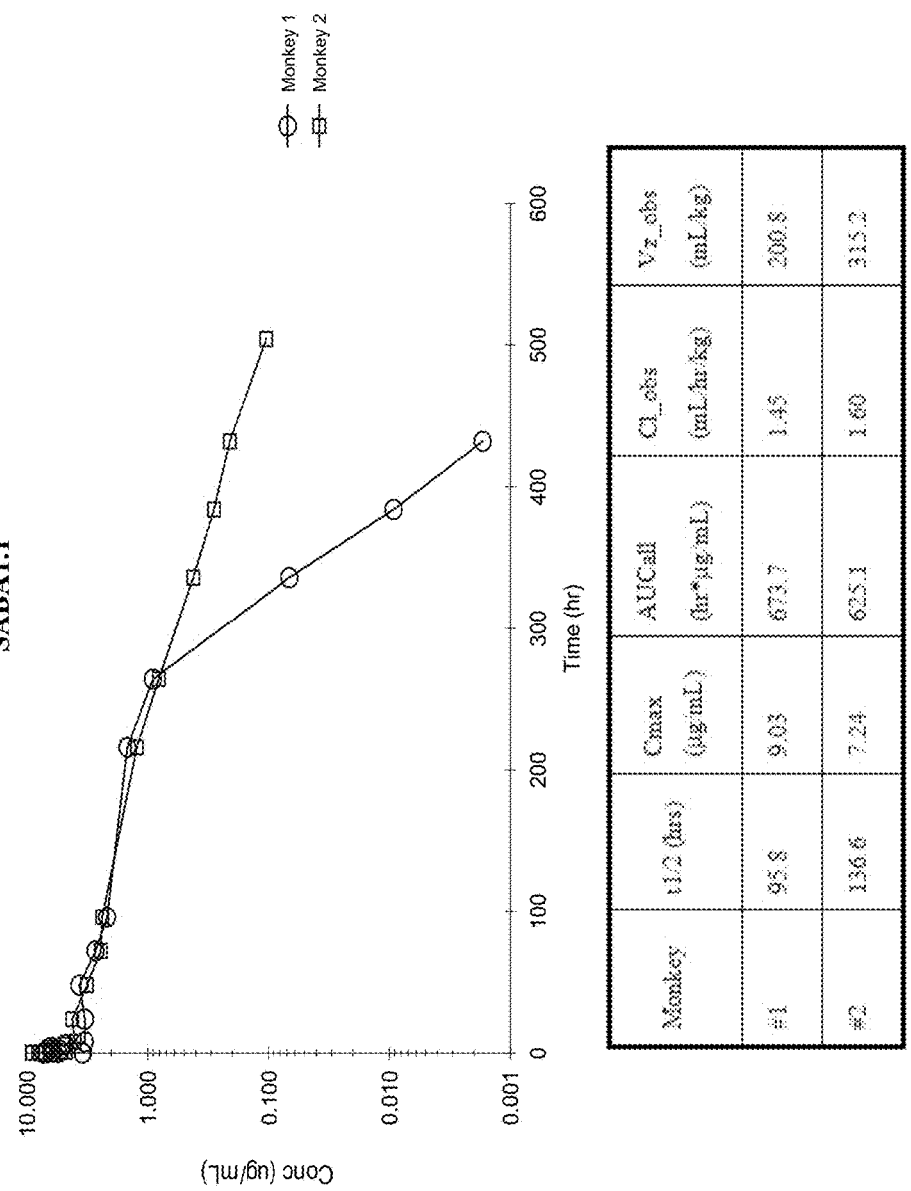
FIGS. 14A-B show the half-life determination for SABA1.1 and SABA5.1 in cynomolgus monkey.
Figure 14B:
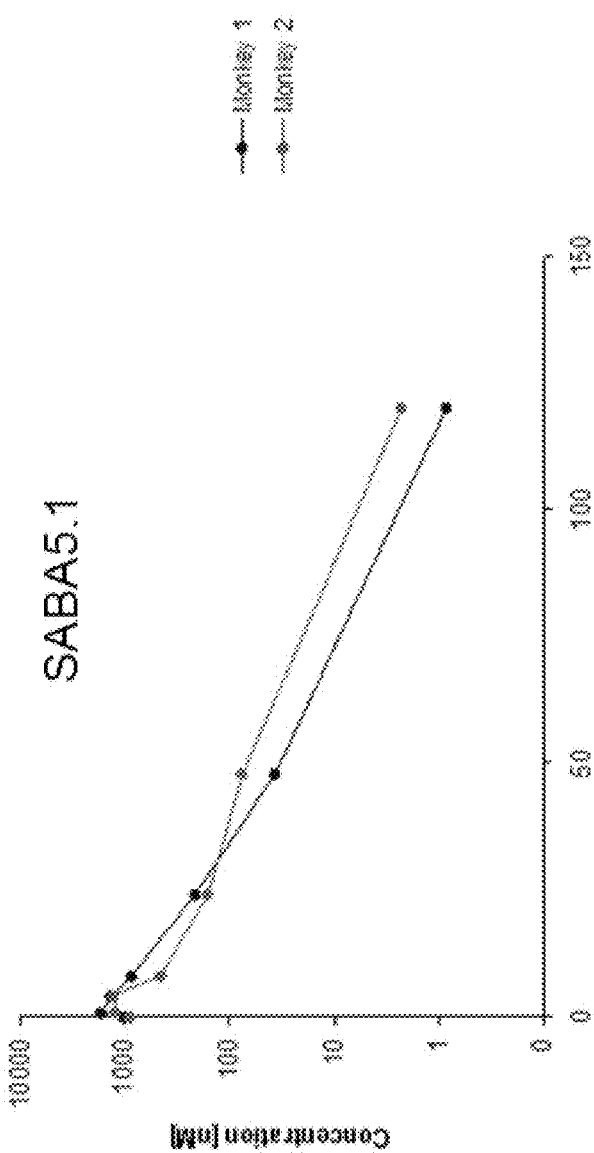

A three week single dose proof of concept study of SABA1.1 and SABA5.1 was conducted in cynomolgus monkeys to assess pharmacokinetics at a 1 mg per kg (mpk) dose IV in 2 cynomolgus monkeys. The pharmacokinetics were evaluated using a quantitative ELISA-based assay that was developed to detect the Adnectin in plasma samples. SABA1.1 has a half-life in the range of 96-137 hours. SABA5.1 has a half-life of approximately 12 hours and was only measureable in the ELISA up to 120 hours. FIGS. 14A and B summarizes data for these clones and compares data from cynomolgus monkey.

Example 11

Characterization of SABA1 Binding To Serum Albumin

SABA1.1 and 1.2 Binds to HSA and RhSA

Figure 15:
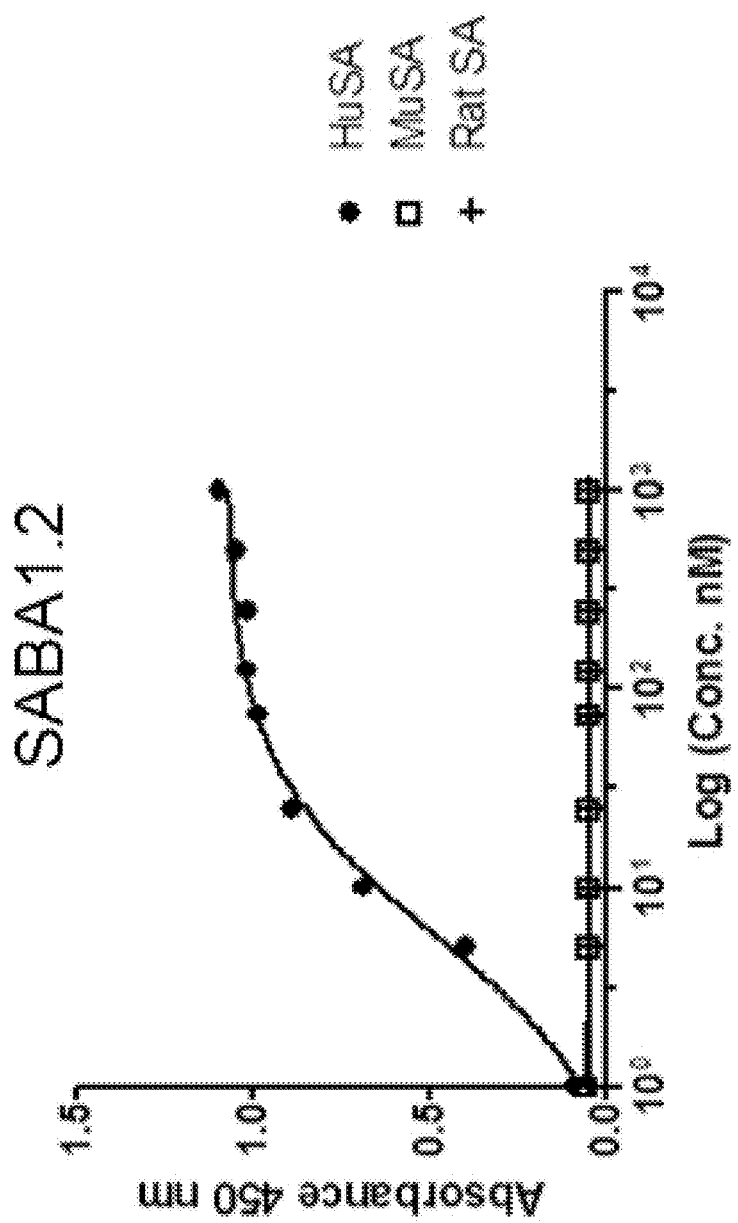
FIG. 15 shows SABA1.2 binding to albumins from human, mouse and rat by direct binding ELISA assay.

SABA1.2, a "core 1" $^{10}$Fn3 comprising an $(ED)_5$ extension (SEQ ID NO: 190) bound to human serum albumin (HSA) at neutral pH and 25° C. with an average association rate constant (ka) of 8.21 E+03 $M^{-1}s^{-1}$, and an average dissociation rate constant (kd) of 4.43 E-04 $s^{-1}$, for a calculated average $K_d$ of 55.3 nM (Table 13). For rhesus serum albumin (RhSA), the measured average association rate constant was 6.6 E+03 $M^{-1}s^{-1}$, and the dissociation rate constant was 3.78 E-03 $s^{-1}$, giving a calculated average $K_d$ of 580 nM. No measurable interaction between SABA1.2 and mouse or rat serum albumin could be observed up to 1 µM (Table 13 and FIG. 15). At 37° C., the ka and kd increased between 2 to 5-fold, leading to a ~2-fold increase in affinity for HSA and ½ the affinity for RhSA (Table 13).

TABLE 13

Kinetic Parameters for SABA1.2 Binding to Albumins, in HBS-P Buffer

| Albumin | Temp (° C.) | ka (1/Ms) | kd (1/s) | KD (nM) |
|---|---|---|---|---|
| Human | 25 | 8.21 ± 1.19 E+03 | 4.43 ± 0.65 E−04 | 55.3 ± 13.7 |
| Rhesus | | 6.60 ± 1.18 E+03 | 3.78 ± 0.45 E−03 | 580 ± 62.6 |
| Mouse | | no observable binding | | |
| Human | 37 | 3.38E+04 | 8.15E−04 | 24.1 |
| Rhesus | | 1.89E+04 | 1.85E−02 | 977.4 |
| Mouse | | no observable binding | | |

Figure 16:
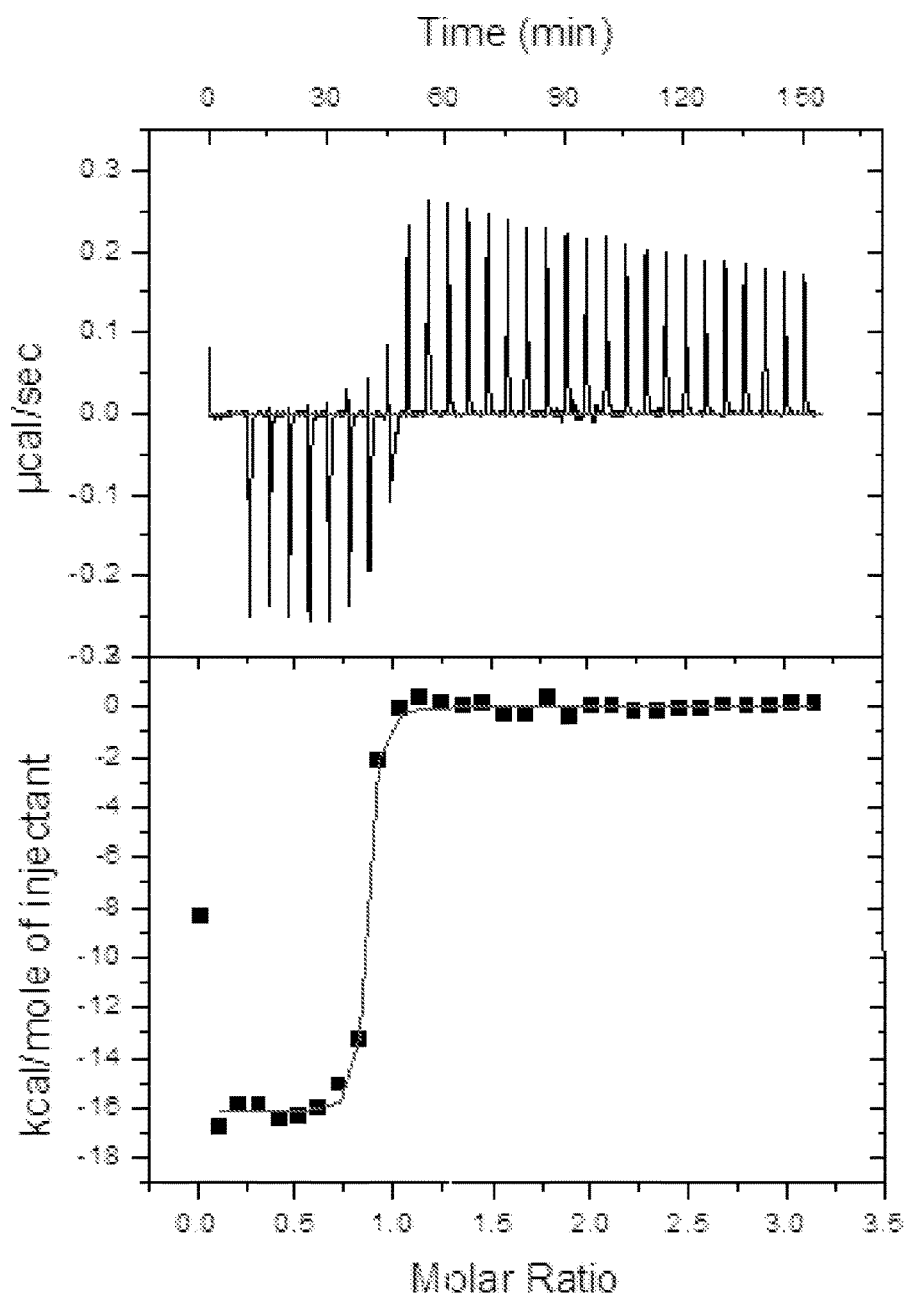
FIG. 16 shows the determination of SABA1.1 and HSA stoichiometry.

Additionally, a calorimetric titration was performed to determine the stoichiometry between SABA1 and HSA. For this study, SABA1.1, a "core 1" $^{10}$Fn3 comprising a His6 extension (SEQ ID NO: 189), was used. HSA (10 μl per injection of 115 μM protein solution) was injected into the calorimetric cell containing SABA1.1 at a concentration of 8.1 μM. The experiment was performed at 37° C. in PBS buffer pH 7.4. FIG. 16 shows that SABA1.1 binds to HSA with 1:1 stoichiometry.

SABA1.2 Binds Potently to HSA at Low pH

The long half-life of albumins (e.g., $t_{1/2}$ of HSA is 19 days) is due in large part to the fact that they are recycled from an endocytic pathway by binding to the neonatal Fc recptor, FcRn, under the low pH conditions that exist inside the endosome. As shown in Table 14 SABA1.2 potently bound HSA at the endosomal pH of 5.5, suggesting that the $t_{1/2}$ of SABA1, once bound to HSA, would also benefit from the FcRn recycling mechanism.

TABLE 14

Comparison of Albumin Binding Kinetics at pH 7.4 and 5.5, in MES Buffer

| albumin | pH | ka (1/Ms) | kd (1/s) | KD (nM) |
|---|---|---|---|---|
| Human | 7.4 | 9.26E+03 | 3.88E−04 | 41.9 |
|  | 5.5 | 9.44E+03 | 2.70E−04 | 28.6 |
| Rhesus | 7.4 | 6.16E+03 | 2.95E−03 | 479 |
|  | 5.5 | 7.57E+03 | 2.72E−03 | 359 |

SABA1.2 Binds to Domains I and II of HSA, but Not Domain III

The binding site SABA1.2 on albumin was mapped to the N-terminal domains I or II using recombinant HSA fragments and has no detectable binding to domain III (FIG. 17). Because domain III is the domain of HSA that primarily interacts with FcRn, it is less likely that SABA1.2 would compete for HSA binding to FcRn, again increasing the possibility of fully leveraging the recycling mechanism for enhanced half-life.

Example 12

In Vivo Pharmacology of SABA1.2

A four week single dose pre-toxicology study of SABA1.2 was conducted in cynomolgus monkeys to assess pharmacokinetics and immunogenicity at two different dose levels. The pharmacokinetics and immunogenicity were also evaluated in a three-week, single-dose pre-toxicology study that included both intravenous and subcutaneous administration arms. Additionally, the pharmacokinetics of SABA1.2 was evaluated in two separate, single dose pre-toxicology studies in cynomolgus monkeys using a quantitative ELISA-based assay that was developed to detect SABA1.2 in plasma samples.

Figure 18:
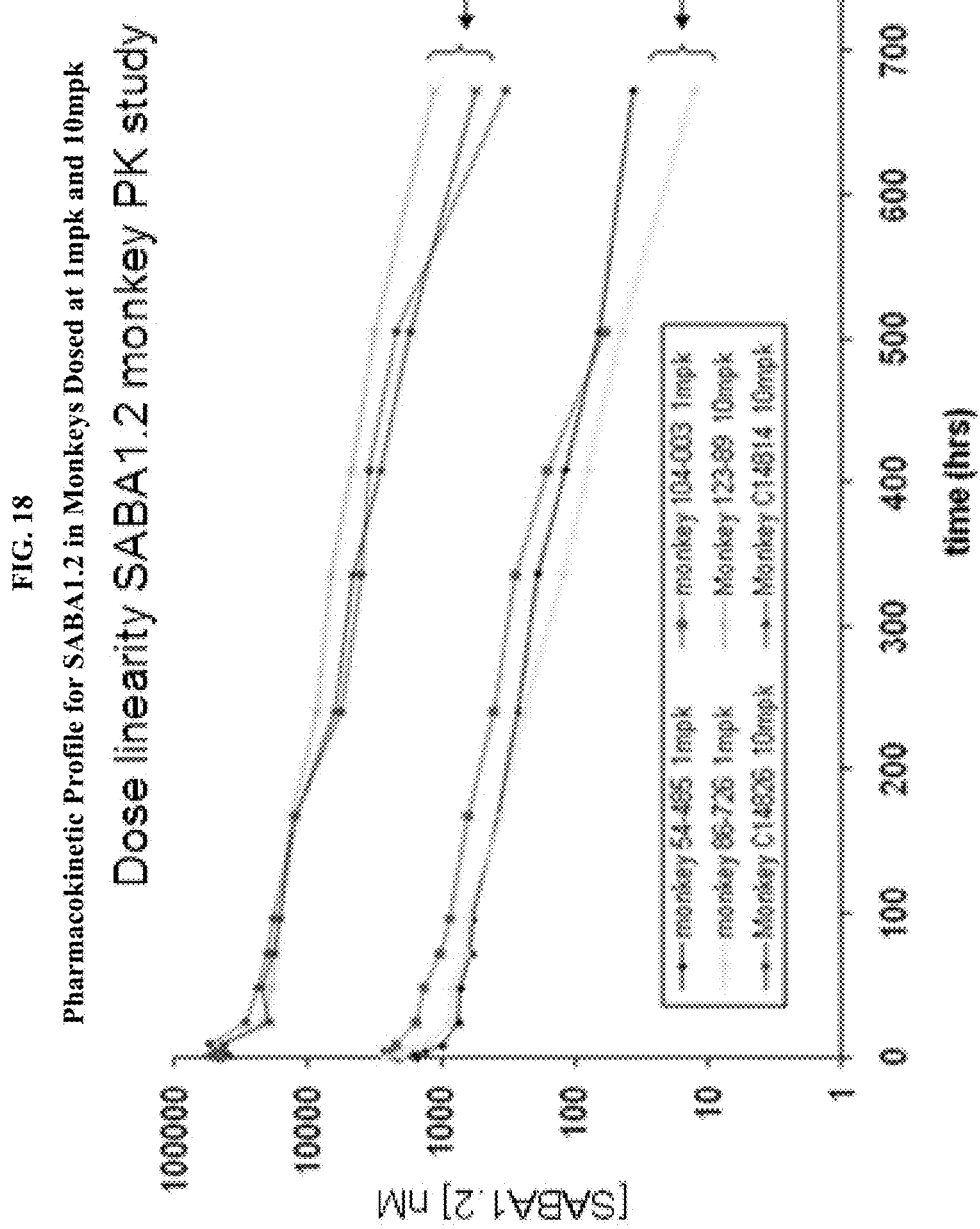
FIG. 18 shows the pharmacokinetic profile for SABA1.2 in monkeys dosed at 1 mpk and 10 mpk.

SABA1.2 was administered to monkeys at 1 mpk and 10 mpk IV. As shown in FIG. 18 and the parameters described below, the Cmx and AUC increased approximately linear with dose. Non-compartmental analyses using WINNONLIN® software were performed to evaluate pharmacokinetic parameters. The clearance (CL) for SABA1.2 at 10 mpk was 0.15 ml/hr/kg, the beta phase half-life ($t_{1/2}$) was 143 hours, the volume of distribution (Vz) was 30 mL/kg, and total drug exposure (AUCall) was 5,609,457 hr*nmol/L (Table 15). The clearance (CL) for SABA1.2 at 1 mpk was 0.4 ml/hr/kg, the half-life ($t_{1/2}$) was 124 hours, the volume of distribution (Vz) was 72 mL/kg, and total drug exposure (AUCall) was 214,636 hr*nmol/L (Table 15).

Figure 19:
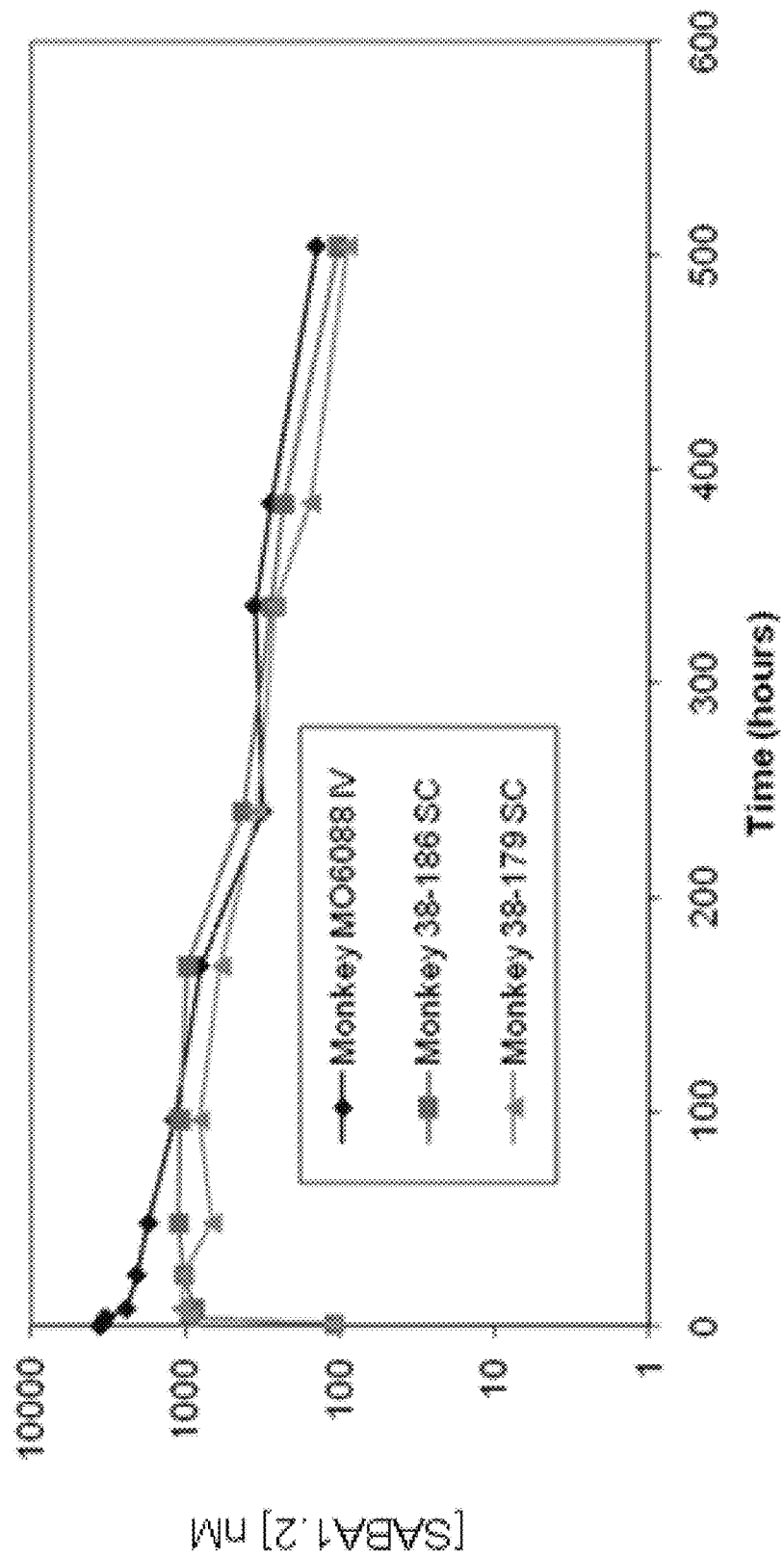
FIG. 19 shows the pharmacokinetic profile for SABA1.2 in monkeys dosed intravenously or subcutaneously at 1 mpk.

After SC or IV administration of SABA1.2, the beta-phase pharmacokinetic profiles were similar (FIG. 19). Non-compartmental analyses using WINNONLIN® software were performed to evaluate pharmacokinetic parameters. The clearance (CL) for SABA1.2 at 1 mpk IV was 0.22 ml/hr/kg, the beta phase half-life ($t_{1/2}$) was 125 hours, the volume of distribution (Vz) was 40 mL/kg, and total drug exposure (AUCall) was 357,993 hr*nmol/L (Table 15). The clearance (CL) for SABA1.2 at 1 mpk SC was 0.32 ml/hr/kg, the beta phase half-life ($t_{1/2}$) was 134 hours, the volume of distribution (Vz) was 62 mL/kg, and total drug exposure (AUCall) was 251,339 hr*nmol/L (Table 15). The SC relative bioavailability (F) compared to IV was 0.7.

TABLE 15

Pharmacokinetic Parameters for SABA1.2 in Monkeys

| | Study # | | | |
|---|---|---|---|---|
| | 1 | | 2 | |
| Dose (mg/kg) | 1 | 10 | 1 | 1 |
| Route of administration | i.v. | i.v. | i.v. | s.c. |
| N | 3 | 3 | 1 | 2 |
| CL (mL/hr/kg) | 0.4 | 0.15 | 0.22 | 0.32 |
| Vz (mL/kg) | 72 | 30 | 40 | 62 |
| AUCall (hr * nmol/L) | 214,636 | 5,609,457 | 357,993 | 251,339 |
| beta $T_{1/2}$ (h) | 124 | 143 | 125 | 134 |
| Bioavailability (F) | n/a | n/a | n/a | 0.7 |

We claim:

1. A polypeptide comprising a fibronectin type III tenth domain ($^{10}$Fn3) shown in SEQ ID NO:1 wherein the $^{10}$Fn3 comprises a BC loop is selected from SEQ ID NO:3 or SEQ ID NO:6, a DE loop selected from SEQ ID NO: 7-48, and a FG loop selected from SEQ ID NO: 49-59 and wherein the polypeptide binds the p19 subunit of IL-23.

2. A polypeptide comprising a fibronectin type III tenth domain ($_{10}$Fn3) shown in SEQ ID NO:1 wherein the $^{10}$Fn3 comprises a BC loop selected from SEQ ID NO:2-6, a DE loop selected from SEQ ID NO: 26, SEQ ID NO:33, SEQ ID NO: 34 or SEQ ID NO: 38, and a FG loop selected from SEQ ID NO: 49-59 and wherein the polypeptide binds the p19 subunit of IL-23.

3. A polypeptide comprising a fibronectin type III tenth domain ($^{10}$Fn3) shown in SEQ ID NO:1 wherein the $^{10}$Fn3 comprises a BC loop selected from SEQ ID NO:2-6, a DE loop selected from SEQ ID NO: 7-48, and a FG loop selected from SEQ ID NO: 52, SEQ ID NO: 53 or SEQ ID NO: 55 and wherein the polypeptide binds the p19 subunit of IL-23.

4. A polypeptide comprising a fibronectin type III tenth domain ($^{10}$Fn3) shown in SEQ ID NO:1 wherein the $^{10}$Fn3 comprises BC loop as shown in SEQ ID NO:3, DE loop as shown in SEQ ID NO: 26, and FG loop as shown in SEQ ID NO: 53, BC loop as shown in SEQ ID NO:3, DE loop as shown in SEQ ID NO: 33, and FG loop as shown in SEQ ID NO: 52, BC loop as shown in SEQ ID NO:6, DE loop as shown in SEQ ID NO: 34, and FG loop as shown in SEQ ID NO: 55, or BC loop as shown in SEQ ID NO:3, DE loop as shown in SEQ ID NO: 38, and FG loop as shown in SEQ ID NO: 52.

5. A fibronectin type III tenth domain ($^{10}$Fn3) polypeptide as shown in SEQ ID NO: 79.

6. A fibronectin type III tenth domain ($^{10}$Fn3) polypeptide as shown in SEQ ID NO: 86.

7. A fibronectin type III tenth domain ($^{10}$Fn3) polypeptide as shown in SEQ ID NO: 87.

8. A fibronectin type III tenth domain ($^{10}$Fn3) polypeptide as shown in SEQ ID NO: 91.

9. The polypeptide of any one of claims 1 to 8 further comprising one or more pharmacokinetic (PK) moieties selected from the group consisting of polyethylene glycol, sialic acid, Fc, Fc fragment, transferrin, serum albumin, a serum albumin binding protein and a serum immunoglobulin binding protein.

10. The polypeptide of claim 9 wherein the PK moiety is polyethylene glycol.

11. The polypeptide of claim 9 further comprising a cysteine linker.

12. The polypeptide of claim 11 wherein the cysteine linker is selected from the group consisting of the amino acids GSGC shown in SEQ ID NO: 101 and EIDKPCQ shown in SEQ ID NO: 102.

13. A pharmaceutically acceptable composition comprising the polypeptide of any one of claims 1-5, wherein the composition is essentially endotoxin free.

* * * * *

UNITED STATES PATENT AND TRADEMARK OFFICE
CERTIFICATE OF CORRECTION

PATENT NO.       : 9,714,281 B2
APPLICATION NO.  : 14/553379
DATED            : July 25, 2017
INVENTOR(S)      : Dasgupta et al.

Page 1 of 1

It is certified that error appears in the above-identified patent and that said Letters Patent is hereby corrected as shown below:

In the Claims

Column 185
Line 20, in Claim 2, delete "$(_{10}Fn3)$" and insert -- $(^{10}Fn3)$ --.

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 258

<210> SEQ ID NO 1
<211> LENGTH: 94
<212> TYPE: PRT
<213> ORGANISM: Homo Sapien

```
<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 7
<212> TYPE: PRT
<213> ORGANISM: Artificial Sequence
<220> FEATURE:
<223> OTHER INFORMATION: BC LOOP

<400> SEQUENCE: 2

Gly His Tyr Pro Met His Val
1               5

<210> SEQ ID NO 3
<211> LENGTH: 7
<212> TYPE: PRT
<213> ORGANISM: Artificial Sequence
<220> FEATURE:
<223> OTHER INFORMATION: BC LOOP

<400> SEQUENCE: 3

Gly His Tyr Pro Leu His Val
1               5

<210> SEQ ID NO 4
<211> LENGTH: 7
<212> TYPE: PRT
<213> ORGANISM: Artificial Sequence
<220> FEATURE:
<223> OTHER INFORMATION: BC LOOP

<400> SEQUENCE: 4

Gly His Tyr Pro Met His Ile
1               5

<210> SEQ ID NO 5
<211> LENGTH: 7
<212> TYPE: PRT
<213> ORGANISM: Artificial Sequence
<220> FEATURE:
<223> OTHER INFORMATION: BC LOOP

<400> SEQUENCE: 5

Gly His Tyr Pro Leu His Ile
1               5

<210> SEQ ID NO 6
<211> LENGTH: 7
<212> TYPE: PRT
<213> ORGANISM: Artificial Sequence
<220> FEATURE:
<223> OTHER INFORMATION: BC LOOP
```

```
<400> SEQUENCE: 6

Gly His Tyr Pro Leu His Leu
1               5

<210> SEQ ID NO 7
<211> LENGTH: 4
<212> TYPE: PRT
<213> ORGANISM: Artificial Sequence
<220> FEATURE:
<223> OTHER INFORMATION: DE LOOP

<400> SEQUENCE: 7

His Arg Thr His
1

<210> SEQ ID NO 8
<211> LENGTH: 4
<212> TYPE: PRT
<213> ORGANISM: Artificial Sequence
<220> FEATURE:
<223> OTHER INFORMATION: DE LOOP

<400> SEQUENCE: 8

Tyr Tyr His Tyr
1

<210> SEQ ID NO 9
<211> LENGTH: 4
<212> TYPE: PRT
<213> ORGANISM: Artificial Sequence
<220> FEATURE:
<223> OTHER INFORMATION: DE LOOP

<400> SEQUENCE: 9

Ser Lys Gln His
1

<210> SEQ ID NO 10
<211> LENGTH: 4
<212> TYPE: PRT
<213> ORGANISM: Artificial Sequence
<220> FEATURE:
<223> OTHER INFORMATION: DE LOOP

<400> SEQUENCE: 10

Ser Asn Val His
1

<210> SEQ ID NO 11
<211> LENGTH: 4
<212> TYPE: PRT
<213> ORGANISM: Artificial Sequence
<220> FEATURE:
<223> OTHER INFORMATION: DE LOOP

<400> SEQUENCE: 11

Asn Arg Ala His
1

<210> SEQ ID NO 12
<211> LENGTH: 4
<212> TYPE: PRT
<213> ORGANISM: Artificial Sequence
<220> FEATURE:
<223> OTHER INFORMATION: DE LOOP
```

```
<400> SEQUENCE: 12

Arg Lys Thr Tyr
1

<210> SEQ ID NO 13
<211> LENGTH: 4
<212> TYPE: PRT
<213> ORGANISM: Artificial Sequence
<220> FEATURE:
<223> OTHER INFORMATION: DE LOOP

<400> SEQUENCE: 13

Arg Ser Arg Tyr
1

<210> SEQ ID NO 14
<211> LENGTH: 4
<212> TYPE: PRT
<213> ORGANISM: Artificial Sequence
<220> FEATURE:
<223> OTHER INFORMATION: DE LOOP

<400> SEQUENCE: 14

Ser Arg Tyr Tyr
1

<210> SEQ ID NO 15
<211> LENGTH: 4
<212> TYPE: PRT
<213> ORGANISM: Artificial Sequence
<220> FEATURE:
<223> OTHER INFORMATION: DE LOOP

<400> SEQUENCE: 15

Pro His Arg Tyr
1

<210> SEQ ID NO 16
<211> LENGTH: 4
<212> TYPE: PRT
<213> ORGANISM: Artificial Sequence
<220> FEATURE:
<223> OTHER INFORMATION: DE LOOP

<400> SEQUENCE: 16

Arg Ser Thr His
1

<210> SEQ ID NO 17
<211> LENGTH: 4
<212> TYPE: PRT
<213> ORGANISM: Artificial Sequence
<220> FEATURE:
<223> OTHER INFORMATION: DE LOOP

<400> SEQUENCE: 17

Ser Arg Ile Tyr
1

<210> SEQ ID NO 18
<211> LENGTH: 4
<212> TYPE: PRT
<213> ORGANISM: Artificial Sequence
<220> FEATURE:
<223> OTHER INFORMATION: DE LOOP

<400> SEQUENCE: 18
```

His Gln Arg Tyr
1

<210> SEQ ID NO 19
<211> LENGTH: 4
<212> TYPE: PRT
<213> ORGANISM: Artificial Sequence
<220> FEATURE:
<223> OTHER INFORMATION: DE LOOP

<400> SEQUENCE: 19

Lys Gln Val Tyr
1

<210> SEQ ID NO 20
<211> LENGTH: 4
<212> TYPE: PRT
<213> ORGANISM: Artificial Sequence
<220> FEATURE:
<223> OTHER INFORMATION: DE LOOP

<400> SEQUENCE: 20

Ala His Arg Tyr
1

<210> SEQ ID NO 21
<211> LENGTH: 4
<212> TYPE: PRT
<213> ORGANISM: Artificial Sequence
<220> FEATURE:
<223> OTHER INFORMATION: DE LOOP

<400> SEQUENCE: 21

Arg Ser Arg His
1

<210> SEQ ID NO 22
<211> LENGTH: 4
<212> TYPE: PRT
<213> ORGANISM: Artificial Sequence
<220> FEATURE:
<223> OTHER INFORMATION: DE LOOP

<400> SEQUENCE: 22

Ala Arg Gln Tyr
1

<210> SEQ ID NO 23
<211> LENGTH: 4
<212> TYPE: PRT
<213> ORGANISM: Artificial Sequence
<220> FEATURE:
<223> OTHER INFORMATION: DE LOOP

<400> SEQUENCE: 23

Arg Thr Gln Tyr
1

<210> SEQ ID NO 24
<211> LENGTH: 4
<212> TYPE: PRT
<213> ORGANISM: Artificial Sequence
<220> FEATURE:
<223> OTHER INFORMATION: DE LOOP

<400> SEQUENCE: 24

Pro Arg Tyr His
1

<210> SEQ ID NO 25
<211> LENGTH: 4
<212> TYPE: PRT
<213> ORGANISM: Artificial Sequence
<220> FEATURE:
<223> OTHER INFORMATION: DE LOOP

<400> SEQUENCE: 25

Met Arg Gln His
1

<210> SEQ ID NO 26
<211> LENGTH: 4
<212> TYPE: PRT
<213> ORGANISM: Artificial Sequence
<220> FEATURE:
<223> OTHER INFORMATION: DE LOOP

<400> SEQUENCE: 26

Ser Arg Lys Tyr
1

<210> SEQ ID NO 27
<211> LENGTH: 4
<212> TYPE: PRT
<213> ORGANISM: Artificial Sequence
<220> FEATURE:
<223> OTHER INFORMATION: DE LOOP

<400> SEQUENCE: 27

Arg Gln Lys Tyr
1

<210> SEQ ID NO 28
<211> LENGTH: 4
<212> TYPE: PRT
<213> ORGANISM: Artificial Sequence
<220> FEATURE:
<223> OTHER INFORMATION: DE LOOP

<400> SEQUENCE: 28

His Ala Lys Tyr
1

<210> SEQ ID NO 29
<211> LENGTH: 4
<212> TYPE: PRT
<213> ORGANISM: Artificial Sequence
<220> FEATURE:
<223> OTHER INFORMATION: DE LOOP

<400> SEQUENCE: 29

Ser Asn Arg Tyr
1

<210> SEQ ID NO 30
<211> LENGTH: 4
<212> TYPE: PRT
<213> ORGANISM: Artificial Sequence
<220> FEATURE:
<223> OTHER INFORMATION: DE LOOP

<400> SEQUENCE: 30

Asn Thr Ser His

```
<210> SEQ ID NO 31
<211> LENGTH: 4
<212> TYPE: PRT
<213> ORGANISM: Artificial Sequence
<220> FEATURE:
<223> OTHER INFORMATION: DE LOOP

<400> SEQUENCE: 31

Ser Gln Val Tyr
1

<210> SEQ ID NO 32
<211> LENGTH: 4
<212> TYPE: PRT
<213> ORGANISM: Artificial Sequence
<220> FEATURE:
<223> OTHER INFORMATION: DE LOOP

<400> SEQUENCE: 32

Asn Arg Val Tyr
1

<210> SEQ ID NO 33
<211> LENGTH: 4
<212> TYPE: PRT
<213> ORGANISM: Artificial Sequence
<220> FEATURE:
<223> OTHER INFORMATION: DE LOOP

<400> SEQUENCE: 33

Pro Arg Ser His
1

<210> SEQ ID NO 34
<211> LENGTH: 4
<212> TYPE: PRT
<213> ORGANISM: Artificial Sequence
<220> FEATURE:
<223> OTHER INFORMATION: DE LOOP

<400> SEQUENCE: 34

Arg Thr Lys Tyr
1

<210> SEQ ID NO 35
<211> LENGTH: 4
<212> TYPE: PRT
<213> ORGANISM: Artificial Sequence
<220> FEATURE:
<223> OTHER INFORMATION: DE LOOP

<400> SEQUENCE: 35

Ser Arg Tyr His
1

<210> SEQ ID NO 36
<211> LENGTH: 4
<212> TYPE: PRT
<213> ORGANISM: Artificial Sequence
<220> FEATURE:
<223> OTHER INFORMATION: DE LOOP

<400> SEQUENCE: 36

Pro Arg Arg Tyr
1
```

```
<210> SEQ ID NO 37
<211> LENGTH: 4
<212> TYPE: PRT
<213> ORGANISM: Artificial Sequence
<220> FEATURE:
<223> OTHER INFORMATION: DE LOOP

<400> SEQUENCE: 37

Arg Gln Lys Tyr
1

<210> SEQ ID NO 38
<211> LENGTH: 4
<212> TYPE: PRT
<213> ORGANISM: Artificial Sequence
<220> FEATURE:
<223> OTHER INFORMATION: DE LOOP

<400> SEQUENCE: 38

Arg Tyr Lys Tyr
1

<210> SEQ ID NO 39
<211> LENGTH: 4
<212> TYPE: PRT
<213> ORGANISM: Artificial Sequence
<220> FEATURE:
<223> OTHER INFORMATION: DE LOOP

<400> SEQUENCE: 39

Val Pro Arg His
1

<210> SEQ ID NO 40
<211> LENGTH: 4
<212> TYPE: PRT
<213> ORGANISM: Artificial Sequence
<220> FEATURE:
<223> OTHER INFORMATION: DE LOOP

<400> SEQUENCE: 40

Thr Pro Lys His
1

<210> SEQ ID NO 41
<211> LENGTH: 4
<212> TYPE: PRT
<213> ORGANISM: Artificial Sequence
<220> FEATURE:
<223> OTHER INFORMATION: DE LOOP

<400> SEQUENCE: 41

Arg Ser Lys Tyr
1

<210> SEQ ID NO 42
<211> LENGTH: 4
<212> TYPE: PRT
<213> ORGANISM: Artificial Sequence
<220> FEATURE:
<223> OTHER INFORMATION: DE LOOP

<400> SEQUENCE: 42

Ser Arg Lys Tyr
1
```

```
<210> SEQ ID NO 43
<211> LENGTH: 4
<212> TYPE: PRT
<213> ORGANISM: Artificial Sequence
<220> FEATURE:
<223> OTHER INFORMATION: DE LOOP

<400> SEQUENCE: 43

Val Pro Arg Tyr
1

<210> SEQ ID NO 44
<211> LENGTH: 4
<212> TYPE: PRT
<213> ORGANISM: Artificial Sequence
<220> FEATURE:
<223> OTHER INFORMATION: DE LOOP

<400> SEQUENCE: 44

Pro Arg Arg Tyr
1

<210> SEQ ID NO 45
<211> LENGTH: 4
<212> TYPE: PRT
<213> ORGANISM: Artificial Sequence
<220> FEATURE:
<223> OTHER INFORMATION: DE LOOP

<400> SEQUENCE: 45

Arg Met Arg His
1

<210> SEQ ID NO 46
<211> LENGTH: 4
<212> TYPE: PRT
<213> ORGANISM: Artificial Sequence
<220> FEATURE:
<223> OTHER INFORMATION: DE LOOP

<400> SEQUENCE: 46

Pro Pro Arg His
1

<210> SEQ ID NO 47
<211> LENGTH: 4
<212> TYPE: PRT
<213> ORGANISM: Artificial Sequence
<220> FEATURE:
<223> OTHER INFORMATION: DE LOOP

<400> SEQUENCE: 47

Arg Gln Ile Tyr
1

<210> SEQ ID NO 48
<211> LENGTH: 4
<212> TYPE: PRT
<213> ORGANISM: Artificial Sequence
<220> FEATURE:
<223> OTHER INFORMATION: DE LOOP

<400> SEQUENCE: 48

Met Arg Gln His
1
```

```
<210> SEQ ID NO 49
<211> LENGTH: 10
<212> TYPE: PRT
<213> ORGANISM: Artificial Sequence
<220> FEATURE:
<223> OTHER INFORMATION: FG LOOP

<400> SEQUENCE: 49

Tyr Tyr Asn Glu Ala Asp Tyr Ser Gln Ile
1               5                   10

<210> SEQ ID NO 50
<211> LENGTH: 10
<212> TYPE: PRT
<213> ORGANISM: Artificial Sequence
<220> FEATURE:
<223> OTHER INFORMATION: FG LOOP

<400> SEQUENCE: 50

Tyr Tyr Gln Glu Tyr Glu Tyr Arg Tyr Ile
1               5                   10

<210> SEQ ID NO 51
<211> LENGTH: 10
<212> TYPE: PRT
<213> ORGANISM: Artificial Sequence
<220> FEATURE:
<223> OTHER INFORMATION: FG LOOP

<400> SEQUENCE: 51

Tyr Tyr Met Glu Glu Lys Tyr Ala Val Ile
1               5                   10

<210> SEQ ID NO 52
<211> LENGTH: 10
<212> TYPE: PRT
<213> ORGANISM: Artificial Sequence
<220> FEATURE:
<223> OTHER INFORMATION: FG LOOP

<400> SEQUENCE: 52

Tyr Tyr Ala Gln Glu Asn Tyr Lys Glu Ile
1               5                   10

<210> SEQ ID NO 53
<211> LENGTH: 10
<212> TYPE: PRT
<213> ORGANISM: Artificial Sequence
<220> FEATURE:
<223> OTHER INFORMATION: FG LOOP

<400> SEQUENCE: 53

Tyr Tyr Lys Glu Ala Asn Tyr Arg Glu Ile
1               5                   10

<210> SEQ ID NO 54
<211> LENGTH: 10
<212> TYPE: PRT
<213> ORGANISM: Artificial Sequence
<220> FEATURE:
<223> OTHER INFORMATION: FG LOOP

<400> SEQUENCE: 54

Tyr Tyr Ala Gln Glu Glu Tyr His Ile Ile
1               5                   10

<210> SEQ ID NO 55
```

```
<211> LENGTH: 10
<212> TYPE: PRT
<213> ORGANISM: Artificial Sequence
<220> FEATURE:
<223> OTHER INFORMATION: FG LOOP

<400> SEQUENCE: 55

Tyr Tyr Lys Glu Ala Asp Tyr Ser Gln Ile
1               5                   10

<210> SEQ ID NO 56
<211> LENGTH: 10
<212> TYPE: PRT
<213> ORGANISM: Artificial Sequence
<220> FEATURE:
<223> OTHER INFORMATION: FG LOOP

<400> SEQUENCE: 56

Tyr Tyr Glu Gln Val Glu Tyr Arg Glu Ile
1               5                   10

<210> SEQ ID NO 57
<211> LENGTH: 10
<212> TYPE: PRT
<213> ORGANISM: Artificial Sequence
<220> FEATURE:
<223> OTHER INFORMATION: FG LOOP

<400> SEQUENCE: 57

Tyr Tyr Glu Gln Pro Ile Tyr Ala Thr Ile
1               5                   10

<210> SEQ ID NO 58
<211> LENGTH: 10
<212> TYPE: PRT
<213> ORGANISM: Artificial Sequence
<220> FEATURE:
<223> OTHER INFORMATION: FG LOOP

<400> SEQUENCE: 58

Tyr Tyr Glu Gln Val Glu Tyr Arg Glu Ile
1               5                   10

<210> SEQ ID NO 59
<211> LENGTH: 10
<212> TYPE: PRT
<213> ORGANISM: Artificial Sequence
<220> FEATURE:
<223> OTHER INFORMATION: FG LOOP

<400> SEQUENCE: 59

Tyr Tyr Ser Glu Glu Leu Tyr Lys Tyr Ile
1               5                   10

<210> SEQ ID NO 60
<211> LENGTH: 109
<212> TYPE: PRT
<213> ORGANISM: Artificial Sequence
<220> FEATURE:
<223> OTHER INFORMATION: Clone ID 1434A08

<400> SEQUENCE: 60

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
                20                  25                  30
```

```
Tyr Tyr Arg Ile Thr Tyr Gly Glu Thr Gly Gly Asn Ser Pro Val Gln
            35                  40                  45

Glu Phe Thr Val Pro His Arg Thr His Thr Ala Thr Ile Ser Gly Leu
 50                      55                  60

Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                 85                  90                  95

Glu Ile Asp Lys Pro Ser Gln His His His His His His
            100                 105

<210> SEQ ID NO 61
<211> LENGTH: 109
<212> TYPE: PRT
<213> ORGANISM: Artificial Sequence
<220> FEATURE:
<223> OTHER INFORMATION: Clone ID 1437G04

<400> SEQUENCE: 61

Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Leu His Val Arg
                20                  25                  30

Tyr Tyr Arg Ile Thr Tyr Gly Glu Thr Gly Gly Asn Ser Pro Val Gln
            35                  40                  45

Glu Phe Thr Val Pro Tyr Tyr His Tyr Thr Ala Thr Ile Ser Gly Leu
 50                      55                  60

Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                 85                  90                  95

Glu Ile Asp Lys Pro Ser Gln His His His His His His
            100                 105

<210> SEQ ID NO 62
<211> LENGTH: 109
<212> TYPE: PRT
<213> ORGANISM: Artificial Sequence
<220> FEATURE:
<223> OTHER INFORMATION: Clone ID 1437A09

<400> SEQUENCE: 62

Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Met His Val Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Lys Gln His Thr Ala Thr Ile Ser Gly Leu
 50                      55                  60

Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                 85                  90                  95

Glu Ile Asp Lys Pro Ser Gln His His His His His His
            100                 105

<210> SEQ ID NO 63
```

```
<211> LENGTH: 109
<212> TYPE: PRT
<213> ORGANISM: Artificial Sequence
<220> FEATURE:
<223> OTHER INFORMATION: Clone ID 1438E05

<400> SEQUENCE: 63

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Asn Val His Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105

<210> SEQ ID NO 64
<211> LENGTH: 109
<212> TYPE: PRT
<213> ORGANISM: Artificial Sequence
<220> FEATURE:
<223> OTHER INFORMATION: Clone ID 1438D01

<400> SEQUENCE: 64

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Asn Arg Ala His Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105

<210> SEQ ID NO 65
<211> LENGTH: 109
<212> TYPE: PRT
<213> ORGANISM: Artificial Sequence
<220> FEATURE:
<223> OTHER INFORMATION: Clone ID 1438B02

<400> SEQUENCE: 65

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45
```

Glu Phe Thr Val Pro Arg Lys Thr Tyr Thr Ala Thr Ile Ser Gly Leu
                50                   55                  60

Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                    85                  90                  95

Glu Ile Asp Lys Pro Ser Gln His His His His His His
                100                 105

<210> SEQ ID NO 66
<211> LENGTH: 109
<212> TYPE: PRT
<213> ORGANISM: Artificial Sequence
<220> FEATURE:
<223> OTHER INFORMATION: Clone ID 1438A09

<400> SEQUENCE: 66

Met Gly Val Ser Asp Val Pro Arg Asp Leu Glu Val Val Ala Ala Thr
 1               5                   10                  15

Pro Thr Ser Leu Leu Ile Ser Trp Gly His Tyr Pro Met His Val Arg
                20                  25                  30

Tyr Tyr Arg Ile Thr Tyr Gly Glu Thr Gly Gly Asn Ser Pro Val Gln
            35                  40                  45

Glu Phe Thr Val Pro Arg Ser Arg Tyr Thr Ala Thr Ile Ser Gly Leu
    50                  55                  60

Lys Pro Gly Val Asp Tyr Thr Ile Thr Val Tyr Ala Val Thr Tyr Tyr
 65                 70                  75                  80

Asn Glu Ala Asp Tyr Ser Gln Ile Pro Ile Ser Ile Asn Tyr Arg Thr
                    85                  90                  95

Glu Ile Asp Lys Pro Ser Gln His His His His His His
                100                 105

<210> SEQ ID NO 67
<211> LENGTH: 109
<212> TYPE: PRT
<213> ORGANISM: Artificial Sequence
<220> FEATURE:
<223> OTHER INFORMATION: Clone ID 1486G03

<400> SEQUENCE: 67

Met Gly Val Ser Asp Val Pro Arg Asp Leu Glu Val Val Ala Ala Thr
 1               5                   10                  15

Pro Thr Ser Leu Leu Ile Ser Trp Gly His Tyr Pro Met His Val Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Arg Tyr Tyr Thr Ala Thr Ile Ser Gly Leu
    50                  55                  60

Lys Pro Gly Val Asp Tyr Thr Ile Thr Val Tyr Ala Val Thr Tyr Tyr
 65                 70                  75                  80

Asn Glu Ala Asp Tyr Ser Gln Ile Pro Ile Ser Ile Asn Tyr Arg Thr
                    85                  90                  95

Glu Ile Asp Lys Pro Ser Gln His His His His His His
                100                 105

<210> SEQ ID NO 68
<211> LENGTH: 109
<212> TYPE: PRT
<213> ORGANISM: Artificial Sequence

```
<220> FEATURE:
<223> OTHER INFORMATION: Clone ID 1486C04

<400> SEQUENCE: 68

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Pro His Arg Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His
            100                 105

<210> SEQ ID NO 69
<211> LENGTH: 109
<212> TYPE: PRT
<213> ORGANISM: Artificial Sequence
<220> FEATURE:
<223> OTHER INFORMATION: Clone ID 1486D04

<400> SEQUENCE: 69

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Ile Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Ser Thr His Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His
            100                 105

<210> SEQ ID NO 70
<211> LENGTH: 109
<212> TYPE: PRT
<213> ORGANISM: Artificial Sequence
<220> FEATURE:
<223> OTHER INFORMATION: Clone ID 1486B05

<400> SEQUENCE: 70

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Arg Ile Tyr Thr Ala Thr Ile Ser Gly Leu
    50                  55                  60
```

```
Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                 85                  90                  95

Glu Ile Asp Lys Pro Ser Gln His His His His His His
            100                 105
```

<210> SEQ ID NO 71
<211> LENGTH: 109
<212> TYPE: PRT
<213> ORGANISM: Artificial Sequence
<220> FEATURE:
<223> OTHER INFORMATION: Clone ID 1486D05

<400> SEQUENCE: 71

```
Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Leu His Val Arg
                 20                  25                  30

Tyr Tyr Arg Ile Thr Tyr Gly Glu Thr Gly Gly Asn Ser Pro Val Gln
             35                  40                  45

Glu Phe Thr Val Pro His Gln Arg Tyr Thr Ala Thr Ile Ser Gly Leu
 50                  55                  60

Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                 85                  90                  95

Glu Ile Asp Lys Pro Ser Gln His His His His His His
            100                 105
```

<210> SEQ ID NO 72
<211> LENGTH: 109
<212> TYPE: PRT
<213> ORGANISM: Artificial Sequence
<220> FEATURE:
<223> OTHER INFORMATION: Clone ID 1487C03

<400> SEQUENCE: 72

```
Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Leu His Ile Arg
                 20                  25                  30

Tyr Tyr Arg Ile Thr Tyr Gly Glu Thr Gly Gly Asn Ser Pro Val Gln
             35                  40                  45

Glu Phe Thr Val Pro Lys Gln Val Tyr Thr Ala Thr Ile Ser Gly Leu
 50                  55                  60

Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                 85                  90                  95

Glu Ile Asp Lys Pro Ser Gln His His His His His His
            100                 105
```

<210> SEQ ID NO 73
<211> LENGTH: 109
<212> TYPE: PRT
<213> ORGANISM: Artificial Sequence
<220> FEATURE:
<223> OTHER INFORMATION: Clone ID 1487G03

-continued

<400> SEQUENCE: 73

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Ala His Arg Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105

<210> SEQ ID NO 74
<211> LENGTH: 109
<212> TYPE: PRT
<213> ORGANISM: Artificial Sequence
<220> FEATURE:
<223> OTHER INFORMATION: Clone ID 1487D09

<400> SEQUENCE: 74

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Ile Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Ser Arg His Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105

<210> SEQ ID NO 75
<211> LENGTH: 109
<212> TYPE: PRT
<213> ORGANISM: Artificial Sequence
<220> FEATURE:
<223> OTHER INFORMATION: Clone ID 1487H04

<400> SEQUENCE: 75

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Ala Arg Gln Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Gln Glu Tyr Glu Tyr Arg Tyr Ile Pro Ile Ser Asn Tyr Arg Thr
                85                  90                  95

Glu Ile Asp Lys Pro Ser Gln His His His His His His
            100                 105

<210> SEQ ID NO 76
<211> LENGTH: 109
<212> TYPE: PRT
<213> ORGANISM: Artificial Sequence
<220> FEATURE:
<223> OTHER INFORMATION: Clone ID 1490E02

<400> SEQUENCE: 76

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
                20                  25                  30

Tyr Tyr Arg Ile Thr Tyr Gly Glu Thr Gly Gly Asn Ser Pro Val Gln
            35                  40                  45

Glu Phe Thr Val Pro Arg Thr Gln Tyr Thr Ala Thr Ile Ser Gly Leu
        50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105

<210> SEQ ID NO 77
<211> LENGTH: 109
<212> TYPE: PRT
<213> ORGANISM: Artificial Sequence
<220> FEATURE:
<223> OTHER INFORMATION: Clone ID 1490G02

<400> SEQUENCE: 77

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
                20                  25                  30

Tyr Tyr Arg Ile Thr Tyr Gly Glu Thr Gly Gly Asn Ser Pro Val Gln
            35                  40                  45

Glu Phe Thr Val Pro Pro Arg Tyr His Thr Ala Thr Ile Ser Gly Leu
        50                  55                  60

Lys Pro Gly Val Asp Tyr Thr Ile Thr Val Tyr Ala Val Thr Tyr Tyr
65                  70                  75                  80

Met Glu Glu Lys Tyr Ala Val Ile Pro Ile Ser Ile Asn Tyr Arg Thr
                85                  90                  95

Glu Ile Asp Lys Pro Ser Gln His His His His His His
            100                 105

<210> SEQ ID NO 78
<211> LENGTH: 109
<212> TYPE: PRT
<213> ORGANISM: Artificial Sequence
<220> FEATURE:
<223> OTHER INFORMATION: Clone ID 1490H05

<400> SEQUENCE: 78

Met Gly Val Ser Asp Val Pro Arg Asp Leu Glu Val Val Ala Ala Thr

```
1               5                   10                  15
Pro Thr Ser Leu Leu Ile Ser Trp Gly His Tyr Pro Leu His Val Arg
            20                  25                  30

Tyr Tyr Arg Ile Thr Tyr Gly Glu Thr Gly Gly Asn Ser Pro Val Gln
            35                  40                  45

Glu Phe Thr Val Pro Met Arg Gln His Thr Ala Thr Ile Ser Gly Leu
        50                  55                  60

Lys Pro Gly Val Asp Tyr Thr Ile Thr Val Tyr Ala Val Thr Tyr Tyr
65                  70                  75                  80

Ala Gln Glu Asn Tyr Lys Glu Ile Pro Ile Ser Ile Asn Tyr Arg Thr
                85                  90                  95

Glu Ile Asp Lys Pro Ser Gln His His His His His
            100                 105

<210> SEQ ID NO 79
<211> LENGTH: 109
<212> TYPE: PRT
<213> ORGANISM: Artificial Sequence
<220> FEATURE:
<223> OTHER INFORMATION: Clone ID 1490B03

<400> SEQUENCE: 79

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Val Arg
            20                  25                  30

Tyr Tyr Arg Ile Thr Tyr Gly Glu Thr Gly Gly Asn Ser Pro Val Gln
            35                  40                  45

Glu Phe Thr Val Pro Ser Arg Lys Tyr Thr Ala Thr Ile Ser Gly Leu
        50                  55                  60

Lys Pro Gly Val Asp Tyr Thr Ile Thr Val Tyr Ala Val Thr Tyr Tyr
65                  70                  75                  80

Lys Glu Ala Asn Tyr Arg Glu Ile Pro Ile Ser Ile Asn Tyr Arg Thr
                85                  90                  95

Glu Ile Asp Lys Pro Ser Gln His His His His His
            100                 105

<210> SEQ ID NO 80
<211> LENGTH: 109
<212> TYPE: PRT
<213> ORGANISM: Artificial Sequence
<220> FEATURE:
<223> OTHER INFORMATION: Clone ID 1490H06

<400> SEQUENCE: 80

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Ile Arg
            20                  25                  30

Tyr Tyr Arg Ile Thr Tyr Gly Glu Thr Gly Gly Asn Ser Pro Val Gln
            35                  40                  45

Glu Phe Thr Val Pro Arg Gln Lys Tyr Thr Ala Thr Ile Ser Gly Leu
        50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95
```

```
Glu Ile Asp Lys Pro Ser Gln His His His His His His
            100                 105
```

<210> SEQ ID NO 81
<211> LENGTH: 109
<212> TYPE: PRT
<213> ORGANISM: Artificial Sequence
<220> FEATURE:
<223> OTHER INFORMATION: Clone ID 1490A07

<400> SEQUENCE: 81

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Ile Arg
            20                  25                  30

Tyr Tyr Arg Ile Thr Tyr Gly Glu Thr Gly Gly Asn Ser Pro Val Gln
        35                  40                  45

Glu Phe Thr Val Pro His Ala Lys Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Ala Gln Glu Asn Tyr Lys Glu Ile Pro Ile Ser Ile Asn Tyr Arg Thr
                85                  90                  95

Glu Ile Asp Lys Pro Ser Gln His His His His His His
            100                 105
```

<210> SEQ ID NO 82
<211> LENGTH: 109
<212> TYPE: PRT
<213> ORGANISM: Artificial Sequence
<220> FEATURE:
<223> OTHER INFORMATION: Clone ID 1490C07

<400> SEQUENCE: 82

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Asn Arg Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105
```

<210> SEQ ID NO 83
<211> LENGTH: 109
<212> TYPE: PRT
<213> ORGANISM: Artificial Sequence
<220> FEATURE:
<223> OTHER INFORMATION: Clone ID 1490H08

<400> SEQUENCE: 83

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Ile Arg
```

```
                20                  25                  30
Tyr Tyr Arg Ile Thr Tyr Gly Glu Thr Gly Gly Asn Ser Pro Val Gln
            35                  40                  45
Glu Phe Thr Val Pro Asn Thr Ser His Thr Ala Thr Ile Ser Gly Leu
        50                  55                  60
Lys Pro Gly Val Asp Tyr Thr Ile Thr Val Tyr Ala Val Thr Tyr Tyr
65                  70                  75                  80
Asn Glu Ala Asp Tyr Ser Gln Ile Pro Ile Ser Ile Asn Tyr Arg Thr
                85                  90                  95
Glu Ile Asp Lys Pro Ser Gln His His His His His His
                100                 105
```

<210> SEQ ID NO 84
<211> LENGTH: 109
<212> TYPE: PRT
<213> ORGANISM: Artificial Sequence
<220> FEATURE:
<223> OTHER INFORMATION: Clone ID 1491A05

<400> SEQUENCE: 84

```
Met Gly Val Ser Asp Val Pro Arg Asp Leu Glu Val Val Ala Ala Thr
1               5                   10                  15
Pro Thr Ser Leu Leu Ile Ser Trp Gly His Tyr Pro Leu His Val Arg
                20                  25                  30
Tyr Tyr Arg Ile Thr Tyr Gly Glu Thr Gly Gly Asn Ser Pro Val Gln
            35                  40                  45
Glu Phe Thr Val Pro Ser Gln Val Tyr Thr Ala Thr Ile Ser Gly Leu
        50                  55                  60
Lys Pro Gly Val Asp Tyr Thr Ile Thr Val Tyr Ala Val Thr Tyr Tyr
65                  70                  75                  80
Ala Gln Glu Asn Tyr Lys Gln Ile Pro Ile Ser Ile Asn Tyr Arg Thr
                85                  90                  95
Glu Ile Asp Lys Pro Ser Gln His His His His His His
                100                 105
```

<210> SEQ ID NO 85
<211> LENGTH: 109
<212> TYPE: PRT
<213> ORGANISM: Artificial Sequence
<220> FEATURE:
<223> OTHER INFORMATION: Clone ID 1571H03

<400> SEQUENCE: 85

```
Met Gly Val Ser Asp Val Pro Arg Asp Leu Glu Val Val Ala Ala Thr
1               5                   10                  15
Pro Thr Ser Leu Leu Ile Ser Trp Gly His Tyr Pro Leu His Val Arg
                20                  25                  30
Tyr Tyr Arg Ile Thr Tyr Gly Glu Thr Gly Gly Asn Ser Pro Val Gln
            35                  40                  45
Glu Phe Thr Val Pro Asn Arg Val Tyr Thr Ala Thr Ile Ser Gly Leu
        50                  55                  60
Lys Pro Gly Val Asp Tyr Thr Ile Thr Val Tyr Ala Val Thr Tyr Tyr
65                  70                  75                  80
Ala Gln Glu Glu Tyr His Ile Ile Pro Ile Ser Ile Asn Tyr Arg Thr
                85                  90                  95
Glu Ile Asp Lys Pro Ser Gln His His His His His His
                100                 105
```

<210> SEQ ID NO 86
<211> LENGTH: 109
<212> TYPE: PRT
<213> ORGANISM: Artificial Sequence
<220> FEATURE:
<223> OTHER INFORMATION: Clone ID 1571G04

<400> SEQUENCE: 86

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Pro Arg Ser His Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Ala Gln Glu Asn Tyr Lys Glu Ile Pro Ile Ser Ile Asn Tyr Arg Thr
                85                  90                  95

Glu Ile Asp Lys Pro Ser Gln His His His His His His
            100                 105
```

<210> SEQ ID NO 87
<211> LENGTH: 109
<212> TYPE: PRT
<213> ORGANISM: Artificial Sequence
<220> FEATURE:
<223> OTHER INFORMATION: Clone ID 1571G06

<400> SEQUENCE: 87

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Leu Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Thr Lys Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Lys Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105
```

<210> SEQ ID NO 88
<211> LENGTH: 109
<212> TYPE: PRT
<213> ORGANISM: Artificial Sequence
<220> FEATURE:
<223> OTHER INFORMATION: Clone ID 1571F10

<400> SEQUENCE: 88

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Ile Arg
            20                  25                  30

Tyr Tyr Arg Ile Thr Tyr Gly Glu Thr Gly Gly Asn Ser Pro Val Gln
```

```
            35                  40                  45
Glu Phe Thr Val Pro Ser Arg Tyr His Thr Ala Thr Ile Ser Gly Leu
     50                  55                  60
Lys Pro Gly Val Asp Tyr Thr Ile Thr Val Tyr Ala Val Thr Tyr Tyr
65                   70                  75                  80
Glu Gln Val Glu Tyr Arg Glu Ile Pro Ile Ser Ile Asn Tyr Arg Thr
                 85                  90                  95
Glu Ile Asp Lys Pro Ser Gln His His His His His His
                100                 105
```

<210> SEQ ID NO 89
<211> LENGTH: 109
<212> TYPE: PRT
<213> ORGANISM: Artificial Sequence
<220> FEATURE:
<223> OTHER INFORMATION: Clone ID 1572D04

<400> SEQUENCE: 89

```
Met Gly Val Ser Asp Val Pro Arg Asp Leu Glu Val Val Ala Ala Thr
1               5                   10                  15
Pro Thr Ser Leu Leu Ile Ser Trp Gly His Tyr Pro Met His Val Arg
                 20                  25                  30
Tyr Tyr Arg Ile Thr Tyr Gly Glu Thr Gly Gly Asn Ser Pro Val Gln
             35                  40                  45
Glu Phe Thr Val Pro Pro Arg Arg Tyr Thr Ala Thr Ile Ser Gly Leu
     50                  55                  60
Lys Pro Gly Val Asp Tyr Thr Ile Thr Val Tyr Ala Val Thr Tyr Tyr
65                   70                  75                  80
Glu Gln Pro Ile Tyr Ala Thr Ile Pro Ile Ser Ile Asn Tyr Arg Thr
                 85                  90                  95
Glu Ile Asp Lys Pro Ser Gln His His His His His
                100                 105
```

<210> SEQ ID NO 90
<211> LENGTH: 109
<212> TYPE: PRT
<213> ORGANISM: Artificial Sequence
<220> FEATURE:
<223> OTHER INFORMATION: Clone ID 1572F05

<400> SEQUENCE: 90

```
Met Gly Val Ser Asp Val Pro Arg Asp Leu Glu Val Val Ala Ala Thr
1               5                   10                  15
Pro Thr Ser Leu Leu Ile Ser Trp Gly His Tyr Pro Leu His Ile Arg
                 20                  25                  30
Tyr Tyr Arg Ile Thr Tyr Gly Glu Thr Gly Gly Asn Ser Pro Val Gln
             35                  40                  45
Glu Phe Thr Val Pro Arg Gln Lys Tyr Thr Ala Thr Ile Ser Gly Leu
     50                  55                  60
Lys Pro Gly Val Asp Tyr Thr Ile Thr Val Tyr Ala Val Thr Tyr Tyr
65                   70                  75                  80
Asn Glu Ala Asp Tyr Ser Gln Ile Pro Ile Ser Ile Asn Tyr Arg Thr
                 85                  90                  95
Glu Ile Asp Lys Pro Ser Gln His His His His His
                100                 105
```

<210> SEQ ID NO 91
<211> LENGTH: 109

-continued

```
<212> TYPE: PRT
<213> ORGANISM: Artificial Sequence
<220> FEATURE:
<223> OTHER INFORMATION: Clone ID 1572G06

<400> SEQUENCE: 91

Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Leu His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Tyr Lys Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Ala Gln Glu Asn Tyr Lys Glu Ile Pro Ile Ser Ile Asn Tyr Arg Thr
                85                  90                  95

Glu Ile Asp Lys Pro Ser Gln His His His His His His
            100                 105

<210> SEQ ID NO 92
<211> LENGTH: 109
<212> TYPE: PRT
<213> ORGANISM: Artificial Sequence
<220> FEATURE:
<223> OTHER INFORMATION: Clone ID 1572B10

<400> SEQUENCE: 92

Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Val Pro Arg His Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105

<210> SEQ ID NO 93
<211> LENGTH: 109
<212> TYPE: PRT
<213> ORGANISM: Artificial Sequence
<220> FEATURE:
<223> OTHER INFORMATION: Clone ID 1572C09

<400> SEQUENCE: 93

Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Met His Ile Arg
            20                  25                  30

Tyr Tyr Arg Ile Thr Tyr Gly Glu Thr Gly Gly Asn Ser Pro Val Gln
        35                  40                  45

Glu Phe Thr Val Pro Thr Pro Lys His Thr Ala Thr Ile Ser Gly Leu
```

```
                50                  55                  60
Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                 85                  90                  95

Glu Ile Asp Lys Pro Ser Gln His His His His His His
                100                 105
```

<210> SEQ ID NO 94
<211> LENGTH: 109
<212> TYPE: PRT
<213> ORGANISM: Artificial Sequence
<220> FEATURE:
<223> OTHER INFORMATION: Clone ID 1572H05

<400> SEQUENCE: 94

```
Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Leu His Ile Arg
                20                  25                  30

Tyr Tyr Arg Ile Thr Tyr Gly Glu Thr Gly Gly Asn Ser Pro Val Gln
                35                  40                  45

Glu Phe Thr Val Pro Arg Ser Lys Tyr Thr Ala Thr Ile Ser Gly Leu
 50                  55                  60

Lys Pro Gly Val Asp Tyr Thr Ile Thr Val Tyr Ala Val Thr Tyr Tyr
 65                  70                  75                  80

Glu Gln Val Glu Tyr Arg Glu Ile Pro Ile Ser Ile Asn Tyr Arg Thr
                 85                  90                  95

Glu Ile Asp Lys Pro Ser Gln His His His His His His
                100                 105
```

<210> SEQ ID NO 95
<211> LENGTH: 109
<212> TYPE: PRT
<213> ORGANISM: Artificial Sequence
<220> FEATURE:
<223> OTHER INFORMATION: Clone ID 1572H08

<400> SEQUENCE: 95

```
Met Gly Val Ser Asp Val Pro Arg Asp Leu Glu Val Val Ala Ala Thr
 1               5                  10                  15

Pro Thr Ser Leu Leu Ile Ser Trp Gly His Tyr Pro Leu His Val Arg
                20                  25                  30

Tyr Tyr Arg Ile Thr Tyr Gly Glu Thr Gly Gly Asn Ser Pro Val Gln
                35                  40                  45

Glu Phe Thr Val Pro Ser Arg Lys Tyr Thr Ala Thr Ile Ser Gly Leu
 50                  55                  60

Lys Pro Gly Val Asp Tyr Thr Ile Thr Val Tyr Ala Val Thr Tyr Tyr
 65                  70                  75                  80

Asn Glu Ala Asp Tyr Ser Gln Ile Pro Ile Ser Ile Asn Tyr Arg Thr
                 85                  90                  95

Glu Ile Asp Lys Pro Ser Gln His His His His His His
                100                 105
```

<210> SEQ ID NO 96
<211> LENGTH: 109
<212> TYPE: PRT
<213> ORGANISM: Artificial Sequence
<220> FEATURE:

<223> OTHER INFORMATION: Clone ID 1550A07

<400> SEQUENCE: 96

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Val Pro Arg Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Ala Gln Glu Asn Tyr Lys Glu Ile Pro Ile Ser Ile Asn Tyr Arg Thr
                85                  90                  95

Glu Ile Asp Lys Pro Ser Gln His His His His His His
            100                 105

<210> SEQ ID NO 97
<211> LENGTH: 109
<212> TYPE: PRT
<213> ORGANISM: Artificial Sequence
<220> FEATURE:
<223> OTHER INFORMATION: Clone ID 1550C05

<400> SEQUENCE: 97

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Pro Arg Arg Tyr Thr Ala Thr Ile Ser Gly Leu
    50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
            100                 105

<210> SEQ ID NO 98
<211> LENGTH: 109
<212> TYPE: PRT
<213> ORGANISM: Artificial Sequence
<220> FEATURE:
<223> OTHER INFORMATION: Clone ID 1550E03

<400> SEQUENCE: 98

Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Ile Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Met Arg His Thr Ala Thr Ile Ser Gly Leu
    50                  55                  60

Lys Pro Gly Val Asp Tyr Thr Ile Thr Val Tyr Ala Val Thr Tyr Tyr

```
                65                  70                  75                  80
Ser Glu Glu Leu Tyr Lys Tyr Ile Pro Ile Ser Ile Asn Tyr Arg Thr
                    85                  90                  95

Glu Ile Asp Lys Pro Ser Gln His His His His His His
                100                 105
```

<210> SEQ ID NO 99
<211> LENGTH: 109
<212> TYPE: PRT
<213> ORGANISM: Artificial Sequence
<220> FEATURE:
<223> OTHER INFORMATION: Clone ID 1550E06

<400> SEQUENCE: 99

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Met His Val Arg
                20                  25                  30

Tyr Tyr Arg Ile Thr Tyr Gly Glu Thr Gly Gly Asn Ser Pro Val Gln
                35                  40                  45

Glu Phe Thr Val Pro Pro Arg His Thr Ala Thr Ile Ser Gly Leu
50                  55                  60

Lys Pro Gly Val Asp Tyr Thr Ile Thr Val Tyr Ala Val Thr Tyr Tyr
65                  70                  75                  80

Ala Gln Glu Asn Tyr Lys Glu Ile Pro Ile Ser Ile Asn Tyr Arg Thr
                85                  90                  95

Glu Ile Asp Lys Pro Ser Gln His His His His His His
                100                 105
```

<210> SEQ ID NO 100
<211> LENGTH: 109
<212> TYPE: PRT
<213> ORGANISM: Artificial Sequence
<220> FEATURE:
<223> OTHER INFORMATION: Clone ID 1550H05

<400> SEQUENCE: 100

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Pro Leu His Val Arg
                20                  25                  30

Tyr Tyr Arg Ile Thr Tyr Gly Glu Thr Gly Gly Asn Ser Pro Val Gln
                35                  40                  45

Glu Phe Thr Val Pro Arg Gln Ile Tyr Thr Ala Thr Ile Ser Gly Leu
50                  55                  60

Lys Pro Gly Val Asp Tyr Thr Ile Thr Val Tyr Ala Val Thr Tyr Tyr
65                  70                  75                  80

Asn Glu Ala Asp Tyr Ser Gln Ile Pro Ile Ser Ile Asn Tyr Arg Thr
                85                  90                  95

Glu Ile Asp Lys Pro Ser Gln His His His His His His
                100                 105
```

<210> SEQ ID NO 101
<211> LENGTH: 4
<212> TYPE: PRT
<213> ORGANISM: Artificial Sequence
<220> FEATURE:
<223> OTHER INFORMATION: Cys containing c-terminus linker

<400> SEQUENCE: 101

```
Gly Ser Gly Cys
1
```

<210> SEQ ID NO 102
<211> LENGTH: 7
<212> TYPE: PRT
<213> ORGANISM: Artificial Sequence
<220> FEATURE:
<223> OTHER INFORMATION: Cys containing c-terminus linker

<400> SEQUENCE: 102

```
Glu Ile Asp Lys Pro Cys Gln
1               5
```

<210> SEQ ID NO 103
<211> LENGTH: 82
<212> TYPE: PRT
<213> ORGANISM: Artificial Sequence
<220> FEATURE:
<223> OTHER INFORMATION: Core 1 Adnectin

<400> SEQUENCE: 103

```
Glu Val Val Ala Ala Thr Pro Thr Ser Leu Leu Ile Ser Trp His Ser
1               5                   10                  15

Tyr Tyr Glu Gln Asn Ser Tyr Tyr Arg Ile Thr Tyr Gly Glu Thr Gly
                20                  25                  30

Gly Asn Ser Pro Val Gln Glu Phe Thr Val Pro Tyr Ser Gln Thr Thr
            35                  40                  45

Ala Thr Ile Ser Gly Leu Lys Pro Gly Val Asp Tyr Thr Ile Thr Val
        50                  55                  60

Tyr Ala Val Tyr Gly Ser Lys Tyr Tyr Pro Ile Ser Ile Asn Tyr
65                  70                  75                  80

Arg Thr
```

<210> SEQ ID NO 104
<211> LENGTH: 8
<212> TYPE: PRT
<213> ORGANISM: Artificial Sequence
<220> FEATURE:
<223> OTHER INFORMATION: Core 1 BC LOOP

<400> SEQUENCE: 104

```
His Ser Tyr Tyr Glu Gln Asn Ser
1               5
```

<210> SEQ ID NO 105
<211> LENGTH: 4
<212> TYPE: PRT
<213> ORGANISM: Artificial Sequence
<220> FEATURE:
<223> OTHER INFORMATION: Core 1 DE LOOP

<400> SEQUENCE: 105

```
Tyr Ser Gln Thr
1
```

<210> SEQ ID NO 106
<211> LENGTH: 7
<212> TYPE: PRT
<213> ORGANISM: Artificial Sequence
<220> FEATURE:
<223> OTHER INFORMATION: Core 1 FG LOOP

<400> SEQUENCE: 106

Tyr Gly Ser Lys Tyr Tyr Tyr
1               5

<210> SEQ ID NO 107
<211> LENGTH: 86
<212> TYPE: PRT
<213> ORGANISM: Artificial Sequence
<220> FEATURE:
<223> OTHER INFORMATION: Core 2 Adnectin

<400> SEQUENCE: 107

Glu Val Val Ala Ala Thr Pro Thr Ser Leu Leu Ile Ser Trp Pro Lys
1               5                   10                  15

Tyr Asp Lys Thr Gly His Tyr Tyr Arg Ile Thr Tyr Gly Glu Thr Gly
                20                  25                  30

Gly Asn Ser Pro Val Gln Glu Phe Thr Val Pro Thr Arg Gln Thr Thr
            35                  40                  45

Ala Thr Ile Ser Gly Leu Lys Pro Gly Val Asp Tyr Thr Ile Thr Val
        50                  55                  60

Tyr Ala Val Ser Lys Asp Asp Tyr Tyr Pro His Glu His Arg Pro Ile
65                  70                  75                  80

Ser Ile Asn Tyr Arg Thr
                85

<210> SEQ ID NO 108
<211> LENGTH: 8
<212> TYPE: PRT
<213> ORGANISM: Artificial Sequence
<220> FEATURE:
<223> OTHER INFORMATION: Core 2 BC LOOP

<400> SEQUENCE: 108

Pro Lys Tyr Asp Lys Thr Gly His
1               5

<210> SEQ ID NO 109
<211> LENGTH: 4
<212> TYPE: PRT
<213> ORGANISM: Artificial Sequence
<220> FEATURE:
<223> OTHER INFORMATION: Core 2 DE LOOP

<400> SEQUENCE: 109

Thr Arg Gln Thr
1

<210> SEQ ID NO 110
<211> LENGTH: 11
<212> TYPE: PRT
<213> ORGANISM: Artificial Sequence
<220> FEATURE:
<223> OTHER INFORMATION: Core 2 FG LOOP

<400> SEQUENCE: 110

Ser Lys Asp Asp Tyr Tyr Pro His Glu His Arg
1               5                   10

<210> SEQ ID NO 111
<211> LENGTH: 86
<212> TYPE: PRT
<213> ORGANISM: Artificial Sequence
<220> FEATURE:
<223> OTHER INFORMATION: Core 3 Adnectin

```
<400> SEQUENCE: 111

Glu Val Ala Ala Thr Pro Thr Ser Leu Leu Ile Ser Trp Ser Asn
1               5                   10                  15

Asp Gly Pro Gly Leu Ser Tyr Tyr Arg Ile Thr Tyr Gly Glu Thr Gly
            20                  25                  30

Gly Asn Ser Pro Val Gln Glu Phe Thr Val Pro Ser Ser Gln Thr Thr
                35                  40                  45

Ala Thr Ile Ser Gly Leu Lys Pro Gly Val Asp Tyr Thr Ile Thr Val
    50                  55                  60

Tyr Ala Val Ser Tyr Tyr Thr Lys Lys Ala Tyr Ser Ala Gly Pro Ile
65                  70                  75                  80

Ser Ile Asn Tyr Arg Thr
                85

<210> SEQ ID NO 112
<211> LENGTH: 8
<212> TYPE: PRT
<213> ORGANISM: Artificial Sequence
<220> FEATURE:
<223> OTHER INFORMATION: Core 3 BE LOOP

<400> SEQUENCE: 112

Ser Asn Asp Gly Pro Gly Leu Ser
1               5

<210> SEQ ID NO 113
<211> LENGTH: 4
<212> TYPE: PRT
<213> ORGANISM: Artificial Sequence
<220> FEATURE:
<223> OTHER INFORMATION: Core 3 DE LOOP

<400> SEQUENCE: 113

Ser Ser Gln Thr
1

<210> SEQ ID NO 114
<211> LENGTH: 11
<212> TYPE: PRT
<213> ORGANISM: Artificial Sequence
<220> FEATURE:
<223> OTHER INFORMATION: Core 3 FG LOOP

<400> SEQUENCE: 114

Ser Tyr Tyr Thr Lys Lys Ala Tyr Ser Ala Gly
1               5                   10

<210> SEQ ID NO 115
<211> LENGTH: 86
<212> TYPE: PRT
<213> ORGANISM: Artificial Sequence
<220> FEATURE:
<223> OTHER INFORMATION: Core 4 Adnectin

<400> SEQUENCE: 115

Glu Met Val Ala Ala Thr Pro Thr Ser Leu Leu Ile Ser Trp Glu Asp
1               5                   10                  15

Asp Ser Tyr Tyr Ser Arg Tyr Tyr Arg Ile Thr Tyr Gly Glu Thr Gly
            20                  25                  30

Gly Asn Ser Pro Val Gln Glu Phe Thr Val Pro Ser Asp Leu Tyr Thr
                35                  40                  45

Ala Thr Ile Ser Gly Leu Lys Pro Gly Val Asp Tyr Thr Ile Thr Val
```

-continued

```
                50                  55                  60
Tyr Ala Val Thr Tyr Asp Val Thr Asp Leu Ile Met His Glu Pro Ile
 65                  70                  75                  80

Ser Ile Asn Tyr Arg Thr
                 85

<210> SEQ ID NO 116
<211> LENGTH: 8
<212> TYPE: PRT
<213> ORGANISM: Artificial Sequence
<220> FEATURE:
<223> OTHER INFORMATION: Core 4 BC LOOP

<400> SEQUENCE: 116

Glu Asp Asp Ser Tyr Tyr Ser Arg
 1               5

<210> SEQ ID NO 117
<211> LENGTH: 4
<212> TYPE: PRT
<213> ORGANISM: Artificial Sequence
<220> FEATURE:
<223> OTHER INFORMATION: Core 4 DE LOOP

<400> SEQUENCE: 117

Ser Asp Leu Tyr
 1

<210> SEQ ID NO 118
<211> LENGTH: 10
<212> TYPE: PRT
<213> ORGANISM: Artificial Sequence
<220> FEATURE:
<223> OTHER INFORMATION: Core 4 FG LOOP

<400> SEQUENCE: 118

Tyr Asp Val Thr Asp Leu Ile Met His Glu
 1               5                  10

<210> SEQ ID NO 119
<211> LENGTH: 86
<212> TYPE: PRT
<213> ORGANISM: Artificial Sequence
<220> FEATURE:
<223> OTHER INFORMATION: Core 5 Adnectin

<400> SEQUENCE: 119

Glu Val Val Ala Ala Thr Pro Thr Ser Leu Leu Ile Ser Trp Glu Asp
 1               5                  10                  15

Asp Ser Tyr Tyr Ser Arg Tyr Tyr Arg Ile Thr Tyr Gly Glu Thr Gly
                 20                  25                  30

Gly Asn Ser Pro Val Gln Glu Phe Thr Val Pro Ser Asp Leu Tyr Thr
         35                  40                  45

Ala Thr Ile Ser Gly Leu Lys Pro Gly Val Asp Tyr Thr Ile Thr Val
     50                  55                  60

Tyr Ala Val Thr Tyr Asp Val Thr Asp Leu Ile Met His Glu Pro Ile
 65                  70                  75                  80

Ser Ile Asn Tyr Arg Thr
                 85

<210> SEQ ID NO 120
<211> LENGTH: 8
<212> TYPE: PRT
```

```
<213> ORGANISM: Artificial Sequence
<220> FEATURE:
<223> OTHER INFORMATION: Core 5 BC LOOP

<400> SEQUENCE: 120

Glu Asp Asp Ser Tyr Tyr Ser Arg
1               5

<210> SEQ ID NO 121
<211> LENGTH: 4
<212> TYPE: PRT
<213> ORGANISM: Artificial Sequence
<220> FEATURE:
<223> OTHER INFORMATION: Core 5 DE LOOP

<400> SEQUENCE: 121

Ser Asp Leu Tyr
1

<210> SEQ ID NO 122
<211> LENGTH: 10
<212> TYPE: PRT
<213> ORGANISM: Artificial Sequence
<220> FEATURE:
<223> OTHER INFORMATION: Core 5 FG LOOP

<400> SEQUENCE: 122

Tyr Asp Val Thr Asp Leu Ile Met His Glu
1               5                   10

<210> SEQ ID NO 123
<211> LENGTH: 86
<212> TYPE: PRT
<213> ORGANISM: Artificial Sequence
<220> FEATURE:
<223> OTHER INFORMATION: Core 6 Adnectin

<400> SEQUENCE: 123

Glu Val Val Ala Ala Thr Pro Thr Ser Leu Leu Ile Ser Trp Tyr Met
1               5                   10                  15

Asp Glu Tyr Asp Val Arg Tyr Tyr Arg Ile Thr Tyr Gly Glu Thr Gly
            20                  25                  30

Gly Asn Ser Pro Val Gln Glu Phe Thr Val Pro Asn Tyr Tyr Asn Thr
        35                  40                  45

Ala Thr Ile Ser Gly Leu Lys Pro Gly Val Asp Tyr Thr Ile Thr Val
    50                  55                  60

Tyr Ala Val Thr Arg Ile Lys Ala Asn Asn Tyr Met Tyr Gly Pro Ile
65                  70                  75                  80

Ser Ile Asn Tyr Arg Thr
                85

<210> SEQ ID NO 124
<211> LENGTH: 86
<212> TYPE: PRT
<213> ORGANISM: Artificial Sequence
<220> FEATURE:
<223> OTHER INFORMATION: Core 7 Adnectin

<400> SEQUENCE: 124

Glu Val Val Ala Ala Thr Pro Thr Ser Leu Leu Ile Ser Trp Asn His
1               5                   10                  15

Leu Glu His Val Ala Arg Tyr Tyr Arg Ile Thr Tyr Gly Glu Thr Gly
            20                  25                  30
```

-continued

```
Gly Asn Ser Pro Val Gln Glu Phe Thr Val Pro Glu Tyr Pro Thr Thr
            35                  40                  45

Ala Thr Ile Ser Gly Leu Lys Pro Gly Val Asp Tyr Thr Ile Thr Val
 50                  55                  60

Tyr Ala Val Thr Ile Thr Met Leu Lys Tyr Pro Thr Gln Ser Pro Ile
 65                  70                  75                  80

Ser Ile Asn Tyr Arg Thr
                85
```

<210> SEQ ID NO 125
<211> LENGTH: 86
<212> TYPE: PRT
<213> ORGANISM: Artificial Sequence
<220> FEATURE:
<223> OTHER INFORMATION: Core 8 Adnectin

<400> SEQUENCE: 125

```
Glu Val Val Ala Ala Thr Pro Thr Ser Leu Leu Ile Ser Trp Gly His
 1               5                  10                  15

Tyr Arg Arg Ser Gly His Tyr Tyr Arg Ile Thr Tyr Gly Glu Thr Gly
            20                  25                  30

Gly Asn Ser Pro Val Gln Glu Phe Thr Val Asp Pro Ser Ser Tyr Thr
            35                  40                  45

Ala Thr Ile Ser Gly Leu Lys Pro Gly Val Asp Tyr Thr Ile Thr Val
 50                  55                  60

Tyr Ala Val Ser Lys Asp Asp Tyr Tyr Pro His Glu His Arg Pro Ile
 65                  70                  75                  80

Ser Ile Asn Tyr Arg Thr
                85
```

<210> SEQ ID NO 126
<211> LENGTH: 84
<212> TYPE: PRT
<213> ORGANISM: Artificial Sequence
<220> FEATURE:
<223> OTHER INFORMATION: Core 9 Adnectin

<400> SEQUENCE: 126

```
Glu Val Val Ala Ala Thr Pro Thr Ser Leu Leu Ile Ser Trp Asp Ala
 1               5                  10                  15

Ser His Tyr Glu Arg Arg Tyr Tyr Arg Ile Thr Tyr Gly Glu Thr Gly
            20                  25                  30

Gly Asn Ser Pro Val Gln Glu Phe Thr Val Pro Arg Tyr His His Thr
            35                  40                  45

Ala Thr Ile Ser Gly Leu Lys Pro Gly Val Asp Tyr Thr Ile Thr Val
 50                  55                  60

Tyr Ala Val Thr Gln Ala Gln Glu His Tyr Gln Pro Pro Ile Ser Ile
 65                  70                  75                  80

Asn Tyr Arg Thr
```

<210> SEQ ID NO 127
<211> LENGTH: 82
<212> TYPE: PRT
<213> ORGANISM: Artificial Sequence
<220> FEATURE:
<223> OTHER INFORMATION: Core 10 Adnectin

<400> SEQUENCE: 127

```
Glu Val Val Ala Ala Thr Pro Thr Ser Leu Leu Ile Ser Trp Asn Ser
 1               5                  10                  15
```

Tyr Tyr His Ser Ala Asp Tyr Arg Ile Thr Tyr Gly Glu Thr Gly
            20                  25                  30

Gly Asn Ser Pro Val Gln Glu Phe Thr Val Pro Tyr Pro Thr Thr
            35                  40                  45

Ala Thr Ile Ser Gly Leu Lys Pro Gly Val Asp Tyr Thr Ile Thr Val
 50                  55                  60

Tyr Ala Val Tyr Ser Ala Lys Ser Tyr Tyr Pro Ile Ser Ile Asn Tyr
 65                  70                  75                  80

Arg Thr

<210> SEQ ID NO 128
<211> LENGTH: 86
<212> TYPE: PRT
<213> ORGANISM: Artificial Sequence
<220> FEATURE:
<223> OTHER INFORMATION: Core 11 Adnectin

<400> SEQUENCE: 128

Glu Val Val Ala Ala Thr Pro Thr Ser Leu Leu Ile Ser Trp Ser Lys
 1               5                  10                  15

Tyr Ser Lys His Gly His Tyr Tyr Arg Ile Thr Tyr Gly Glu Thr Gly
            20                  25                  30

Gly Asn Ser Pro Val Gln Glu Phe Thr Val Pro Ser Gly Asn Ala Thr
            35                  40                  45

Ala Thr Ile Ser Gly Leu Lys Pro Gly Val Asp Tyr Thr Ile Thr Val
 50                  55                  60

Tyr Ala Val Glu Asp Thr Asn Asp Tyr Pro His Thr His Arg Pro Ile
 65                  70                  75                  80

Ser Ile Asn Tyr Arg Thr
                85

<210> SEQ ID NO 129
<211> LENGTH: 84
<212> TYPE: PRT
<213> ORGANISM: Artificial Sequence
<220> FEATURE:
<223> OTHER INFORMATION: Core 12 Adnectin

<400> SEQUENCE: 129

Glu Val Val Ala Ala Thr Pro Thr Ser Leu Leu Ile Ser Trp His Gly
 1               5                  10                  15

Glu Pro Asp Gln Thr Arg Tyr Tyr Arg Ile Thr Tyr Gly Glu Thr Gly
            20                  25                  30

Gly Asn Ser Pro Val Gln Glu Phe Thr Val Pro Pro Tyr Arg Arg Thr
            35                  40                  45

Ala Thr Ile Ser Gly Leu Lys Pro Gly Val Asp Tyr Thr Ile Thr Val
 50                  55                  60

Tyr Ala Val Thr Ser Gly Tyr Thr Gly His Tyr Gln Pro Ile Ser Ile
 65                  70                  75                  80

Asn Tyr Arg Thr

<210> SEQ ID NO 130
<211> LENGTH: 86
<212> TYPE: PRT
<213> ORGANISM: Artificial Sequence
<220> FEATURE:
<223> OTHER INFORMATION: Core 13 Adnectin

<400> SEQUENCE: 130

Glu Val Val Ala Ala Thr Pro Thr Ser Leu Leu Ile Ser Trp Ser Lys
1               5                   10                  15

Tyr Ser Lys His Gly His Tyr Tyr Arg Ile Thr Tyr Gly Glu Thr Gly
                20                  25                  30

Gly Asn Ser Pro Val Gln Glu Phe Thr Val Asp Pro Ser Ser Tyr Thr
            35                  40                  45

Ala Thr Ile Ser Gly Leu Lys Pro Gly Val Asp Tyr Thr Ile Thr Val
        50                  55                  60

Tyr Ala Val Ser Lys Asp Asp Tyr Pro His Glu His Arg Pro Ile
65                  70                  75                  80

Ser Ile Asn Tyr Arg Thr
                85

<210> SEQ ID NO 131
<211> LENGTH: 82
<212> TYPE: PRT
<213> ORGANISM: Artificial Sequence
<220> FEATURE:
<223> OTHER INFORMATION: Core 14 Adnectin

<400> SEQUENCE: 131

Glu Val Val Ala Ala Thr Pro Thr Ser Leu Leu Ile Ser Trp Tyr Glu
1               5                   10                  15

Pro Tyr Thr Pro Ile His Tyr Tyr Arg Ile Thr Tyr Gly Glu Thr Gly
                20                  25                  30

Gly Asn Ser Pro Val Gln Glu Phe Thr Val Pro Gly Tyr Tyr Gly Thr
            35                  40                  45

Ala Thr Ile Ser Gly Leu Lys Pro Gly Val Asp Tyr Thr Ile Thr Val
        50                  55                  60

Tyr Ala Val Tyr Gly Tyr Tyr Gln Tyr Thr Pro Ile Ser Ile Asn Tyr
65                  70                  75                  80

Arg Thr

<210> SEQ ID NO 132
<211> LENGTH: 86
<212> TYPE: PRT
<213> ORGANISM: Artificial Sequence
<220> FEATURE:
<223> OTHER INFORMATION: Core 15 Adnectin

<400> SEQUENCE: 132

Glu Val Val Ala Ala Thr Pro Thr Ser Leu Leu Ile Ser Trp Ser Lys
1               5                   10                  15

Tyr Ser Lys His Gly His Tyr Tyr Arg Ile Thr Tyr Gly Glu Thr Gly
                20                  25                  30

Gly Asn Ser Pro Val Gln Glu Phe Thr Val Pro Ser Gly Asn Ala Thr
            35                  40                  45

Ala Thr Ile Ser Gly Leu Lys Pro Gly Val Asp Tyr Thr Ile Thr Val
        50                  55                  60

Tyr Ala Val Ser Asp Asp Asn Lys Tyr Tyr His Gln His Arg Pro Ile
65                  70                  75                  80

Ser Ile Asn Tyr Arg Thr
                85

<210> SEQ ID NO 133
<211> LENGTH: 86
<212> TYPE: PRT
<213> ORGANISM: Artificial Sequence
<220> FEATURE:
<223> OTHER INFORMATION: Core 16 Adnectin

<400> SEQUENCE: 133

Glu Val Val Ala Ala Thr Pro Thr Ser Leu Leu Ile Ser Trp Gly His
1               5                   10                  15

Tyr Arg Arg Ser Gly His Tyr Tyr Arg Ile Thr Tyr Gly Glu Thr Gly
            20                  25                  30

Gly Asn Ser Pro Val Gln Glu Phe Thr Val Asp Pro Ser Ser Tyr Thr
        35                  40                  45

Ala Thr Ile Ser Gly Leu Lys Pro Gly Val Asp Tyr Thr Ile Thr Val
    50                  55                  60

Tyr Ala Val Ser Lys Asp Asp Tyr Tyr Pro His Glu His Arg Pro Ile
65                  70                  75                  80

Ser Ile Asn Tyr Arg Thr
                85

<210> SEQ ID NO 134
<211> LENGTH: 86
<212> TYPE: PRT
<213> ORGANISM: Artificial Sequence
<220> FEATURE:
<223> OTHER INFORMATION: Core 17 Adnectin

<400> SEQUENCE: 134

Glu Val Val Ala Ala Thr Pro Thr Ser Leu Leu Ile Ser Trp Ser Lys
1               5                   10                  15

Tyr Ser Lys His Gly His Tyr Tyr Arg Ile Thr Tyr Gly Glu Thr Gly
            20                  25                  30

Gly Asn Ser Pro Val Gln Glu Phe Thr Val Pro Ser Gly Asn Ala Thr
        35                  40                  45

Ala Thr Ile Ser Gly Leu Lys Pro Gly Val Asp Tyr Thr Ile Thr Val
    50                  55                  60

Tyr Ala Val Glu Asp Thr Asn Asp Tyr Pro His Thr His Arg Pro Ile
65                  70                  75                  80

Ser Ile Asn Tyr Arg Thr
                85

<210> SEQ ID NO 135
<211> LENGTH: 82
<212> TYPE: PRT
<213> ORGANISM: Artificial Sequence
<220> FEATURE:
<223> OTHER INFORMATION: Core 18 Adnectin

<400> SEQUENCE: 135

Glu Val Val Ala Ala Thr Pro Thr Ser Leu Leu Ile Ser Trp Tyr Glu
1               5                   10                  15

Pro Gly Ala Ser Val Tyr Tyr Tyr Arg Ile Thr Tyr Gly Glu Thr Gly
            20                  25                  30

Gly Asn Ser Pro Val Gln Glu Phe Thr Val Pro Ser Tyr His Thr
        35                  40                  45

Ala Thr Ile Ser Gly Leu Lys Pro Gly Val Asp Tyr Thr Ile Thr Val
    50                  55                  60

Tyr Ala Val Tyr Gly Tyr Tyr Glu Tyr Glu Pro Ile Ser Ile Asn Tyr
65                  70                  75                  80

Arg Thr

```
<210> SEQ ID NO 136
<211> LENGTH: 82
<212> TYPE: PRT
<213> ORGANISM: Artificial Sequence
<220> FEATURE:
<223> OTHER INFORMATION: Core 19 Adnectin

<400> SEQUENCE: 136

Glu Val Val Ala Ala Thr Pro Thr Ser Leu Leu Ile Ser Trp Gln Ser
1               5                   10                  15

Tyr Tyr Ala His Ser Asp Tyr Tyr Arg Ile Thr Tyr Gly Glu Thr Gly
                20                  25                  30

Gly Asn Ser Pro Val Gln Glu Phe Thr Val Pro Tyr Pro Pro Gln Thr
            35                  40                  45

Ala Thr Ile Ser Gly Leu Lys Pro Gly Val Asp Tyr Thr Ile Thr Val
        50                  55                  60

Tyr Ala Val Tyr Ala Gly Ser Ser Tyr Tyr Pro Ile Ser Ile Asn Tyr
65                  70                  75                  80

Arg Thr

<210> SEQ ID NO 137
<211> LENGTH: 86
<212> TYPE: PRT
<213> ORGANISM: Artificial Sequence
<220> FEATURE:
<223> OTHER INFORMATION: Core 20 Adnectin

<400> SEQUENCE: 137

Glu Val Val Ala Ala Thr Pro Thr Ser Leu Leu Ile Ser Trp Gly His
1               5                   10                  15

Tyr Arg Arg Ser Gly His Tyr Tyr Arg Ile Thr Tyr Gly Glu Thr Gly
                20                  25                  30

Gly Asn Ser Pro Val Gln Glu Phe Thr Val Asp Pro Ser Ser Tyr Thr
            35                  40                  45

Ala Thr Ile Ser Gly Leu Lys Pro Gly Val Asp Tyr Thr Ile Thr Val
        50                  55                  60

Tyr Ala Val Ser Lys Asp Asp Tyr Tyr Pro His Glu His Arg Pro Ile
65                  70                  75                  80

Ser Ile Asn Tyr Arg Thr
                85

<210> SEQ ID NO 138
<211> LENGTH: 82
<212> TYPE: PRT
<213> ORGANISM: Artificial Sequence
<220> FEATURE:
<223> OTHER INFORMATION: Core 21 Adnectin

<400> SEQUENCE: 138

Glu Val Val Ala Ala Thr Pro Thr Ser Leu Leu Ile Ser Trp Pro Glu
1               5                   10                  15

Pro Gly Thr Pro Val Tyr Tyr Arg Ile Thr Tyr Gly Glu Thr Gly
                20                  25                  30

Gly Asn Ser Pro Val Gln Glu Phe Thr Val Pro Ala Tyr Tyr Gly Thr
            35                  40                  45

Ala Thr Ile Ser Gly Leu Lys Pro Gly Val Asp Tyr Thr Ile Thr Val
        50                  55                  60

Tyr Ala Val Tyr Gly Tyr Tyr Asp Tyr Ser Pro Ile Ser Ile Asn Tyr
65                  70                  75                  80
```

Arg Thr

<210> SEQ ID NO 139
<211> LENGTH: 86
<212> TYPE: PRT
<213> ORGANISM: Artificial Sequence
<220> FEATURE:
<223> OTHER INFORMATION: Core 22 Adnectin

<400> SEQUENCE: 139

Glu Val Val Ala Ala Thr Pro Thr Ser Leu Leu Ile Ser Trp Tyr Arg
1               5                   10                  15

Tyr Glu Lys Thr Gln His Tyr Tyr Arg Ile Thr Tyr Gly Glu Thr Gly
            20                  25                  30

Gly Asn Ser Pro Val Gln Glu Phe Thr Val Pro Pro Glu Ser Gly Thr
        35                  40                  45

Ala Thr Ile Ser Gly Leu Lys Pro Gly Val Asp Tyr Thr Ile Thr Val
    50                  55                  60

Tyr Ala Val Tyr Ala Gly Tyr Glu Tyr Pro His Thr His Arg Pro Ile
65                  70                  75                  80

Ser Ile Asn Tyr Arg Thr
                85

<210> SEQ ID NO 140
<211> LENGTH: 87
<212> TYPE: PRT
<213> ORGANISM: Artificial Sequence
<220> FEATURE:
<223> OTHER INFORMATION: Core 23 Adnectin

<400> SEQUENCE: 140

Glu Val Val Ala Ala Thr Pro Thr Ser Leu Leu Ile Ser Trp Val Lys
1               5                   10                  15

Ser Glu Glu Tyr Tyr Arg Tyr Tyr Arg Ile Thr Tyr Gly Glu Thr Gly
            20                  25                  30

Gly Asn Ser Pro Val Gln Glu Phe Thr Val Pro Tyr Tyr Val His Thr
        35                  40                  45

Ala Thr Ile Ser Gly Leu Lys Pro Gly Val Asp Tyr Thr Ile Thr Val
    50                  55                  60

Tyr Ala Val Thr Glu Tyr Tyr Ala Gly Ala Val Val Ser Val Pro
65                  70                  75                  80

Ile Ser Ile Asn Tyr Arg Thr
                85

<210> SEQ ID NO 141
<211> LENGTH: 82
<212> TYPE: PRT
<213> ORGANISM: Artificial Sequence
<220> FEATURE:
<223> OTHER INFORMATION: Core 24 Adnectin

<400> SEQUENCE: 141

Glu Val Val Ala Ala Thr Pro Thr Ser Leu Leu Ile Ser Trp Tyr Asp
1               5                   10                  15

Pro Tyr Thr Tyr Gly Ser Tyr Arg Ile Thr Tyr Gly Glu Thr Gly
            20                  25                  30

Gly Asn Ser Pro Val Gln Glu Phe Thr Val Gly Pro Tyr Thr Thr Thr
        35                  40                  45

Ala Thr Ile Ser Gly Leu Lys Pro Gly Val Asp Tyr Thr Ile Thr Val
    50                  55                  60

Tyr Ala Val Ser Tyr Tyr Ser Thr Gln Pro Ile Ser Ile Asn Tyr
65                  70                  75                  80

Arg Thr

<210> SEQ ID NO 142
<211> LENGTH: 86
<212> TYPE: PRT
<213> ORGANISM: Artificial Sequence
<220> FEATURE:
<223> OTHER INFORMATION: Core 25 Adnectin

<400> SEQUENCE: 142

Glu Val Val Ala Ala Thr Pro Thr Ser Leu Leu Ile Ser Trp Ser Asn
1               5                   10                  15

Asp Gly Pro Gly Leu Ser Tyr Tyr Arg Ile Thr Tyr Gly Glu Thr Gly
                20                  25                  30

Gly Asn Ser Pro Val Gln Glu Phe Thr Val Pro Ser Ser Gln Thr Thr
            35                  40                  45

Ala Thr Ile Ser Gly Leu Lys Pro Gly Val Asp Tyr Thr Ile Thr Val
        50                  55                  60

Tyr Ala Val Ser Tyr Tyr Thr Lys Lys Ala Tyr Ser Ala Gly Pro Ile
65                  70                  75                  80

Ser Ile Asn Tyr Arg Thr
                85

<210> SEQ ID NO 143
<211> LENGTH: 82
<212> TYPE: PRT
<213> ORGANISM: Artificial Sequence
<220> FEATURE:
<223> OTHER INFORMATION: Core 26 Adnectin

<400> SEQUENCE: 143

Glu Val Val Ala Ala Thr Pro Thr Ser Leu Leu Ile Ser Trp Pro Asp
1               5                   10                  15

Pro Tyr Tyr Lys Pro Asp Tyr Tyr Arg Ile Thr Tyr Gly Glu Thr Gly
                20                  25                  30

Gly Asn Ser Pro Val Gln Glu Phe Thr Val Pro Arg Asp Tyr Thr Thr
            35                  40                  45

Ala Thr Ile Ser Gly Leu Lys Pro Gly Val Asp Tyr Thr Ile Thr Val
        50                  55                  60

Tyr Ala Val Tyr Ser Tyr Tyr Gly Tyr Tyr Pro Ile Ser Ile Asn Tyr
65                  70                  75                  80

Arg Thr

<210> SEQ ID NO 144
<211> LENGTH: 10
<212> TYPE: PRT
<213> ORGANISM: Artificial Sequence
<220> FEATURE:
<223> OTHER INFORMATION: Exemplary Leader

<400> SEQUENCE: 144

Met Gly Val Ser Asp Val Pro Arg Asp Leu
1               5                   10

<210> SEQ ID NO 145
<211> LENGTH: 9
<212> TYPE: PRT
<213> ORGANISM: Artificial Sequence

```
<220> FEATURE:
<223> OTHER INFORMATION: Exemplary Leader

<400> SEQUENCE: 145

Gly Val Ser Asp Val Pro Arg Asp Leu
1               5

<210> SEQ ID NO 146
<211> LENGTH: 8
<212> TYPE: PRT
<213> ORGANISM: Artificial Sequence
<220> FEATURE:
<223> OTHER INFORMATION: Exemplary Leader

<400> SEQUENCE: 146

Val Ser Asp Val Pro Arg Asp Leu
1               5

<210> SEQ ID NO 147
<211> LENGTH: 7
<212> TYPE: PRT
<213> ORGANISM: Artificial Sequence
<220> FEATURE:
<223> OTHER INFORMATION: Exemplary Leader

<400> SEQUENCE: 147

Ser Asp Val Pro Arg Asp Leu
1               5

<210> SEQ ID NO 148
<211> LENGTH: 6
<212> TYPE: PRT
<213> ORGANISM: Artificial Sequence
<220> FEATURE:
<223> OTHER INFORMATION: Exemplary Leader

<400> SEQUENCE: 148

Asp Val Pro Arg Asp Leu
1               5

<210> SEQ ID NO 149
<211> LENGTH: 5
<212> TYPE: PRT
<213> ORGANISM: Artificial Sequence
<220> FEATURE:
<223> OTHER INFORMATION: Exemplary Leader

<400> SEQUENCE: 149

Val Pro Arg Asp Leu
1               5

<210> SEQ ID NO 150
<211> LENGTH: 4
<212> TYPE: PRT
<213> ORGANISM: Artificial Sequence
<220> FEATURE:
<223> OTHER INFORMATION: Exemplary Leader

<400> SEQUENCE: 150

Pro Arg Asp Leu
1

<210> SEQ ID NO 151
<211> LENGTH: 0
<212> TYPE: PRT
<213> ORGANISM: Artificial Sequence
<220> FEATURE:
```

<223> OTHER INFORMATION: Exemplary Leader Arg Asp Leu

<400> SEQUENCE: 151

000

<210> SEQ ID NO 152
<211> LENGTH: 0
<212> TYPE: PRT
<213> ORGANISM: Artificial Sequence
<220> FEATURE:
<223> OTHER INFORMATION: Exemplary Leader Asp Leu

<400> SEQUENCE: 152

000

<210> SEQ ID NO 153
<211> LENGTH: 7
<212> TYPE: PRT
<213> ORGANISM: Artificial Sequence
<220> FEATURE:
<223> OTHER INFORMATION: Exemplary Tail

<400> SEQUENCE: 153

Glu Ile Asp Lys Pro Ser Gln
1               5

<210> SEQ ID NO 154
<211> LENGTH: 6
<212> TYPE: PRT
<213> ORGANISM: Artificial Sequence
<220> FEATURE:
<223> OTHER INFORMATION: Exemplary Tail

<400> SEQUENCE: 154

Glu Ile Asp Lys Pro Ser
1               5

<210> SEQ ID NO 155
<211> LENGTH: 6
<212> TYPE: PRT
<213> ORGANISM: Artificial Sequence
<220> FEATURE:
<223> OTHER INFORMATION: Exemplary Tail

<400> SEQUENCE: 155

Glu Ile Asp Lys Pro Cys
1               5

<210> SEQ ID NO 156
<211> LENGTH: 5
<212> TYPE: PRT
<213> ORGANISM: Artificial Sequence
<220> FEATURE:
<223> OTHER INFORMATION: Exemplary Tail

<400> SEQUENCE: 156

Glu Ile Asp Lys Pro
1               5

<210> SEQ ID NO 157
<211> LENGTH: 4
<212> TYPE: PRT
<213> ORGANISM: Artificial Sequence
<220> FEATURE:
<223> OTHER INFORMATION: Exemplary Tail

<400> SEQUENCE: 157

```
Glu Ile Asp Lys
1

<210> SEQ ID NO 158
<211> LENGTH: 0
<212> TYPE: PRT
<213> ORGANISM: Artificial Sequence
<220> FEATURE:
<223> OTHER INFORMATION: Exemplary Tail Glu Ile

<400> SEQUENCE: 158

000

<210> SEQ ID NO 159
<211> LENGTH: 7
<212> TYPE: PRT
<213> ORGANISM: Artificial Sequence
<220> FEATURE:
<223> OTHER INFORMATION: Exemplary Tail

<400> SEQUENCE: 159

Glu Ile Glu Lys Pro Ser Gln
1               5

<210> SEQ ID NO 160
<211> LENGTH: 9
<212> TYPE: PRT
<213> ORGANISM: Artificial Sequence
<220> FEATURE:
<223> OTHER INFORMATION: Exemplary Tail

<400> SEQUENCE: 160

Glu Ile Asp Lys Pro Ser Gln Leu Glu
1               5

<210> SEQ ID NO 161
<211> LENGTH: 12
<212> TYPE: PRT
<213> ORGANISM: Artificial Sequence
<220> FEATURE:
<223> OTHER INFORMATION: Exemplary Tail

<400> SEQUENCE: 161

Glu Ile Glu Asp Glu Asp Glu Asp Glu Asp Glu Asp
1               5                   10

<210> SEQ ID NO 162
<211> LENGTH: 17
<212> TYPE: PRT
<213> ORGANISM: Artificial Sequence
<220> FEATURE:
<223> OTHER INFORMATION: Exemplary Tail

<400> SEQUENCE: 162

Glu Ile Glu Lys Pro Ser Gln Glu Asp Glu Asp Glu Asp Glu Asp Glu
1               5                   10                  15

Asp

<210> SEQ ID NO 163
<211> LENGTH: 5
<212> TYPE: PRT
<213> ORGANISM: Artificial Sequence
<220> FEATURE:
<223> OTHER INFORMATION: Exemplary Tail

<400> SEQUENCE: 163
```

```
Glu Gly Ser Gly Ser
1               5

<210> SEQ ID NO 164
<211> LENGTH: 5
<212> TYPE: PRT
<213> ORGANISM: Artificial Sequence
<220> FEATURE:
<223> OTHER INFORMATION: Exemplary Linkers

<400> SEQUENCE: 164

Gly Gly Ser Gly Ser
1               5

<210> SEQ ID NO 165
<211> LENGTH: 9
<212> TYPE: PRT
<213> ORGANISM: Artificial Sequence
<220> FEATURE:
<223> OTHER INFORMATION: Exemplary Linkers

<400> SEQUENCE: 165

Gly Gly Ser Gly Ser Gly Ser Gly Ser
1               5

<210> SEQ ID NO 166
<211> LENGTH: 13
<212> TYPE: PRT
<213> ORGANISM: Artificial Sequence
<220> FEATURE:
<223> OTHER INFORMATION: Exemplary Linkers

<400> SEQUENCE: 166

Gly Gly Ser Gly Ser Gly Ser Gly Ser Gly Ser Gly Ser
1               5                   10

<210> SEQ ID NO 167
<211> LENGTH: 15
<212> TYPE: PRT
<213> ORGANISM: Artificial Sequence
<220> FEATURE:
<223> OTHER INFORMATION: Exemplary Linkers

<400> SEQUENCE: 167

Gly Gly Ser Gly Ser Gly Ser Gly Ser Gly Ser Gly Ser Gly Ser
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Exemplary Linkers

<400> SEQUENCE: 168

Gly Gly Ser Gly Ser Gly Ser Gly Ser Gly Ser Gly Ser Gly Ser Gly
1               5                   10                  15

<210> SEQ ID NO 169
<211> LENGTH: 4
<212> TYPE: PRT
<213> ORGANISM: Artificial Sequence
<220> FEATURE:
<223> OTHER INFORMATION: Exemplary Linkers

<400> SEQUENCE: 169
```

Gly Ser Gly Ser
1

<210> SEQ ID NO 170
<211> LENGTH: 8
<212> TYPE: PRT
<213> ORGANISM: Artificial Sequence
<220> FEATURE:
<223> OTHER INFORMATION: Exemplary Linkers

<400> SEQUENCE: 170

Gly Ser Gly Ser Gly Ser Gly Ser
1               5

<210> SEQ ID NO 171
<211> LENGTH: 14
<212> TYPE: PRT
<213> ORGANISM: Artificial Sequence
<220> FEATURE:
<223> OTHER INFORMATION: Exemplary Linkers

<400> SEQUENCE: 171

Gly Ser Gly Ser Gly Ser Gly Ser Gly Ser Gly Ser Gly Ser
1               5                   10

<210> SEQ ID NO 172
<211> LENGTH: 13
<212> TYPE: PRT
<213> ORGANISM: Artificial Sequence
<220> FEATURE:
<223> OTHER INFORMATION: Exemplary Linkers

<400> SEQUENCE: 172

Gly Ser Ala Ala Ala Ala Ala Ala Ala Ala Ala Gly Ser
1               5                   10

<210> SEQ ID NO 173
<211> LENGTH: 15
<212> TYPE: PRT
<213> ORGANISM: Artificial Sequence
<220> FEATURE:
<223> OTHER INFORMATION: Exemplary Linkers

<400> SEQUENCE: 173

Gly Ser Glu Gly Ser Glu Gly Ser Glu Gly Ser Glu Gly Ser Glu
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Exemplary Linkers

<400> SEQUENCE: 174

Pro Ala Ser Pro Ala Ser Pro Ala Ser Pro Ala Ser Pro Ala Ser
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Exemplary Linkers

<400> SEQUENCE: 175

Gly Ser Pro Gly Ser Pro Gly Ser Pro Gly Ser Pro Gly Ser Pro

-continued

```
<210> SEQ ID NO 176
<211> LENGTH: 14
<212> TYPE: PRT
<213> ORGANISM: Artificial Sequence
<220> FEATURE:
<223> OTHER INFORMATION: Exemplary Linkers

<400> SEQUENCE: 176

Gly Ser Thr Val Ala Ala Pro Ser Thr Val Ala Ala Pro Ser
1               5                   10

<210> SEQ ID NO 177
<211> LENGTH: 8
<212> TYPE: PRT
<213> ORGANISM: Artificial Sequence
<220> FEATURE:
<223> OTHER INFORMATION: Exemplary Linkers

<400> SEQUENCE: 177

Gly Gly Ser Glu Gly Gly Ser Glu
1               5

<210> SEQ ID NO 178
<211> LENGTH: 7
<212> TYPE: PRT
<213> ORGANISM: Artificial Sequence
<220> FEATURE:
<223> OTHER INFORMATION: Exemplary Linkers

<400> SEQUENCE: 178

Ser Thr Ser Thr Ser Thr Gly
1               5

<210> SEQ ID NO 179
<211> LENGTH: 35
<212> TYPE: PRT
<213> ORGANISM: Artificial Sequence
<220> FEATURE:
<223> OTHER INFORMATION: Exemplary Linkers

<400> SEQUENCE: 179

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser
            35

<210> SEQ ID NO 180
<211> LENGTH: 30
<212> TYPE: PRT
<213> ORGANISM: Artificial Sequence
<220> FEATURE:
<223> OTHER INFORMATION: Exemplary Linkers

<400> SEQUENCE: 180

Gly Gly Gly Gly Ser Gly Gly Gly Ser Gly Gly Gly Ser Gly
1               5                   10                  15

Gly Gly Ser Gly Gly Gly Ser Gly Gly Gly Ser
                20                  25                  30

<210> SEQ ID NO 181
<211> LENGTH: 16
```

```
<212> TYPE: PRT
<213> ORGANISM: Artificial Sequence
<220> FEATURE:
<223> OTHER INFORMATION: Exemplary Linkers

<400> SEQUENCE: 181

Gly Gly Gly Gly Ser Gly Gly Gly Ser Gly Gly Gly Gly Ser Gly
1               5                   10                  15

<210> SEQ ID NO 182
<211> LENGTH: 7
<212> TYPE: PRT
<213> ORGANISM: Artificial Sequence
<220> FEATURE:
<223> OTHER INFORMATION: Exemplary Linkers

<400> SEQUENCE: 182

Gly Pro Gly Pro Gly Pro Gly
1               5

<210> SEQ ID NO 183
<211> LENGTH: 11
<212> TYPE: PRT
<213> ORGANISM: Artificial Sequence
<220> FEATURE:
<223> OTHER INFORMATION: Exemplary Linkers

<400> SEQUENCE: 183

Gly Pro Gly Pro Gly Pro Gly Pro Gly Pro Gly
1               5                   10

<210> SEQ ID NO 184
<211> LENGTH: 7
<212> TYPE: PRT
<213> ORGANISM: Artificial Sequence
<220> FEATURE:
<223> OTHER INFORMATION: Exemplary Linkers

<400> SEQUENCE: 184

Pro Ser Thr Ser Thr Ser Thr
1               5

<210> SEQ ID NO 185
<211> LENGTH: 6
<212> TYPE: PRT
<213> ORGANISM: Artificial Sequence
<220> FEATURE:
<223> OTHER INFORMATION: Exemplary Linkers

<400> SEQUENCE: 185

Pro Ala Pro Ala Pro Ala
1               5

<210> SEQ ID NO 186
<211> LENGTH: 12
<212> TYPE: PRT
<213> ORGANISM: Artificial Sequence
<220> FEATURE:
<223> OTHER INFORMATION: Exemplary Linkers

<400> SEQUENCE: 186

Pro Ala Pro Ala Pro Ala Pro Ala Pro Ala Pro Ala
1               5                   10

<210> SEQ ID NO 187
<211> LENGTH: 18
<212> TYPE: PRT
```

<213> ORGANISM: Artificial Sequence
<220> FEATURE:
<223> OTHER INFORMATION: Exemplary Linkers

<400> SEQUENCE: 187

Pro Ala Pro Ala Pro Ala Pro Ala Pro Ala Pro Ala Pro Ala Pro Ala
1               5                   10                  15

Pro Ala

<210> SEQ ID NO 188
<211> LENGTH: 105
<212> TYPE: PRT
<213> ORGANISM: Artificial Sequence
<220> FEATURE:
<223> OTHER INFORMATION: Core 1 Adnectin Exemplary Extension

<400> SEQUENCE: 188

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Asp Lys
                85                  90                  95

Pro Ser Gln His His His His His His
            100                 105

<210> SEQ ID NO 189
<211> LENGTH: 104
<212> TYPE: PRT
<213> ORGANISM: Artificial Sequence
<220> FEATURE:
<223> OTHER INFORMATION: Core 1 Adnectin Exemplary Extension

<400> SEQUENCE: 189

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp
            100

<210> SEQ ID NO 190
<211> LENGTH: 110
<212> TYPE: PRT
<213> ORGANISM: Artificial Sequence
<220> FEATURE:

-continued

<223> OTHER INFORMATION: Core 1 Adnectin Exemplary Extension

<400> SEQUENCE: 190

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp His His His His His His
                100                 105                 110

<210> SEQ ID NO 191
<211> LENGTH: 109
<212> TYPE: PRT
<213> ORGANISM: Artificial Sequence
<220> FEATURE:
<223> OTHER INFORMATION: Core 2 Adnectin Exemplary Extension

<400> SEQUENCE: 191

Met Gly Val Ser Asp Val Pro Arg Asp Leu Glu Val Val Ala Ala Thr
1               5                   10                  15

Pro Thr Ser Leu Leu Ile Ser Trp Pro Lys Tyr Asp Lys Thr Gly His
            20                  25                  30

Tyr Tyr Arg Ile Thr Tyr Gly Glu Thr Gly Gly Asn Ser Pro Val Gln
        35                  40                  45

Glu Phe Thr Val Pro Thr Arg Gln Thr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr
                85                  90                  95

Glu Ile Asp Lys Pro Ser Gln His His His His His His
                100                 105

<210> SEQ ID NO 192
<211> LENGTH: 109
<212> TYPE: PRT
<213> ORGANISM: Artificial Sequence
<220> FEATURE:
<223> OTHER INFORMATION: Core 3 Adnectin Exemplary Extension

<400> SEQUENCE: 192

Met Gly Val Ser Asp Val Pro Arg Asp Leu Glu Val Val Ala Ala Thr
1               5                   10                  15

Pro Thr Ser Leu Leu Ile Ser Trp Ser Asn Asp Gly Pro Gly Leu Ser
            20                  25                  30

Tyr Tyr Arg Ile Thr Tyr Gly Glu Thr Gly Gly Asn Ser Pro Val Gln
        35                  40                  45

Glu Phe Thr Val Pro Ser Ser Gln Thr Thr Ala Thr Ile Ser Gly Leu
    50                  55                  60

Lys Pro Gly Val Asp Tyr Thr Ile Thr Val Tyr Ala Val Ser Tyr Tyr

```
                65                  70                  75                  80
Thr Lys Lys Ala Tyr Ser Ala Gly Pro Ile Ser Ile Asn Tyr Arg Thr
                    85                  90                  95

Glu Ile Asp Lys Pro Ser Gln His His His His His His
                100                 105

<210> SEQ ID NO 193
<211> LENGTH: 109
<212> TYPE: PRT
<213> ORGANISM: Artificial Sequence
<220> FEATURE:
<223> OTHER INFORMATION: Core 4 Adnectin Exemplary Extension

<400> SEQUENCE: 193

Met Gly Val Ser Asp Val Pro Arg Asp Leu Glu Met Val Ala Ala Thr
1               5                   10                  15

Pro Thr Ser Leu Leu Ile Ser Trp Glu Asp Asp Ser Tyr Tyr Ser Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Asp Leu Tyr Thr Ala Thr Ile Ser Gly Leu
    50                  55                  60

Lys Pro Gly Val Asp Tyr Thr Ile Thr Val Tyr Ala Val Thr Tyr Asp
65                  70                  75                  80

Val Thr Asp Leu Ile Met His Glu Pro Ile Ser Ile Asn Tyr Arg Thr
                85                  90                  95

Glu Ile Asp Lys Pro Ser Gln His His His His His His
                100                 105

<210> SEQ ID NO 194
<211> LENGTH: 109
<212> TYPE: PRT
<213> ORGANISM: Artificial Sequence
<220> FEATURE:
<223> OTHER INFORMATION: Core 5 Adnectin Exemplary Extension

<400> SEQUENCE: 194

Met Gly Val Ser Asp Val Pro Arg Asp Leu Glu Val Val Ala Ala Thr
1               5                   10                  15

Pro Thr Ser Leu Leu Ile Ser Trp Glu Asp Asp Ser Tyr Tyr Ser Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Asp Leu Tyr Thr Ala Thr Ile Ser Gly Leu
    50                  55                  60

Lys Pro Gly Val Asp Tyr Thr Ile Thr Val Tyr Ala Val Thr Tyr Asp
65                  70                  75                  80

Val Thr Asp Leu Ile Met His Glu Pro Ile Ser Ile Asn Tyr Arg Thr
                85                  90                  95

Glu Ile Asp Lys Pro Ser Gln His His His His His His
                100                 105

<210> SEQ ID NO 195
<211> LENGTH: 109
<212> TYPE: PRT
<213> ORGANISM: Artificial Sequence
<220> FEATURE:
<223> OTHER INFORMATION: Core 6 Adnectin Exemplary Extension

<400> SEQUENCE: 195
```

Met Gly Val Ser Asp Val Pro Arg Asp Leu Glu Val Val Ala Ala Thr
1               5                   10                  15

Pro Thr Ser Leu Leu Ile Ser Trp Tyr Met Asp Glu Tyr Asp Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Asn Tyr Tyr Asn Thr Ala Thr Ile Ser Gly Leu
    50                  55                  60

Lys Pro Gly Val Asp Tyr Thr Ile Thr Val Tyr Ala Val Thr Arg Ile
65                  70                  75                  80

Lys Ala Asn Asn Tyr Met Tyr Gly Pro Ile Ser Ile Asn Tyr Arg Thr
                85                  90                  95

Glu Ile Asp Lys Pro Ser Gln His His His His His His
            100                 105

<210> SEQ ID NO 196
<211> LENGTH: 109
<212> TYPE: PRT
<213> ORGANISM: Artificial Sequence
<220> FEATURE:
<223> OTHER INFORMATION: Core 7 Adnectin Exemplary Extension

<400> SEQUENCE: 196

Met Gly Val Ser Asp Val Pro Arg Asp Leu Glu Val Val Ala Ala Thr
1               5                   10                  15

Pro Thr Ser Leu Leu Ile Ser Trp Asn His Leu Glu His Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Glu Tyr Pro Thr Thr Ala Thr Ile Ser Gly Leu
    50                  55                  60

Lys Pro Gly Val Asp Tyr Thr Ile Thr Val Tyr Ala Val Thr Ile Thr
65                  70                  75                  80

Met Leu Lys Tyr Pro Thr Gln Ser Pro Ile Ser Ile Asn Tyr Arg Thr
                85                  90                  95

Glu Ile Asp Lys Pro Ser Gln His His His His His His
            100                 105

<210> SEQ ID NO 197
<211> LENGTH: 109
<212> TYPE: PRT
<213> ORGANISM: Artificial Sequence
<220> FEATURE:
<223> OTHER INFORMATION: Core 8 Adnectin Exemplary Extension

<400> SEQUENCE: 197

Met Gly Val Ser Asp Val Pro Arg Asp Leu Glu Val Val Ala Ala Thr
1               5                   10                  15

Pro Thr Ser Leu Leu Ile Ser Trp Gly His Tyr Arg Arg Ser Gly His
            20                  25                  30

Tyr Tyr Arg Ile Thr Tyr Gly Glu Thr Gly Gly Asn Ser Pro Val Gln
        35                  40                  45

Glu Phe Thr Val Asp Pro Ser Ser Tyr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr

```
                85                  90                  95

Glu Ile Asp Lys Pro Ser Gln His His His His His
            100                 105

<210> SEQ ID NO 198
<211> LENGTH: 107
<212> TYPE: PRT
<213> ORGANISM: Artificial Sequence
<220> FEATURE:
<223> OTHER INFORMATION: Core 9 Adnectin Exemplary Extension

<400> SEQUENCE: 198

Met Gly Val Ser Asp Val Pro Arg Asp Leu Glu Val Val Ala Ala Thr
1               5                   10                  15

Pro Thr Ser Leu Leu Ile Ser Trp Asp Ala Ser His Tyr Glu Arg Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Tyr His His Thr Ala Thr Ile Ser Gly Leu
    50                  55                  60

Lys Pro Gly Val Asp Tyr Thr Ile Thr Val Tyr Ala Val Thr Gln Ala
65                  70                  75                  80

Gln Glu His Tyr Gln Pro Pro Ile Ser Ile Asn Tyr Arg Thr Glu Ile
                85                  90                  95

Asp Lys Pro Ser Gln His His His His His
            100                 105

<210> SEQ ID NO 199
<211> LENGTH: 105
<212> TYPE: PRT
<213> ORGANISM: Artificial Sequence
<220> FEATURE:
<223> OTHER INFORMATION: Core 10 Adnectin Exemplary Extension

<400> SEQUENCE: 199

Met Gly Val Ser Asp Val Pro Arg Asp Leu Glu Val Val Ala Ala Thr
1               5                   10                  15

Pro Thr Ser Leu Leu Ile Ser Trp Asn Ser Tyr Tyr His Ser Ala Asp
            20                  25                  30

Tyr Tyr Arg Ile Thr Tyr Gly Glu Thr Gly Gly Asn Ser Pro Val Gln
        35                  40                  45

Glu Phe Thr Val Pro Tyr Pro Pro Thr Thr Ala Thr Ile Ser Gly Leu
    50                  55                  60

Lys Pro Gly Val Asp Tyr Thr Ile Thr Val Tyr Ala Val Tyr Ser Ala
65                  70                  75                  80

Lys Ser Tyr Tyr Pro Ile Ser Ile Asn Tyr Arg Thr Glu Ile Asp Lys
                85                  90                  95

Pro Ser Gln His His His His His His
            100                 105

<210> SEQ ID NO 200
<211> LENGTH: 109
<212> TYPE: PRT
<213> ORGANISM: Artificial Sequence
<220> FEATURE:
<223> OTHER INFORMATION: Core 11 Adnectin Exemplary Extension

<400> SEQUENCE: 200

Met Gly Val Ser Asp Val Pro Arg Asp Leu Glu Val Val Ala Ala Thr
1               5                   10                  15
```

-continued

Pro Thr Ser Leu Leu Ile Ser Trp Ser Lys Tyr Ser Lys His Gly His
            20                  25                  30

Tyr Tyr Arg Ile Thr Tyr Gly Glu Thr Gly Gly Asn Ser Pro Val Gln
        35                  40                  45

Glu Phe Thr Val Pro Ser Gly Asn Ala Thr Ala Thr Ile Ser Gly Leu
 50                  55                  60

Lys Pro Gly Val Asp Tyr Thr Ile Thr Val Tyr Ala Val Glu Asp Thr
65                  70                  75                  80

Asn Asp Tyr Pro His Thr His Arg Pro Ile Ser Ile Asn Tyr Arg Thr
                85                  90                  95

Glu Ile Asp Lys Pro Ser Gln His His His His His His
            100                 105

<210> SEQ ID NO 201
<211> LENGTH: 107
<212> TYPE: PRT
<213> ORGANISM: Artificial Sequence
<220> FEATURE:
<223> OTHER INFORMATION: Core 12 Adnectin Exemplary Extension

<400> SEQUENCE: 201

Met Gly Val Ser Asp Val Pro Arg Asp Leu Glu Val Val Ala Ala Thr
 1               5                  10                  15

Pro Thr Ser Leu Leu Ile Ser Trp His Gly Glu Pro Asp Gln Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Pro Tyr Arg Arg Thr Ala Thr Ile Ser Gly Leu
 50                  55                  60

Lys Pro Gly Val Asp Tyr Thr Ile Thr Val Tyr Ala Val Thr Ser Gly
65                  70                  75                  80

Tyr Thr Gly His Tyr Gln Pro Ile Ser Ile Asn Tyr Arg Thr Glu Ile
                85                  90                  95

Asp Lys Pro Ser Gln His His His His His
            100                 105

<210> SEQ ID NO 202
<211> LENGTH: 109
<212> TYPE: PRT
<213> ORGANISM: Artificial Sequence
<220> FEATURE:
<223> OTHER INFORMATION: Core 13 Adnectin Exemplary Extension

<400> SEQUENCE: 202

Met Gly Val Ser Asp Val Pro Arg Asp Leu Glu Val Val Ala Ala Thr
 1               5                  10                  15

Pro Thr Ser Leu Leu Ile Ser Trp Ser Lys Tyr Ser Lys His Gly His
            20                  25                  30

Tyr Tyr Arg Ile Thr Tyr Gly Glu Thr Gly Gly Asn Ser Pro Val Gln
        35                  40                  45

Glu Phe Thr Val Asp Pro Ser Ser Tyr Thr Ala Thr Ile Ser Gly Leu
 50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr
                85                  90                  95

Glu Ile Asp Lys Pro Ser Gln His His His His His His

<210> SEQ ID NO 203
<211> LENGTH: 105
<212> TYPE: PRT
<213> ORGANISM: Artificial Sequence
<220> FEATURE:
<223> OTHER INFORMATION: Core 14 Adnectin Exemplary Extension

<400> SEQUENCE: 203

Met Gly Val Ser Asp Val Pro Arg Asp Leu Glu Val Val Ala Ala Thr
1               5                   10                  15

Pro Thr Ser Leu Leu Ile Ser Trp Tyr Glu Pro Tyr Thr Pro Ile His
            20                  25                  30

Tyr Tyr Arg Ile Thr Tyr Gly Glu Thr Gly Gly Asn Ser Pro Val Gln
        35                  40                  45

Glu Phe Thr Val Pro Gly Tyr Tyr Gly Thr Ala Thr Ile Ser Gly Leu
    50                  55                  60

Lys Pro Gly Val Asp Tyr Thr Ile Thr Val Tyr Ala Val Tyr Gly Tyr
65                  70                  75                  80

Tyr Gln Tyr Thr Pro Ile Ser Ile Asn Tyr Arg Thr Glu Ile Asp Lys
                85                  90                  95

Pro Ser Gln His His His His His His
            100                 105

<210> SEQ ID NO 204
<211> LENGTH: 109
<212> TYPE: PRT
<213> ORGANISM: Artificial Sequence
<220> FEATURE:
<223> OTHER INFORMATION: Core 15 Adnectin Exemplary Extension

<400> SEQUENCE: 204

Met Gly Val Ser Asp Val Pro Arg Asp Leu Glu Val Val Ala Ala Thr
1               5                   10                  15

Pro Thr Ser Leu Leu Ile Ser Trp Ser Lys Tyr Ser Lys His Gly His
            20                  25                  30

Tyr Tyr Arg Ile Thr Tyr Gly Glu Thr Gly Gly Asn Ser Pro Val Gln
        35                  40                  45

Glu Phe Thr Val Pro Ser Gly Asn Ala Thr Ala Thr Ile Ser Gly Leu
    50                  55                  60

Lys Pro Gly Val Asp Tyr Thr Ile Thr Val Tyr Ala Val Ser Asp Asp
65                  70                  75                  80

Asn Lys Tyr Tyr His Gln His Arg Pro Ile Ser Ile Asn Tyr Arg Thr
                85                  90                  95

Glu Ile Asp Lys Pro Ser Gln His His His His His His
            100                 105

<210> SEQ ID NO 205
<211> LENGTH: 109
<212> TYPE: PRT
<213> ORGANISM: Artificial Sequence
<220> FEATURE:
<223> OTHER INFORMATION: Core 16 Adnectin Exemplary Extension

<400> SEQUENCE: 205

Met Gly Val Ser Asp Val Pro Arg Asp Leu Glu Val Val Ala Ala Thr
1               5                   10                  15

Pro Thr Ser Leu Leu Ile Ser Trp Gly His Tyr Arg Arg Ser Gly His
            20                  25                  30

Tyr Tyr Arg Ile Thr Tyr Gly Glu Thr Gly Gly Asn Ser Pro Val Gln
            35                  40                  45

Glu Phe Thr Val Asp Pro Ser Ser Tyr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr
                85                  90                  95

Glu Ile Asp Lys Pro Ser Gln His His His His His His
            100                 105

<210> SEQ ID NO 206
<211> LENGTH: 109
<212> TYPE: PRT
<213> ORGANISM: Artificial Sequence
<220> FEATURE:
<223> OTHER INFORMATION: Core 17 Adnectin Exemplary Extension

<400> SEQUENCE: 206

Met Gly Val Ser Asp Val Pro Arg Asp Leu Glu Val Val Ala Ala Thr
1               5                   10                  15

Pro Thr Ser Leu Leu Ile Ser Trp Ser Lys Tyr Ser Lys His Gly His
            20                  25                  30

Tyr Tyr Arg Ile Thr Tyr Gly Glu Thr Gly Gly Asn Ser Pro Val Gln
            35                  40                  45

Glu Phe Thr Val Pro Ser Gly Asn Ala Thr Ala Thr Ile Ser Gly Leu
    50                  55                  60

Lys Pro Gly Val Asp Tyr Thr Ile Thr Val Tyr Ala Val Glu Asp Thr
65                  70                  75                  80

Asn Asp Tyr Pro His Thr His Arg Pro Ile Ser Ile Asn Tyr Arg Thr
                85                  90                  95

Glu Ile Asp Lys Pro Ser Gln His His His His His His
            100                 105

<210> SEQ ID NO 207
<211> LENGTH: 105
<212> TYPE: PRT
<213> ORGANISM: Artificial Sequence
<220> FEATURE:
<223> OTHER INFORMATION: Core 18 Adnectin Exemplary Extension

<400> SEQUENCE: 207

Met Gly Val Ser Asp Val Pro Arg Asp Leu Glu Val Val Ala Ala Thr
1               5                   10                  15

Pro Thr Ser Leu Leu Ile Ser Trp Tyr Glu Pro Gly Ala Ser Val Tyr
            20                  25                  30

Tyr Tyr Arg Ile Thr Tyr Gly Glu Thr Gly Gly Asn Ser Pro Val Gln
            35                  40                  45

Glu Phe Thr Val Pro Ser Tyr Tyr His Thr Ala Thr Ile Ser Gly Leu
    50                  55                  60

Lys Pro Gly Val Asp Tyr Thr Ile Thr Val Tyr Ala Val Tyr Gly Tyr
65                  70                  75                  80

Tyr Glu Tyr Glu Pro Ile Ser Ile Asn Tyr Arg Thr Glu Ile Asp Lys
                85                  90                  95

Pro Ser Gln His His His His His His
            100                 105

```
<210> SEQ ID NO 208
<211> LENGTH: 105
<212> TYPE: PRT
<213> ORGANISM: Artificial Sequence
<220> FEATURE:
<223> OTHER INFORMATION: Core 19 Adnectin Exemplary Extension

<400> SEQUENCE: 208
```

Met Gly Val Ser Asp Val Pro Arg Asp Leu Glu Val Val Ala Ala Thr
1               5                   10                  15

Pro Thr Ser Leu Leu Ile Ser Trp Gln Ser Tyr Ala His Ser Asp
            20                  25                  30

Tyr Tyr Arg Ile Thr Tyr Gly Glu Thr Gly Gly Asn Ser Pro Val Gln
        35                  40                  45

Glu Phe Thr Val Pro Tyr Pro Pro Gln Thr Ala Thr Ile Ser Gly Leu
    50                  55                  60

Lys Pro Gly Val Asp Tyr Thr Ile Thr Val Tyr Ala Val Tyr Ala Gly
65                  70                  75                  80

Ser Ser Tyr Tyr Pro Ile Ser Ile Asn Tyr Arg Thr Glu Ile Asp Lys
                85                  90                  95

Pro Ser Gln His His His His His His
            100                 105

```
<210> SEQ ID NO 209
<211> LENGTH: 109
<212> TYPE: PRT
<213> ORGANISM: Artificial Sequence
<220> FEATURE:
<223> OTHER INFORMATION: Core 20 Adnectin Exemplary Extension

<400> SEQUENCE: 209
```

Met Gly Val Ser Asp Val Pro Arg Asp Leu Glu Val Val Ala Ala Thr
1               5                   10                  15

Pro Thr Ser Leu Leu Ile Ser Trp Gly His Tyr Arg Arg Ser Gly His
            20                  25                  30

Tyr Tyr Arg Ile Thr Tyr Gly Glu Thr Gly Gly Asn Ser Pro Val Gln
        35                  40                  45

Glu Phe Thr Val Asp Pro Ser Ser Tyr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr
                85                  90                  95

Glu Ile Asp Lys Pro Ser Gln His His His His His
            100                 105

```
<210> SEQ ID NO 210
<211> LENGTH: 105
<212> TYPE: PRT
<213> ORGANISM: Artificial Sequence
<220> FEATURE:
<223> OTHER INFORMATION: Core 21 Adnectin Exemplary Extension

<400> SEQUENCE: 210
```

Met Gly Val Ser Asp Val Pro Arg Asp Leu Glu Val Val Ala Ala Thr
1               5                   10                  15

Pro Thr Ser Leu Leu Ile Ser Trp Pro Glu Pro Gly Thr Pro Val Tyr
            20                  25                  30

Tyr Tyr Arg Ile Thr Tyr Gly Glu Thr Gly Gly Asn Ser Pro Val Gln
        35                  40                  45

-continued

Glu Phe Thr Val Pro Ala Tyr Gly Thr Thr Ile Ser Gly Leu
                50                  55                  60

Lys Pro Gly Val Asp Tyr Thr Ile Thr Val Tyr Ala Val Gly Tyr
 65                  70                  75                  80

Tyr Asp Tyr Ser Pro Ile Ser Ile Asn Tyr Arg Thr Glu Ile Asp Lys
                 85                  90                  95

Pro Ser Gln His His His His His His
            100                 105

<210> SEQ ID NO 211
<211> LENGTH: 109
<212> TYPE: PRT
<213> ORGANISM: Artificial Sequence
<220> FEATURE:
<223> OTHER INFORMATION: Core 22 Adnectin Exemplary Extension

<400> SEQUENCE: 211

Met Gly Val Ser Asp Val Pro Arg Asp Leu Glu Val Val Ala Ala Thr
  1               5                  10                  15

Pro Thr Ser Leu Leu Ile Ser Trp Tyr Arg Tyr Glu Lys Thr Gln His
                20                  25                  30

Tyr Tyr Arg Ile Thr Tyr Gly Glu Thr Gly Gly Asn Ser Pro Val Gln
                35                  40                  45

Glu Phe Thr Val Pro Pro Glu Ser Gly Thr Ala Thr Ile Ser Gly Leu
                50                  55                  60

Lys Pro Gly Val Asp Tyr Thr Ile Thr Val Tyr Ala Val Tyr Ala Gly
 65                  70                  75                  80

Tyr Glu Tyr Pro His Thr His Arg Pro Ile Ser Ile Asn Tyr Arg Thr
                 85                  90                  95

Glu Ile Asp Lys Pro Ser Gln His His His His His
            100                 105

<210> SEQ ID NO 212
<211> LENGTH: 110
<212> TYPE: PRT
<213> ORGANISM: Artificial Sequence
<220> FEATURE:
<223> OTHER INFORMATION: Core 23 Adnectin Exemplary Extension

<400> SEQUENCE: 212

Met Gly Val Ser Asp Val Pro Arg Asp Leu Glu Val Val Ala Ala Thr
  1               5                  10                  15

Pro Thr Ser Leu Leu Ile Ser Trp Val Lys Ser Glu Gly Tyr Tyr Arg
                20                  25                  30

Tyr Tyr Arg Ile Thr Tyr Gly Glu Thr Gly Gly Asn Ser Pro Val Gln
                35                  40                  45

Glu Phe Thr Val Pro Tyr Tyr Val His Thr Ala Thr Ile Ser Gly Leu
                50                  55                  60

Lys Pro Gly Val Asp Tyr Thr Ile Thr Val Tyr Ala Val Thr Glu Tyr
 65                  70                  75                  80

Tyr Tyr Ala Gly Ala Val Val Ser Val Pro Ile Ser Ile Asn Tyr Arg
                 85                  90                  95

Thr Glu Ile Asp Lys Pro Ser Gln His His His His His
            100                 105                 110

<210> SEQ ID NO 213
<211> LENGTH: 105
<212> TYPE: PRT

<213> ORGANISM: Artificial Sequence
<220> FEATURE:
<223> OTHER INFORMATION: Core 24 Adnectin Exemplary Extension

<400> SEQUENCE: 213

Met Gly Val Ser Asp Val Pro Arg Asp Leu Glu Val Val Ala Ala Thr
1               5                   10                  15

Pro Thr Ser Leu Leu Ile Ser Trp Tyr Asp Pro Tyr Thr Tyr Gly Ser
            20                  25                  30

Tyr Tyr Arg Ile Thr Tyr Gly Glu Thr Gly Gly Asn Ser Pro Val Gln
        35                  40                  45

Glu Phe Thr Val Gly Pro Tyr Thr Thr Ala Thr Ile Ser Gly Leu
50                  55                  60

Lys Pro Gly Val Asp Tyr Thr Ile Thr Val Tyr Ala Val Ser Tyr Tyr
65                  70                  75                  80

Tyr Ser Thr Gln Pro Ile Ser Ile Asn Tyr Arg Thr Glu Ile Asp Lys
                85                  90                  95

Pro Ser Gln His His His His His
            100                 105

<210> SEQ ID NO 214
<211> LENGTH: 109
<212> TYPE: PRT
<213> ORGANISM: Artificial Sequence
<220> FEATURE:
<223> OTHER INFORMATION: Core 25 Adnectin Exemplary Extension

<400> SEQUENCE: 214

Met Gly Val Ser Asp Val Pro Arg Asp Leu Glu Val Val Ala Ala Thr
1               5                   10                  15

Pro Thr Ser Leu Leu Ile Ser Trp Ser Asn Asp Gly Pro Gly Leu Ser
            20                  25                  30

Tyr Tyr Arg Ile Thr Tyr Gly Glu Thr Gly Gly Asn Ser Pro Val Gln
        35                  40                  45

Glu Phe Thr Val Pro Ser Ser Gln Thr Thr Ala Thr Ile Ser Gly Leu
50                  55                  60

Lys Pro Gly Val Asp Tyr Thr Ile Thr Val Tyr Ala Val Ser Tyr Tyr
65                  70                  75                  80

Thr Lys Lys Ala Tyr Ser Ala Gly Pro Ile Ser Ile Asn Tyr Arg Thr
                85                  90                  95

Glu Ile Asp Lys Pro Ser Gln His His His His His
            100                 105

<210> SEQ ID NO 215
<211> LENGTH: 105
<212> TYPE: PRT
<213> ORGANISM: Artificial Sequence
<220> FEATURE:
<223> OTHER INFORMATION: Core 26 Adnectin Exemplary Extension

<400> SEQUENCE: 215

Met Gly Val Ser Asp Val Pro Arg Asp Leu Glu Val Val Ala Ala Thr
1               5                   10                  15

Pro Thr Ser Leu Leu Ile Ser Trp Pro Asp Pro Tyr Tyr Lys Pro Asp
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Tyr Thr Thr Ala Thr Ile Ser Gly Leu
50                  55                  60

```
Lys Pro Gly Val Asp Tyr Thr Ile Thr Val Tyr Ala Val Tyr Ser Tyr
 65                  70                  75                  80

Tyr Gly Tyr Tyr Pro Ile Ser Ile Asn Tyr Arg Thr Glu Ile Asp Lys
                 85                  90                  95

Pro Ser Gln His His His His His
            100             105

<210> SEQ ID NO 216
<211> LENGTH: 330
<212> TYPE: DNA
<213> ORGANISM: Artificial Sequence
<220> FEATURE:
<223> OTHER INFORMATION: Clone ID 1434A08

<400> SEQUENCE: 216
atgggagttt ctgatgtgcc gcgcgacctg gaagtggttg ctgccacccc caccagcctg      60
ctgatcagct ggggtcatta cccgatgcat gttcgatatt accgcatcac ttacggcgaa     120
acaggaggca atagccctgt ccaggagttc actgtgcctc atcgtactca tacagctacc     180
atcagcggcc ttaaacctgg cgttgattat accatcactg tgtatgctgt cacttactac     240
aacgaagctg actactctca gatcccaatt tccattaatt accgcacaga aattgacaaa     300
ccatcccagc accatcacca ccaccactga                                      330

<210> SEQ ID NO 217
<211> LENGTH: 330
<212> TYPE: DNA
<213> ORGANISM: Artificial Sequence
<220> FEATURE:
<223> OTHER INFORMATION: Clone ID 1437G04

<400> SEQUENCE: 217
atgggagttt ctgatgtgcc gcgcgacctg gaagtggttg ctgccacccc caccagcctg      60
ctgatcagct ggggtcatta cccgctgcat gttcgatatt accgcatcac ttacggcgaa     120
acaggaggca atagccctgt ccaggagttc actgtgcctt actaccatta cacagctacc     180
atcagcggcc ttaaacctgg cgttgattat accatcactg tgtatgctgt cacttactac     240
aacgaagctg actactctca gatcccaatt tccattaatt accgcacaga aattgacaaa     300
ccatcccagc accatcacca ccaccactga                                      330

<210> SEQ ID NO 218
<211> LENGTH: 330
<212> TYPE: DNA
<213> ORGANISM: Artificial Sequence
<220> FEATURE:
<223> OTHER INFORMATION: Clone ID 1437A09

<400> SEQUENCE: 218
atgggagttt ctgatgtgcc gcgcgacctg gaagtggttg ctgccacccc caccagcctg      60
ctgatcagct ggggtcatta cccgatgcat gttcgatatt accgcatcac ttacggcgaa     120
acaggaggca atagccctgt ccaggagttc actgtgcctt ctaaacagca tacagctacc     180
atcagcggcc ttaaacctgg cgttgattat accatcactg tgtatgctgt cacttactac     240
aacgaagctg actactctca gatcccaatt tccattaatt accgcacaga aattgacaaa     300
ccatcccagc accatcacca ccaccactga                                      330

<210> SEQ ID NO 219
<211> LENGTH: 330
```

```
<212> TYPE: DNA
<213> ORGANISM: Artificial Sequence
<220> FEATURE:
<223> OTHER INFORMATION: Clone ID 1438E05

<400> SEQUENCE: 219
atgggagttt ctgatgtgcc gcgcgacctg aagtggttg ctgccacccc caccagcctg      60
ctgatcagct ggggtcatta cccgatgcat gttcgatatt accgcatcac ttacggcgaa    120
acaggaggca atagccctgt ccaggagttc actgtgcctt ctaacgttca tacagctacc    180
atcagcggcc ttaaacctgg cgttgattat accatcactg tgtatgctgt cacttactac    240
aacgaagctg actactctca gatcccaatt tccattaatt accgcacaga aattgacaaa    300
ccatcccagc accatcacca ccaccactga                                      330

<210> SEQ ID NO 220
<211> LENGTH: 330
<212> TYPE: DNA
<213> ORGANISM: Artificial Sequence
<220> FEATURE:
<223> OTHER INFORMATION: Clone ID 1438D01

<400> SEQUENCE: 220
atgggagttt ctgatgtgcc gcgcgacctg aagtggttg ctgccacccc caccagcctg      60
ctgatcagct ggggtcatta cccgatgcat gttcgatatt accgcatcac ttacggcgaa    120
acaggaggca atagccctgt ccaggagttc actgtgccta accgtgctca tacagctacc    180
atcagcggcc ttaaacctgg cgttgattat accatcactg tgtatgctgt cacttactac    240
aacgaagctg actactctca gatcccaatt tccattaatt accgcacaga aattgacaaa    300
ccatcccagc accatcacca ccaccactga                                      330

<210> SEQ ID NO 221
<211> LENGTH: 330
<212> TYPE: DNA
<213> ORGANISM: Artificial Sequence
<220> FEATURE:
<223> OTHER INFORMATION: Clone ID 1438B02

<400> SEQUENCE: 221
atgggagttt ctgatgtgcc gcgcgacctg aagtggttg ctgccacccc caccagcctg      60
ctgatcagct ggggtcatta cccgatgcat gttcgatatt accgcatcac ttacggcgaa    120
acaggaggca atagccctgt ccaggagttc actgtgcctc gtaaaactta cacagctacc    180
atcagcggcc ttaaacctgg cgttgattat accatcactg tgtatgctgt cacttactac    240
aacgaagctg actactctca gatcccaatt tccattaatt accgcacaga aattgacaaa    300
ccatcccagc accatcacca ccaccactga                                      330

<210> SEQ ID NO 222
<211> LENGTH: 330
<212> TYPE: DNA
<213> ORGANISM: Artificial Sequence
<220> FEATURE:
<223> OTHER INFORMATION: Clone ID 1438A09

<400> SEQUENCE: 222
atgggagttt ctgatgtgcc gcgcgacctg aagtggttg ctgccacccc caccagcctg      60
ctgatcagct ggggtcatta cccgatgcat gttcgatatt accgcatcac ttacggcgaa    120
acaggaggca atagccctgt ccaggagttc actgtgccta ctaaacagca tacagctacc    180
```
atcagcggcc ttaaacctgg cgttgattat accatcactg tgtatgctgt cacttactac        240
aacgaagctg actactctca gatcccaatt tccattaatt accgcacaga aattgacaaa        300
ccatcccagc accatcacca ccaccactga        330

<210> SEQ ID NO 223
<211> LENGTH: 330
<212> TYPE: DNA
<213> ORGANISM: Artificial Sequence
<220> FEATURE:
<223> OTHER INFORMATION: Clone ID 1486G03

<400> SEQUENCE: 223
atgggagttt ctgatgtgcc gcgcgacctg gaagtggttg ctgccacccc caccagcctg         60
ctgatcagct ggggtcatta cccgatgcat gttcgatatt accgcatcac ttacggcgaa        120
acaggaggca atagccctgt ccaggagttc actgtgcctt ctcgttacta cacagctacc        180
atcagcggcc ttaaacctgg cgttgattat accatcactg tgtatgctgt cacttactac        240
aacgaagctg actactctca gatcccaatt tccattaatt accgcacaga aattgacaaa        300
ccatcccagc accatcacca ccaccactga        330

<210> SEQ ID NO 224
<211> LENGTH: 330
<212> TYPE: DNA
<213> ORGANISM: Artificial Sequence
<220> FEATURE:
<223> OTHER INFORMATION: Clone ID 1486C04

<400> SEQUENCE: 224
atgggagttt ctgatgtgcc gcgcgacctg gaagtggttg ctgccacccc caccagcctg         60
ctgatcagct ggggtcatta cccgatgcat gttcgatatt accgcatcac ttacggcgaa        120
acaggaggca atagccctgt ccaggagttc actgtgcctc cgcatcgtta cacagctacc        180
atcagcggcc ttaaacctgg cgttgattat accatcactg tgtatgctgt cacttactac        240
aacgaagctg actactctca gatcccaatt tccattaatt accgcacaga aattgacaaa        300
ccatcccagc accatcacca ccaccactga        330

<210> SEQ ID NO 225
<211> LENGTH: 330
<212> TYPE: DNA
<213> ORGANISM: Artificial Sequence
<220> FEATURE:
<223> OTHER INFORMATION: Clone ID 1486D04

<400> SEQUENCE: 225
atgggagttt ctgatgtgcc gcgcgacctg gaagtggttg ctgccacccc caccagcctg         60
ctgatcagct ggggtcatta cccgctgcat atccgatatt accgcatcac ttacggcgaa        120
acaggaggca atagccctgt ccaggagttc actgtgcctc gttctactca tacagctacc        180
atcagcggcc ttaaacctgg cgttgattat accatcactg tgtatgctgt cacttactac        240
aacgaagctg actactctca gatcccaatt tccattaatt accgcacaga aattgacaaa        300
ccatcccagc accatcacca ccaccactga        330

<210> SEQ ID NO 226
<211> LENGTH: 330
<212> TYPE: DNA
<213> ORGANISM: Artificial Sequence
<220> FEATURE:
<223> OTHER INFORMATION: Clone ID 1486B05

<400> SEQUENCE: 226

```
atgggagttt ctgatgtgcc gcgcgacctg gaagtggttg ctgccacccc caccagcctg    60
ctgatcagct ggggtcatta cccgatgcat gttcgatatt accgcatcac ttacggcgaa   120
acaggaggca atagccctgt ccaggagttc actgtgcctt ctcgtatcta cacagctacc   180
atcagcggcc ttaaacctgg cgttgattat accatcactg tgtatgctgt cacttactac   240
aacgaagctg actactctca gatcccaatt tccattaatt accgcacaga aattgacaaa   300
ccatcccagc accatcacca ccaccactga                                    330
```

<210> SEQ ID NO 227
<211> LENGTH: 330
<212> TYPE: DNA
<213> ORGANISM: Artificial Sequence
<220> FEATURE:
<223> OTHER INFORMATION: Clone ID 1486D05

<400> SEQUENCE: 227

```
atgggagttt ctgatgtgcc gcgcgacctg gaagtggttg ctgccacccc caccagcctg    60
ctgatcagct ggggtcatta cccgctgcat gttcgatatt accgcatcac ttacggcgaa   120
acaggaggca atagccctgt ccaggagttc actgtgcctc atcagcgtta cacagctacc   180
atcagcggcc ttaaacctgg cgttgattat accatcactg tgtatgctgt cacttactac   240
aacgaagctg actactctca gatcccaatt tccattaatt accgcacaga aattgacaaa   300
ccatcccagc accatcacca ccaccactga                                    330
```

<210> SEQ ID NO 228
<211> LENGTH: 330
<212> TYPE: DNA
<213> ORGANISM: Artificial Sequence
<220> FEATURE:
<223> OTHER INFORMATION: Clone ID 1487C03

<400> SEQUENCE: 228

```
atgggagttt ctgatgtgcc gcgcgacctg gaagtggttg ctgccacccc caccagcctg    60
ctgatcagct ggggtcatta cccgctgcat atccgatatt accgcatcac ttacggcgaa   120
acaggaggca atagccctgt ccaggagttc actgtgccta acaggttta cacagctacc    180
atcagcggcc ttaaacctgg cgttgattat accatcactg tgtatgctgt cacttactac   240
aacgaagctg actactctca gatcccaatt tccattaatt accgcacaga aattgacaaa   300
ccatcccagc accatcacca ccaccactga                                    330
```

<210> SEQ ID NO 229
<211> LENGTH: 330
<212> TYPE: DNA
<213> ORGANISM: Artificial Sequence
<220> FEATURE:
<223> OTHER INFORMATION: Clone ID 1487G03

<400> SEQUENCE: 229

```
atgggagttt ctgatgtgcc gcgcgacctg gaagtggttg ctgccacccc caccagcctg    60
ctgatcagct ggggtcatta cccgctgcat gttcgatatt accgcatcac ttacggcgaa   120
acaggaggca atagccctgt ccaggagttc actgtgcctg ctcatcgtta cacagctacc   180
atcagcggcc ttaaacctgg cgttgattat accatcactg tgtatgctgt cacttactac   240
aacgaagctg actactctca gatcccaatt tccattaatt accgcacaga aattgacaaa   300
```

```
ccatcccagc accatcacca ccaccactga                                      330
```

<210> SEQ ID NO 230
<211> LENGTH: 330
<212> TYPE: DNA
<213> ORGANISM: Artificial Sequence
<220> FEATURE:
<223> OTHER INFORMATION: Clone ID 1487D09

<400> SEQUENCE: 230

```
atgggagttt ctgatgtgcc gcgcgacctg gaagtggttg ctgccacccc caccagcctg    60
ctgatcagct ggggtcatta cccgatgcat attcgatatt accgcatcac ttacggcgaa   120
acaggaggca atagccctgt ccaggagttc actgtgcctc gttctcgtca tacagctacc   180
atcagcggcc ttaaacctgg cgttgattat accatcactg tgtatgctgt cacttactac   240
aacgaagctg actactctca gatcccaatt tccattaatt accgcacaga aattgacaaa   300
ccatcccagc accatcacca ccaccactga                                      330
```

<210> SEQ ID NO 231
<211> LENGTH: 330
<212> TYPE: DNA
<213> ORGANISM: Artificial Sequence
<220> FEATURE:
<223> OTHER INFORMATION: Clone ID 1487H04

<400> SEQUENCE: 231

```
atgggagttt ctgatgtgcc gcgcgacctg gaagtggttg ctgccacccc caccagcctg    60
ctgatcagct ggggtcatta cccgatgcat gttcgatatt accgcatcac ttacggcgaa   120
acaggaggca atagccctgt ccaggagttc actgtgcctg ctcgtcagta cacagctacc   180
atcagcggcc ttaaacctgg cgttgattat accatcactg tgtatgctgt cacttactac   240
caggaatacg aataccgtta cataccaatt tccattaatt accgcacaga aattgacaaa   300
ccatcccagc accatcacca ccaccactga                                      330
```

<210> SEQ ID NO 232
<211> LENGTH: 330
<212> TYPE: DNA
<213> ORGANISM: Artificial Sequence
<220> FEATURE:
<223> OTHER INFORMATION: Clone ID 1490E02

<400> SEQUENCE: 232

```
atgggagttt ctgatgtgcc gcgcgacctg gaagtggttg ctgccacccc caccagcctg    60
ctgatcagct ggggtcatta cccgatgcat gttcgatatt accgcatcac ttacggcgaa   120
acaggaggca atagccctgt ccaggagttc actgtgcctc gtactcagta cacagctacc   180
atcagcggcc ttaaacctgg cgttgattat accatcactg tgtatgctgt cacttactac   240
aacgaagctg actactctca gatcccaatt tccattaatt accgcacaga aattgacaaa   300
ccatcccagc accatcacca ccaccactga                                      330
```

<210> SEQ ID NO 233
<211> LENGTH: 330
<212> TYPE: DNA
<213> ORGANISM: Artificial Sequence
<220> FEATURE:
<223> OTHER INFORMATION: Clone ID 1490G02

<400> SEQUENCE: 233

```
atgggagttt ctgatgtgcc gcgcgacctg gaagtggttg ctgccacccc caccagcctg    60
```

```
ctgatcagct ggggtcatta cccgatgcat gttcgatatt accgcatcac ttacggcgaa    120
acaggaggca atagccctgt ccaggagttc actgtgcctc cgcgttacca tacagctacc    180
atcagcggcc ttaaacctgg cgttgattat accatcactg tgtatgctgt cacttactac    240
atggaagaaa aatacgctgt tatcccaatt tccattaatt accgcacaga aattgacaaa    300
ccatcccagc accatcacca ccaccactga                                     330
```

```
<210> SEQ ID NO 234
<211> LENGTH: 330
<212> TYPE: DNA
<213> ORGANISM: Artificial Sequence
<220> FEATURE:
<223> OTHER INFORMATION: Clone ID 1490H05

<400> SEQUENCE: 234
atgggagttt ctgatgtgcc gcgcgacctg gaagtggttg ctgccacccc caccagcctg    60
ctgatcagct ggggtcatta cccgctgcat gttcgatatt accgcatcac ttacggcgaa    120
acaggaggca atagccctgt ccaggagttc actgtgccta tgcgtcagca tacagctacc    180
atcagcggcc ttaaacctgg cgttgattat accatcactg tgtatgctgt cacttactac    240
gctcaggaaa actacaaaga aatcccaatt tccattaatt accgcacaga aattgacaaa    300
ccatcccagc accatcacca ccaccactga                                     330
```

```
<210> SEQ ID NO 235
<211> LENGTH: 330
<212> TYPE: DNA
<213> ORGANISM: Artificial Sequence
<220> FEATURE:
<223> OTHER INFORMATION: Clone ID 1490B03

<400> SEQUENCE: 235
atgggagttt ctgatgtgcc gcgcgacctg gaagtggttg ctgccacccc caccagcctg    60
ctgatcagct ggggtcatta cccgctgcat gttcgatatt accgcatcac ttacggcgaa    120
acaggaggca atagccctgt ccaggagttc actgtgcctt ctcgtaaata cacagctacc    180
atcagcggcc ttaaacctgg cgttgattat accatcactg tgtatgctgt cacttactac    240
aaagaagcta actatcgtga aatcccaatt tccattaatt accgcacaga aattgacaaa    300
ccatcccagc accatcacca ccaccactga                                     330
```

```
<210> SEQ ID NO 236
<211> LENGTH: 330
<212> TYPE: DNA
<213> ORGANISM: Artificial Sequence
<220> FEATURE:
<223> OTHER INFORMATION: Clone ID 1490H06

<400> SEQUENCE: 236
atgggagttt ctgatgtgcc gcgcgacctg gaagtggttg ctgccacccc caccagcctg    60
ctgatcagct ggggtcatta cccgctgcat atccgatatt accgcatcac ttacggcgaa    120
acaggaggca atagccctgt ccaggagttc actgtgcctc gtcagaaata cacagctacc    180
atcagcggcc ttaaacctgg cgttgattat accatcactg tgtatgctgt cacttactac    240
aacgaagctg actactctca gatcccaatt tccattaatt accgcacaga aattgacaaa    300
ccatcccagc accatcacca ccaccactga                                     330
```

```
<210> SEQ ID NO 237
```

```
<211> LENGTH: 330
<212> TYPE: DNA
<213> ORGANISM: Artificial Sequence
<220> FEATURE:
<223> OTHER INFORMATION: Clone ID 1490A07

<400> SEQUENCE: 237
atgggagttt ctgatgtgcc gcgcgacctg gaagtggttg ctgccacccc caccagcctg      60
ctgatcagct ggggtcatta cccgctgcat atccgatatt accgcatcac ttacggcgaa     120
acaggaggca atagccctgt ccaggagttc actgtgcctc atgctaaata cacagctacc     180
atcagcggcc ttaaacctgg cgttgattat accatcactg tgtatgctgt cacttactac     240
gctcaggaaa actacaaaga aatcccaatt tccattaatt accgcacaga aattgacaaa     300
ccatcccagc accatcacca ccaccactga                                      330

<210> SEQ ID NO 238
<211> LENGTH: 330
<212> TYPE: DNA
<213> ORGANISM: Artificial Sequence
<220> FEATURE:
<223> OTHER INFORMATION: Clone ID 1490C07

<400> SEQUENCE: 238
atgggagttt ctgatgtgcc gcgcgacctg gaagtggttg ctgccacccc caccagcctg      60
ctgatcagct ggggtcatta cccgctgcat gttcgatatt accgcatcac ttacggcgaa     120
acaggaggca atagccctgt ccaggagttc actgtgcctt ctaaccgtta cacagctacc     180
atcagcggcc ttaaacctgg cgttgattat accatcactg tgtatgctgt cacttactac     240
aacgaagctg actactctca gatcccaatt tccattaatt accgcacaga aattgacaaa     300
ccatcccagc accatcacca ccaccactga                                      330

<210> SEQ ID NO 239
<211> LENGTH: 330
<212> TYPE: DNA
<213> ORGANISM: Artificial Sequence
<220> FEATURE:
<223> OTHER INFORMATION: Clone ID 1490H08

<400> SEQUENCE: 239
atgggagttt ctgatgtgcc gcgcgacctg gaagtggttg ctgccacccc caccagcctg      60
ctgatcagct ggggtcatta cccgctgcat atccgatatt accgcatcac ttacggcgaa     120
acaggaggca atagccctgt ccaggagttc actgtgccta acacttctca tacagctacc     180
atcagcggcc ttaaacctgg cgttgattat accatcactg tgtatgctgt cacttactac     240
aacgaagctg actactctca gatcccaatt tccattaatt accgcacgga aattgacaaa     300
ccatcccagc accatcacca ccaccactga                                      330

<210> SEQ ID NO 240
<211> LENGTH: 330
<212> TYPE: DNA
<213> ORGANISM: Artificial Sequence
<220> FEATURE:
<223> OTHER INFORMATION: Clone ID 1491A05

<400> SEQUENCE: 240
atgggagttt ctgatgtgcc gcgcgacctg gaagtggttg ctgccacccc caccagcctg      60
ctgatcagct ggggtcatta cccgctgcat gttcgatatt accgcatcac ttacggcgaa     120
acaggaggca atagccctgt ccaggagttc actgtgcctt ctcaggttta cacagctacc     180
```

```
atcagcggcc ttaaacctgg cgttgattat accatcactg tgtatgctgt cacttactac    240
gctcaggaaa actacaaaga aatcccaatt tccattaatt accgcacaga aattgacaaa    300
ccatcccagc accatcacca ccaccactga                                     330
```

<210> SEQ ID NO 241
<211> LENGTH: 330
<212> TYPE: DNA
<213> ORGANISM: Artificial Sequence
<220> FEATURE:
<223> OTHER INFORMATION: Clone ID 1571H03

<400> SEQUENCE: 241

```
atgggagttt ctgatgtgcc gcgcgacctg gaagtggttg ctgccacccc caccagcctg     60
ctgatcagct ggggtcatta cccgctgcat gttcgatatt accgcatcac ttacggcgaa    120
acaggaggca atagccctgt ccaggagttc actgtgccta accgtgttta cacagctacc    180
atcagcggcc ttaaacctgg cgttgattat accatcactg tgtatgctgt cacttactac    240
gctcaggaag aataccatat catcccaatt tccattaatt accgcacaga aattgacaaa    300
ccatcccagc accatcacca ccaccactga                                     330
```

<210> SEQ ID NO 242
<211> LENGTH: 330
<212> TYPE: DNA
<213> ORGANISM: Artificial Sequence
<220> FEATURE:
<223> OTHER INFORMATION: Clone ID 1571G04

<400> SEQUENCE: 242

```
atgggagttt ctgatgtgcc scgcgacctg gaagtggttg ctgccacccc caccagcctg     60
ctgatcagct ggggtcatta cccgctgcat gttcgatatt accgcatcac ttacggcgaa    120
acaggaggca atagccctgt ccaggagttc actgtgcctc cgcgttctca cacagctacc    180
atcagcggcc ttaaacctgg cgttgattat accatcactg tgtatgctgt cacttactac    240
gctcaggaaa actacaaaga aatcccaatt tccattaatt accgcacaga aattgacaaa    300
ccatcccagc accatcacca ccaccactga                                     330
```

<210> SEQ ID NO 243
<211> LENGTH: 330
<212> TYPE: DNA
<213> ORGANISM: Artificial Sequence
<220> FEATURE:
<223> OTHER INFORMATION: Clone ID 1571G06

<400> SEQUENCE: 243

```
atgggagttt ctgatgtgcc gcgcgacctg gaagtggttg ctgccacccc caccagcctg     60
ctgatcagct ggggtcatta cccgctgcac ctgcgatatt accgcatcac ttacggcgaa    120
acaggaggca atagccctgt ccaggagttc actgtgcctc gtactaaata cacagctacc    180
atcagcggcc ttaaacctgg cgttgattat accatcactg tgtatgctgt cacttactac    240
aaagaagctg actactctca gatcccaatt tccattaatt accgcacaga aattgacaaa    300
ccatcccagc accatcacca ccaccactga                                     330
```

<210> SEQ ID NO 244
<211> LENGTH: 330
<212> TYPE: DNA
<213> ORGANISM: Artificial Sequence
<220> FEATURE:

<223> OTHER INFORMATION: Clone ID 1571F10

<400> SEQUENCE: 244

| | |
|---|---|
| atgggagttt ctgatgtgcc gcgcgacctg gaagtggttg ctgccacccc caccagcctg | 60 |
| ctgatcagct ggggtcatta cccgctgcat atccgatatt accgcatcac ttacggcgaa | 120 |
| acaggaggca atagccctgt ccaggagttc actgtgcctt ctcgttacca tacagctacc | 180 |
| atcagcggcc ttaaacctgg cgttgattat accatcactg tgtatgctgt cacttactac | 240 |
| gaacaggttg ataccgtga atcccaatt tccattaatt accgcacaga aattgacaaa | 300 |
| ccatcccagc accatcacca ccaccactga | 330 |

<210> SEQ ID NO 245
<211> LENGTH: 330
<212> TYPE: DNA
<213> ORGANISM: Artificial Sequence
<220> FEATURE:
<223> OTHER INFORMATION: Clone ID 1572D04

<400> SEQUENCE: 245

| | |
|---|---|
| atgggagttt ctgatgtgcc gcgcgacctg gaagtggttg ctgccacccc caccagcctg | 60 |
| ctgatcagct ggggtcatta cccgatgcat gttcgatatt accgcatcac ttacggcgaa | 120 |
| acaggaggca atagccctgt ccaggagttc actgtgcctc cgcgtcgtta cacagctacc | 180 |
| atcagcggcc ttaaacctgg cgttgattat accatcactg tgtatgctgt cacttactac | 240 |
| gaacagccga tctacgccac tatcccaatt tccattaatt accgcacaga aattgacaaa | 300 |
| ccatcccagc accatcacca ccaccactga | 330 |

<210> SEQ ID NO 246
<211> LENGTH: 330
<212> TYPE: DNA
<213> ORGANISM: Artificial Sequence
<220> FEATURE:
<223> OTHER INFORMATION: Clone ID 1572F05
<220> FEATURE:
<221> NAME/KEY: misc_feature
<223> OTHER INFORMATION: 1572F05

<400> SEQUENCE: 246

| | |
|---|---|
| atgggagttt ctgatgtgcc gcgcgacctg gaagtggttg ctgccacccc caccagcctg | 60 |
| ctgatcagct ggggtcatta cccgctgcat atccgatatt accgcatcac ttacggcgaa | 120 |
| acaggaggca atagccctgt ccaggagttc actgtgcctc gtcagaaata cacagctacc | 180 |
| atcagcggcc ttaaacctgg cgttgattat accatcactg tgtatgctgt cacttactac | 240 |
| aacgaagctg actactctca gatcccaatt tccattaatt accgcacaga aattgacaaa | 300 |
| ccatcccagc accatcacca ccaccactga | 330 |

<210> SEQ ID NO 247
<211> LENGTH: 330
<212> TYPE: DNA
<213> ORGANISM: Artificial Sequence
<220> FEATURE:
<223> OTHER INFORMATION: Clone ID 1572G06

<400> SEQUENCE: 247

| | |
|---|---|
| atgggagttt ctgatgtgcc gcgcgacctg gaagtggttg ctgccacccc caccagcctg | 60 |
| ctgatcagct ggggtcatta cccgctgcat gttcgatatt accgcatcac ttacggcgaa | 120 |
| acaggaggca atagccctgt ccaggagttc actgtgcctc gttacaaata cacagctacc | 180 |

```
atcagcggcc ttaaacctgg cgttgattat accatcactg tgtatgctgt cacttactac    240
gctcaggaaa actacaaaga aatcccaatt tccattaatt accgcacaga aattgacaaa    300
ccatcccagc accatcacca ccaccactga                                      330

<210> SEQ ID NO 248
<211> LENGTH: 330
<212> TYPE: DNA
<213> ORGANISM: Artificial Sequence
<220> FEATURE:
<223> OTHER INFORMATION: Clone ID 1572B10

<400> SEQUENCE: 248
atgggagttt ctgatgtgcc gcgcgacctg gaagtggttg ctgccacccc caccagcctg    60
ctgatcagct ggggtcatta cccgatgcat gttcgatatt accgcatcac ttacggcgaa    120
acaggaggca atagccctgt ccaggagttc actgtgcctg ttccgcgtca tacagctacc    180
atcagcggcc ttaaacctgg cgttgattat accatcactg tgtatgctgt cacttactac    240
aacgaagctg actactctca gatcccaatt tccattaatt accgcacaga aattgacaaa    300
ccatcccagc accatcacca ccaccactga                                      330

<210> SEQ ID NO 249
<211> LENGTH: 330
<212> TYPE: DNA
<213> ORGANISM: Artificial Sequence
<220> FEATURE:
<223> OTHER INFORMATION: Clone ID 1572C09

<400> SEQUENCE: 249
atgggagttt ctgatgtgcc gcgcgacctg gaagtggttg ctgccacccc caccagcctg    60
ctgatcagct ggggtcatta cccgatgcat atccgatatt accgcatcac ttacggcgaa    120
acaggaggca atagccctgt ccaggagttc actgtgccta ctccgaaaca tacagctacc    180
atcagcggcc ttaaacctgg cgttgattat accatcactg tgtatgctgt cacttactac    240
aacgaagctg actactctca gatcccaatt tccattaatt accgcacaga aattgacaaa    300
ccatcccagc accatcacca ccaccactga                                      330

<210> SEQ ID NO 250
<211> LENGTH: 330
<212> TYPE: DNA
<213> ORGANISM: Artificial Sequence
<220> FEATURE:
<223> OTHER INFORMATION: Clone ID 1572H05

<400> SEQUENCE: 250
atgggagttt ctgatgtgcc gcgcgacctg gaagtggttg ctgccacccc caccagcctg    60
ctgatcagct ggggtcatta cccgctgcat atccgatatt accgcatcac ttacggcgaa    120
acaggaggca atagccctgt ccaggagttc actgtgcctc gttctaaata cacagctacc    180
atcagcggcc ttaaacctgg cgttgattat accatcactg tgtatgctgt cacttactac    240
gaacaggttg aataccgtga aatcccaatt tccattaatt accgcacaga aattgacaaa    300
ccatcccagc accatcacca ccaccactga                                      330

<210> SEQ ID NO 251
<211> LENGTH: 330
<212> TYPE: DNA
<213> ORGANISM: Artificial Sequence
<220> FEATURE:
<223> OTHER INFORMATION: Clone ID 1572H08
```

-continued

```
<400> SEQUENCE: 251
atgggagttt ctgatgtgcc gcgcgacctg gaagtggttg ctgccacccc caccagcctg      60
ctgatcagct ggggtcatta cccgctgcat gttcgatatt accgcatcac ttacggcgaa     120
acaggaggca atagccctgt ccaggagttc actgtgcctt ctcgtaaata cacagctacc     180
atcagcggcc ttaaacctgg cgttgattat accatcactg tgtatgctgt cacttactac     240
aacgaagctg actactctca gatcccaatt tccattaatt accgcacaga aattgacaaa     300
ccatcccagc accatcacca ccaccactga                                      330

<210> SEQ ID NO 252
<211> LENGTH: 330
<212> TYPE: DNA
<213> ORGANISM: Artificial Sequence
<220> FEATURE:
<223> OTHER INFORMATION: Clone ID 1550A07

<400> SEQUENCE: 252
atgggagttt ctgatgtgcc gcgcgacctg gaagtggttg ctgccacccc caccagcctg      60
ctgatcagct ggggtcatta cccgatgcat gttcgatatt accgcatcac ttacggcgaa     120
acaggaggca atagccctgt ccaggagttc actgtgcctg ttccgcgtta cacagctacc     180
atcagcggcc ttaaacctgg cgttgattat accatcactg tgtatgctgt cacttactac     240
gctcaggaaa actacaaaga aatcccaatt tccattaatt accgcacaga aattgacaaa     300
ccatcccagc accatcacca ccaccactga                                      330

<210> SEQ ID NO 253
<211> LENGTH: 330
<212> TYPE: DNA
<213> ORGANISM: Artificial Sequence
<220> FEATURE:
<223> OTHER INFORMATION: Clone ID 1550C05

<400> SEQUENCE: 253
atgggagttt ctgatgtgcc gcgcgacctg gaagtggttg ctgccacccc caccagcctg      60
ctgatcagct ggggtcatta cccgatgcat gttcgatatt accgcatcac ttacggcgaa     120
acaggaggca atagccctgt ccaggagttc actgtgcctc cgcgtcgtta cacagctacc     180
atcagcggcc ttaaacctgg cgttgattat accatcactg tgtatgctgt cacttactac     240
aacgaagctg actactctca gatcccaatt tccattaatt accgcacaga aattgacaaa     300
ccatcccagc accatcacca ccaccactga                                      330

<210> SEQ ID NO 254
<211> LENGTH: 330
<212> TYPE: DNA
<213> ORGANISM: Artificial Sequence
<220> FEATURE:
<223> OTHER INFORMATION: Clone ID 1550E03

<400> SEQUENCE: 254
atgggagttt ctgatgtgcc gcgcgacctg gaagtggttg ctgccacccc caccagcctg      60
ctgatcagct ggggtcatta cccgctgcat atccgatatt accgcatcac ttacggcgaa     120
acaggaggca atagccctgt ccaggagttc actgtgcctc gtatgcgtca tacagctacc     180
atcagcggcc ttaaacctgg cgttgattat accatcactg tgtatgctgt cacttactac     240
tccgaagaac tgtacaaata catcccaatt tccattaatt accgcacaga aattgacaaa     300
```

-continued

```
ccatcccagc accatcacca ccaccactga                                    330

<210> SEQ ID NO 255
<211> LENGTH: 330
<212> TYPE: DNA
<213> ORGANISM: Artificial Sequence
<220> FEATURE:
<223> OTHER INFORMATION: Clone ID 1550E06

<400> SEQUENCE: 255
atgggagttt ctgatgtgcc gcgcgacctg gaagtggttg ctgccacccc caccagcctg    60
ctgatcagct ggggtcatta cccgatgcat gttcgatatt accgcatcac ttacggcgaa   120
acaggaggca atagccctgt ccaggagttc actgtgcctc cgccgcgtca taccgctacc   180
atcagcggcc ttaaacctgg cgttgattat accatcactg tgtatgctgt cacttactac   240
gctcaggaaa actacaaaga aatcccaatt tccattaatt accgcacaga aattgacaaa   300
ccatcccagc accatcacca ccaccactga                                    330

<210> SEQ ID NO 256
<211> LENGTH: 330
<212> TYPE: DNA
<213> ORGANISM: Artificial Sequence
<220> FEATURE:
<223> OTHER INFORMATION: Clone ID 1550H05

<400> SEQUENCE: 256
atgggagttt ctgatgtgcc gcgcgacctg gaagtggttg ctgccacccc caccagcctg    60
ctgatcagct ggggtcatta cccgctgcat gttcgatatt accgcatcac ttacggcgaa   120
acaggaggca atagccctgt ccaggagttc actgtgcctc gtcagatcta cacagctacc   180
atcagcggcc ttaaacctgg cgttgattat accatcactg tgtatgctgt cacttactac   240
aacgaagctg actactctca gatcccaatt tccattaatt accgcacaga aattgacaaa   300
ccatcccagc accatcacca ccaccactga                                    330

<210> SEQ ID NO 257
<211> LENGTH: 7
<212> TYPE: PRT
<213> ORGANISM: Artificial Sequence
<220> FEATURE:
<223> OTHER INFORMATION: BC LOOP
<220> FEATURE:
<221> NAME/KEY: misc_feature
<222> LOCATION: (5)..(5)
<223> OTHER INFORMATION: Xaa can be Met or Leu
<220> FEATURE:
<221> NAME/KEY: misc_feature
<222> LOCATION: (7)..(7)
<223> OTHER INFORMATION: Xaa can be Ile or Val

<400> SEQUENCE: 257

Gly His Tyr Pro Xaa His Xaa
1               5

<210> SEQ ID NO 258
<211> LENGTH: 10
<212> TYPE: PRT
<213> ORGANISM: Artificial Sequence
<220> FEATURE:
<223> OTHER INFORMATION: FG LOOP
<220> FEATURE:
<221> NAME/KEY: misc_feature
<222> LOCATION: (3)..(6)
<223> OTHER INFORMATION: Xaa can be any naturally occurring amino acid
<220> FEATURE:
```

```
<221> NAME/KEY: misc_feature
<222> LOCATION: (8)..(9)
<223> OTHER INFORMATION: Xaa can be any naturally occurring amino acid

<400> SEQUENCE: 258

Tyr Tyr Xaa Xaa Xaa Xaa Tyr Xaa Xaa Ile
1               5                   10
```